(12) United States Patent
Paschal

(10) Patent No.: US 10,716,898 B2
(45) Date of Patent: Jul. 21, 2020

(54) MAGNETIC DRIVER DEVICE USED TO POWER AN AUTO INJECTOR

(71) Applicant: Dynamic Magnetics, LLC, Franklin, TN (US)

(72) Inventor: Richard C. Paschal, Nashville, TN (US)

(73) Assignee: Dynamic Magnetics, LLC, Franklin, TN (US)

( * ) Notice: Subject to any disclaimer, the term of this patent is extended or adjusted under 35 U.S.C. 154(b) by 98 days.

(21) Appl. No.: 16/125,286

(22) Filed: Sep. 7, 2018

(65) Prior Publication Data

US 2019/0022318 A1 Jan. 24, 2019

Related U.S. Application Data

(62) Division of application No. 15/848,984, filed on Dec. 20, 2017, now Pat. No. 10,143,802.

(60) Provisional application No. 62/597,278, filed on Dec. 11, 2017, provisional application No. 62/437,115, filed on Dec. 21, 2016.

(51) Int. Cl.
*A61M 5/20* (2006.01)
*A61M 5/24* (2006.01)
A61M 5/315 (2006.01)

(52) U.S. Cl.
CPC ............... *A61M 5/20* (2013.01); *A61M 5/24* (2013.01); *A61M 5/3157* (2013.01); *A61M 2005/206* (2013.01); *A61M 2205/8287* (2013.01)

(58) Field of Classification Search
CPC ........ A61M 5/2033; A61M 5/20; A61M 5/30; A61M 5/24; A61M 5/3204; A61M 5/14248; A61M 5/31551; A61M 5/326; A61M 5/3158; A61M 5/3202; A61M 5/31541; A61M 5/3287; A61M 5/14546; A61M 5/31501; A61M 5/3157; A61M 5/31585
See application file for complete search history.

(56) References Cited

U.S. PATENT DOCUMENTS

| 2,869,049 | A | * | 1/1959 | Dietz | ................... | H01H 53/015 |
| | | | | | | 335/222 |
| 2012/0095435 | A1 | * | 4/2012 | Hunter | ................ | A61M 5/3015 |
| | | | | | | 604/500 |
| 2012/0130343 | A1 | * | 5/2012 | Freeman | ............ | A61B 5/15178 |
| | | | | | | 604/506 |

* cited by examiner

*Primary Examiner* — Manuel A Mendez
(74) *Attorney, Agent, or Firm* — Bass, Berry & Sims, PLC

(57) ABSTRACT

A device has a hollow guide shell including an injection end and a longitudinal axis. An actuator magnet is disposed in the hollow guide shell. An injection pin is coupled to the actuator magnet. A driver magnet is positioned on the device radially outward from the actuator magnet. A fluid cartridge is disposed in the injection end of the hollow guide shell, the fluid cartridge including a needle and a plunger. The driver magnet selectively exerts an injection force on the actuator magnet in a direction oriented towards the injection end of the hollow guide shell to engage the injection pin with the fluid cartridge. A liquid, gas or other agent can selectively be ejected from the cartridge by the device to inject the fluid, gas or other agent into another object.

20 Claims, 33 Drawing Sheets

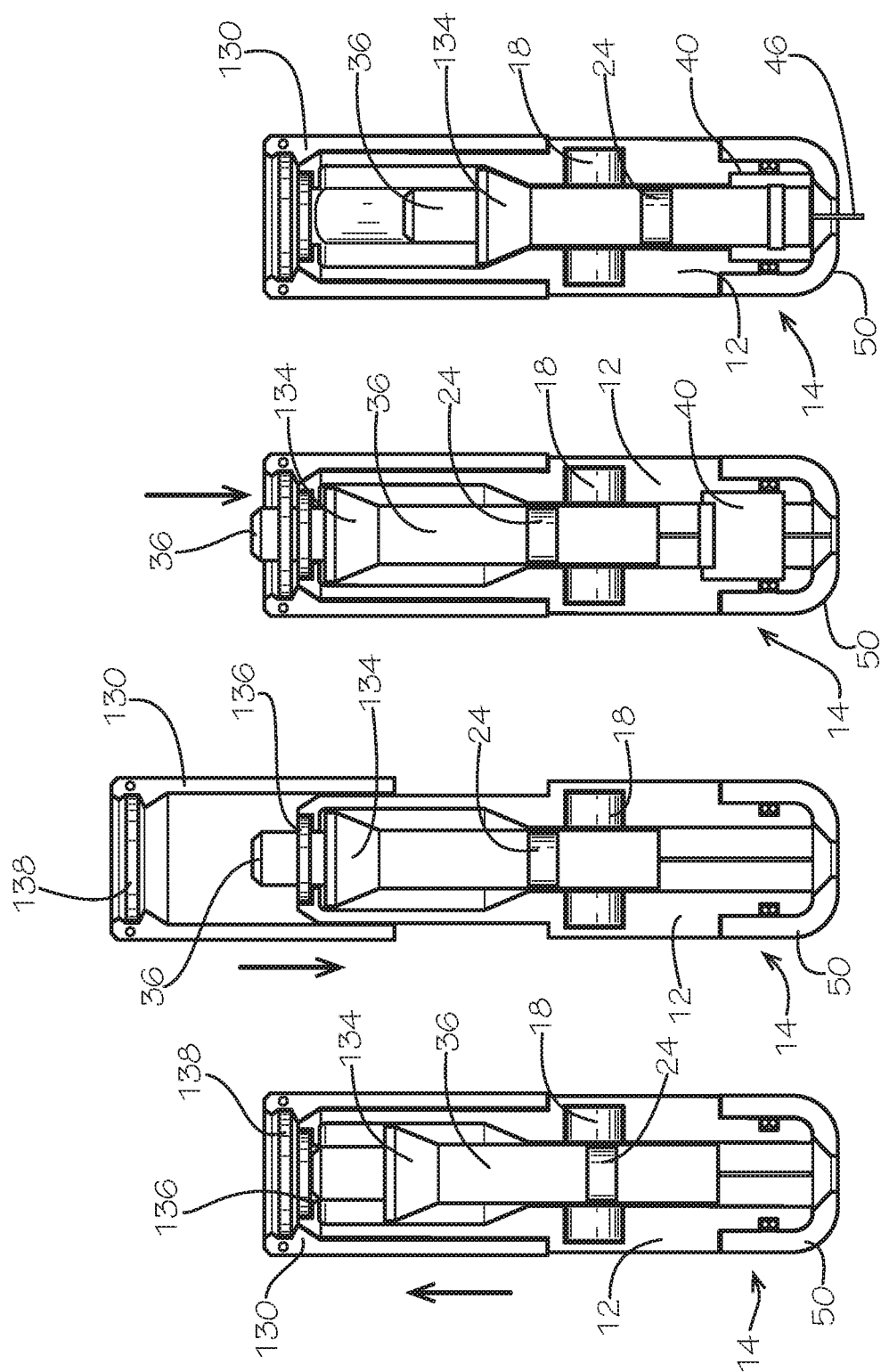

MAGNETIC DRIVER DEVICE USED TO POWER AN AUTO INJECTOR

CROSS-REFERENCES TO RELATED APPLICATION

This application is a divisional patent application of U.S. patent application Ser. No. 15/848,984, filed Dec. 20, 2017, now patented as U.S. Pat. No. 10,143,802, issued on Dec. 4, 2018, which is a non provisional of U.S. Patent Application Ser. No. 62/597,278 filed Dec. 11, 2017 entitled AUTO INJECTION DEVICE HAVING A MAGNETIC DRIVER, and a non provisional of U.S. Patent Application Ser. No. 62/437,115, filed Dec. 21, 2016 entitled AUTO INJECTION DEVICE HAVING A MAGNETIC DRIVER, of which both are herein incorporated by reference in their entirety.

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND OF THE INVENTION

The present disclosure relates generally to fluid injection devices. More particularly, the present disclosure relates to injecting fluids into desired objects. For instance, injection devices can be used in the medical or veterinary fields to deliver drugs to a patient or animal. In various other industries, injection devices can be used to inject or deliver various liquids, gases, chemicals, materials, etc. into another body or medium as desired.

Some conventional methods for injecting fluids into a desired object can involve the use of a syringe. One problem with conventional syringes is that a user must first insert the syringe into the desired object, and then manually deliver the fluids into the desired object. A substantial amount of time can lapse between the initial insertion and the completion of the injection process, or fluid delivery. Such a lapse of time can be undesirable when it is beneficial for injection to occur quickly, or if the object being injected is prone to movement during injection. One such instance can be in a patient setting when the patient is uneasy about injections or needles, for instance if the patient is a child or generally has a fear of needles. A lapse of time between insertion of the syringe and delivery of the medicine to the patient affords the patient the opportunity to move or jerk suddenly, which can affect the proper delivery of the drug to the patient and is generally undesirable. Another such instance is a nurse causing lateral movement of a needle in patient tissue while injecting fluid as a result of the nurse having to manually push or pull a plunger to inject fluid while simultaneously attempting to hold the device stationary.

In other injection devices, delivery of the fluid to the desired object can be automated. Some injection devices can utilize complicated hydraulic or pneumatic systems to provide the required force for injecting the fluid into the desired object. Such injection systems can be cumbersome and expensive and are not conducive for certain applications. In still other injection devices, elastic materials such as springs can be used to provide the force necessary to inject the fluid or gas into the desired object. The springs can be compressed in a loaded or cocked state prior to injection. The springs can be released when desired to inject a fluid contained in the injection device into the desired object. However, springs can wear over time with repeated cycles of compression and decompression, such that the injection force, as well as the depth of the injection produced by the injection device, can gradually change. If the injection characteristics of the injection device change over time, the injection device often will need to be repaired, recalibrated, or replaced entirely.

Additionally, when elastic members such as springs are used as the driving force in injection devices, those devices are typically retained in a cocked state, with a spring in either tension or compression prior to actuation, by a locking device or some other mechanism. As a user actuates the device, the user must disengage the locking mechanism by overcoming the large amount of potential energy and force stored in the spring when in the cocked orientation, which can be cumbersome, particularly in situations where injection must occur quickly.

Auto-injectors are often used in a medical setting to deliver a variety of drugs in emergency or life-threatening situations, for instance in patients having allergic reactions, or exposure to poisons, venoms, or other chemicals and agents. Auto-injectors can also be used to quickly and consistently administer medications needing to be delivered frequently, such as with insulin for diabetic patients, or other maintenance type medication protocols. One large market where auto-injectors are utilized is the Epinephrine injection market. Auto-injectors currently used to deliver epinephrine are relatively expensive, with each injector device costing several hundreds of dollars. Additionally, epinephrine degrades over time, and typically must be replaced once a year if not used. The medicine is also very temperature sensitive. For instance, if an epinephrine auto-injector is left in a hot or cold car, the heat could spoil the medicine such that the medicine must be replaced.

Current auto-injectors are single use, self-contained devices that do not allow for medicine to be removed or replaced within the device without completely disassembling the mechanics of the injector device or actuating the entire device. Current devices are difficult or impossible to reload without the help of a medical professional or technical expert. As such, current protocol requires potential consumers of epinephrine injectors to replace the entire expensive auto-injectors once a year, and additionally if the medicine is exposed to varying temperatures or otherwise compromised. However, the medication inside the auto-injector which has spoiled or been compromised is itself relatively inexpensive when compared to the overall cost of current auto-injectors.

Additionally, because medicine within current auto-injectors cannot be removed or replaced easily, a separate auto-injector often must be purchased and maintained for injections of different medications or medication volumes, different infusion rates, or if different types of needles are desired. For instance, in a hospital setting it may be beneficial to have various medications capable of being injected quickly, more consistently, or in a manner that reduces the risk of inadvertent needle sticks. With current auto injector technology, the hospital would need to purchase a separate auto-injector for each type of medication, each medication volume and each type of needle to be used, and replace each periodically, which can become quite expensive for the hospital. As a result, hospitals continue to overwhelmingly use manual syringes to inject fluids despite the higher risk of accidental needle sticks due to the exposed needles of manual syringes and the need for greater skill and dexterity to consistently and safely use a manual syringe.

What is needed then are improvements to conventional injection devices.

BRIEF SUMMARY

This Brief Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

One aspect of the disclosure is a device having a hollow guide shell including an injection end, a back end, and a longitudinal axis. An actuator magnet is disposed in the hollow guide shell. An injection pin is coupled to the actuator magnet. A driver magnet is positioned on the device radially outward from the actuator magnet. A cartridge is disposed in the injection end of the hollow guide shell, the cartridge including a needle and a plunger. The driver magnet selectively exerts an injection force on the actuator magnet in a direction oriented towards the injection end of the hollow guide shell to engage the injection pin with the cartridge. A liquid or gas can selectively be ejected from the cartridge by the device to inject the fluid into another object as the injection pin engages the cartridge. In some embodiments, the driver magnet can include a first driver magnet pole, a second driver magnet pole, and a driver magnetic axis extending from the first driver magnet pole to the second driver magnet pole, the driver magnetic axis oriented substantially perpendicular to the longitudinal axis of the hollow guide shell. The actuator magnet can include a first actuator magnet pole, a second actuator magnet pole, and an actuator magnetic axis extending from the first actuator magnet pole to the second actuator magnet pole, the actuator magnetic axis oriented substantially parallel to the longitudinal axis of the hollow guide shell.

Another aspect of the present disclosure is an injection device including a hollow guide shell having an injection end, a back end, and a longitudinal axis extending from the injection end to the back end. A slider member is movable relative to the hollow guide shell from a first slider position to a second slider position, the slider member moving in a direction away from the injection end when the slider member moves from the first slider position to the second slider position. A driver magnet is disposed on the slider member, the driver magnet having a first driver magnet pole oriented toward the longitudinal axis. An actuator magnet is disposed in the hollow guide shell along the longitudinal axis. The actuator magnet has a first actuator magnet pole, the first driver magnet pole and the first actuator magnet pole being like poles. The first driver magnet pole can be positioned longitudinally between the first actuator magnet pole and the injection end when the slider member is in the first slider position. The first actuator magnet pole can be positioned longitudinally between the first driver magnet pole and the injection end when the slider member is in the second slider position. An injection pin can be coupled to the actuator magnet and a fluid cartridge can be positioned within the injection end of the hollow guide shell. When the slider member moves from the first slider position to the second slider position, the driver magnet exerts a repulsive injection force on the actuator magnet in a direction towards the injection end of the hollow guide shell.

Another aspect of the present disclosure is a device including a hollow guide shell having an injection end and a longitudinal axis. An actuator magnet is disposed in the hollow guide shell. A driver magnet is positioned on the device radially outward from the actuator magnet. An injection pin can be coupled to the actuator magnet. A fluid cartridge can be positioned within the injection end of the hollow guide shell. The driver magnet can selectively apply an injection force on the actuator magnet in a direction toward the injection end to engage the injection pin with the fluid cartridge. The driver magnet can be selectively movable in a direction substantially perpendicular to the longitudinal axis of the hollow guide shell, to adjust the injection force applied on the actuator magnet by the driver magnet. In some embodiments, a calibration collar is movable relative to the driver magnet in a direction parallel to the longitudinal axis, the calibration collar engaging the driver magnet. The driver magnet can move in a direction substantially perpendicular to the longitudinal axis of the hollow guide shell as the calibration collar moves relative to the driver magnet.

One objective of the present disclosure is to provide an injection device that can be quickly and conveniently actuated to inject a fluid into a desired object.

Another objective is to provide an injection device actuated by magnets.

Another objective is to provide an injection device that can provide a reliable injection of fluids into a desired object.

Another objective is to provide an injection device wherein the actuation or injection force can be adjustable.

Another objective is to provide an injection device that can be reloaded, so that fluid cartridges can conveniently be swapped or reloaded, for instance when expired or spoiled medications need to be replaced, or between uses of the injection device, without having to replace the entire device.

Another objective is to provide an injection device that can accept a variety of cartridges, for example cartridges that contain different types or volumes of medication, which have different penetration speeds or infusion rates, or which contain different gauges, lengths or types of needles so the device can be used for a variety of different patients, treatments and circumstances.

Another objective is to provide an injection device that can be readily re-cocked and reloaded so the device can be used multiple times and for different uses without having to replace the device.

Another objective of the device is to enable persons with limited medical training or limited dexterity to administer injections to themselves or others in a variety of circumstances, ranging from one-time emergency injections to routine injections.

Another objective of the device is to provide an injection device that is simple to operate, has relativity few parts for manufacturing simplicity and greater reliability, can be used for numerous applications achieving economies of scale and cost efficiency, and which requires no electricity, compressed air or other non-inert or unstable components.

Numerous other objects, advantages and features of the present disclosure will be readily apparent to those of skill in the art upon a review of the following drawings and description of a preferred embodiment.

BRIEF DESCRIPTION OF THE DRAWINGS

FIGS. 36-39 show a sequence of the injection device of FIG. 35 being re-cocked, reloaded, and re-actuated.

DETAILED DESCRIPTION

Figure 1:
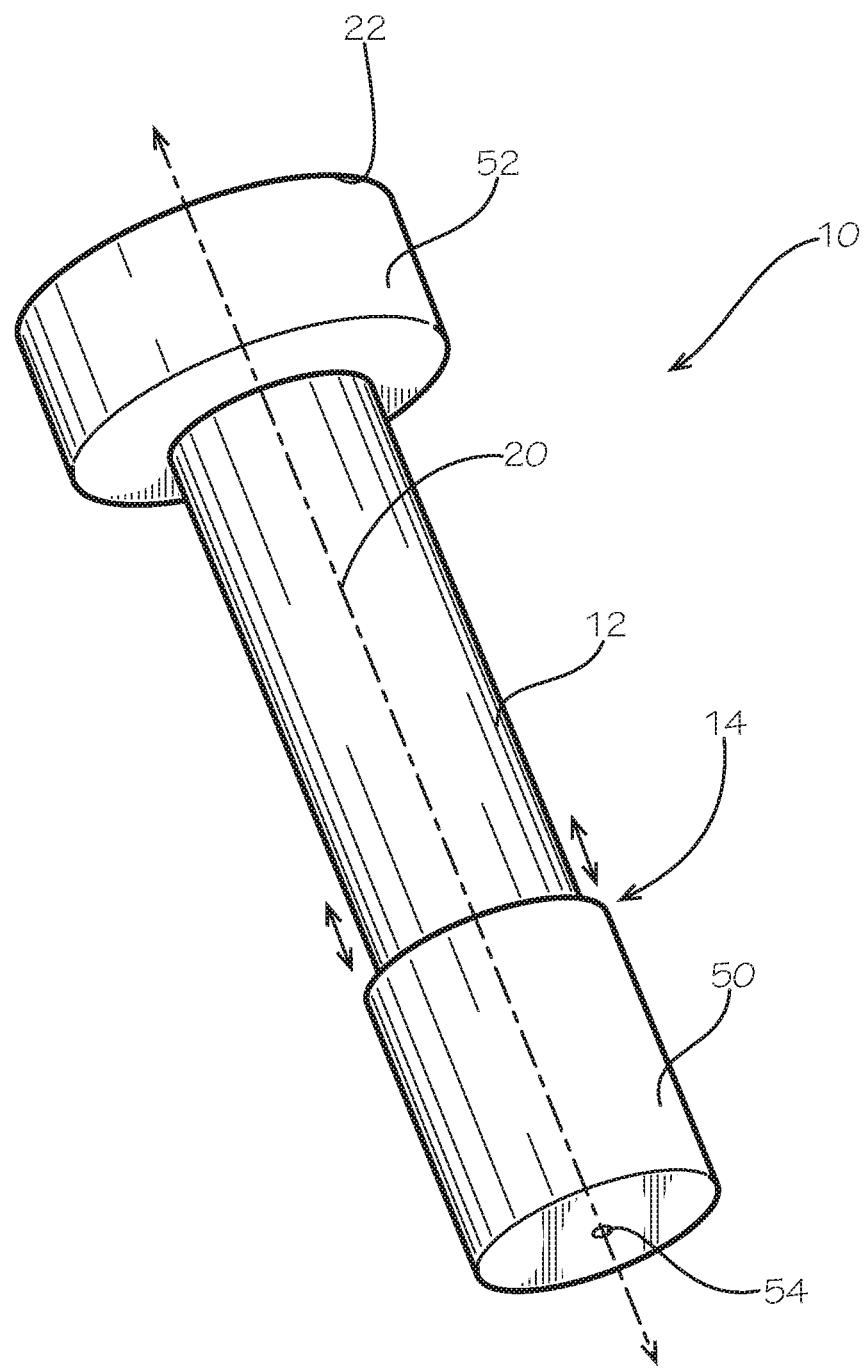
FIG. 1 is a perspective view of an embodiment of an injection device of the present disclosure.

While the making and using of various embodiments of the present invention are discussed in detail below, it should be appreciated that the present invention provides many applicable inventive concepts that are embodied in a wide variety of specific contexts. The specific embodiments discussed herein are merely illustrative of specific ways to make and use the invention and do not delimit the scope of the invention. Those of ordinary skill in the art will recognize numerous equivalents to the specific apparatus and methods described herein. Such equivalents are considered to be within the scope of this invention and are covered by the claims.

In the drawings, not all reference numbers are included in each drawing, for the sake of clarity. In addition, positional terms such as "upper," "lower," "side," "top," "bottom," etc. refer to the apparatus when in the orientation shown in the drawing, or as otherwise described. A person of skill in the art will recognize that the apparatus can assume different orientations when in use.

Figure 2:
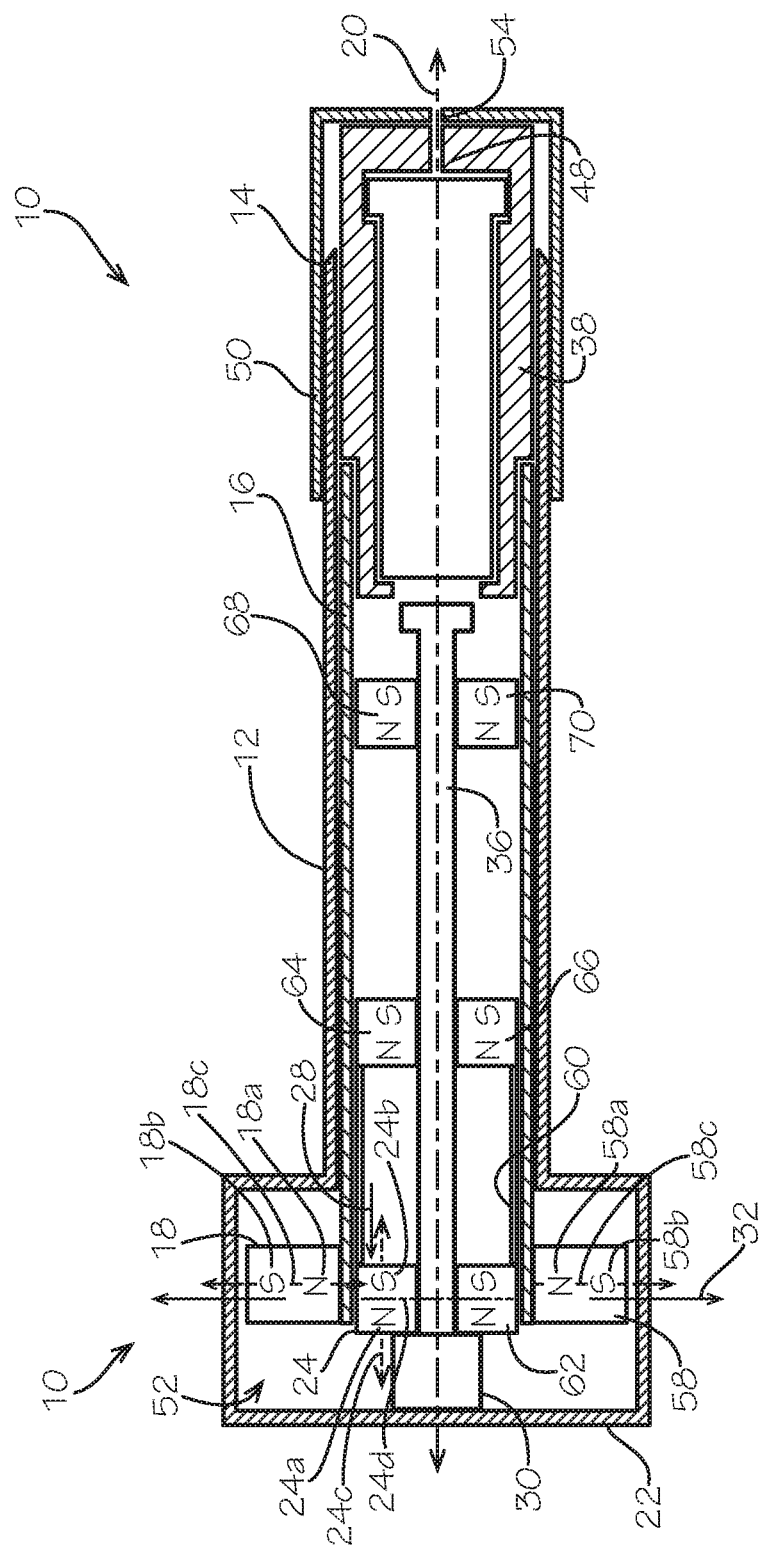
FIG. 2 is a side cross sectional view of the injection device of FIG. 1 with a slider member of the injection device shown in an initial or first slider position.
Figure 3:
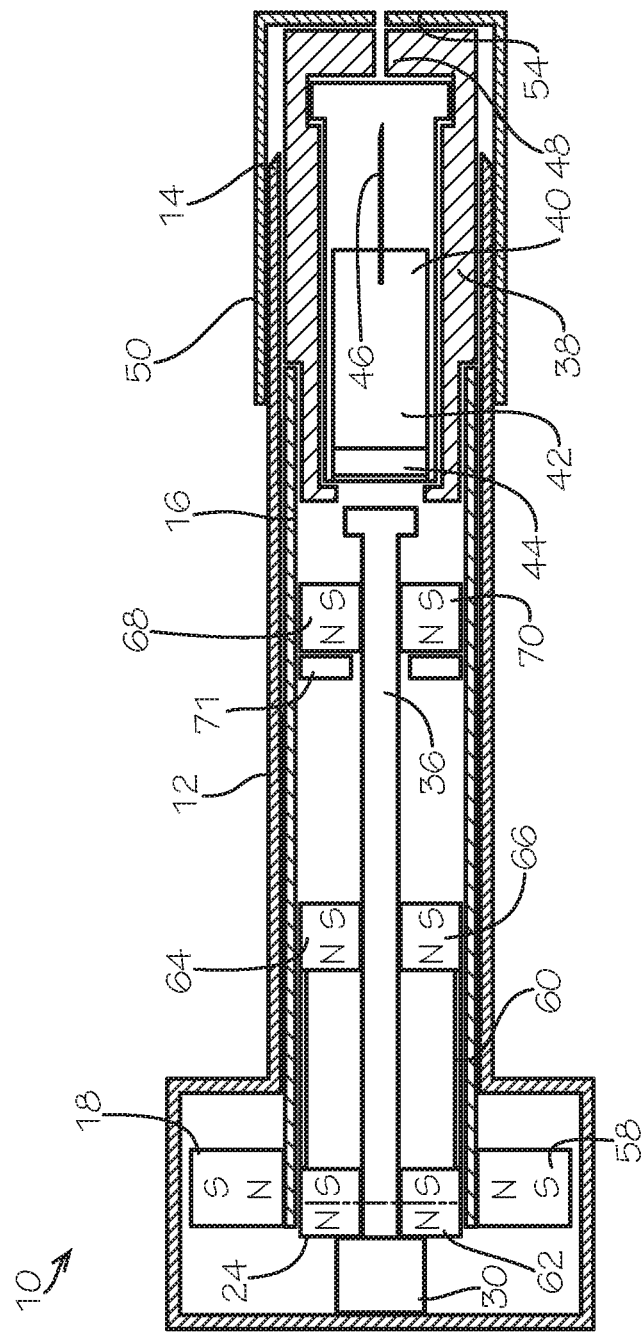
FIG. 3 is a side cross-sectional view of the injection device of FIG. 2 including a fluid cartridge positioned in a cartridge holder of the injection device.

An embodiment of an injection device 10 of the present disclosure is shown in FIGS. 1-3. Injection device 10 can include a hollow guide shell 12. Hollow guide shell 12 can include an injection end 14 and a back end 22. A longitudinal axis 20 of hollow guide shell 12 can extend from injection end 14 to back end 22. An actuator magnet 24 can be disposed in hollow guide shell 12. An injection pin 36 can be coupled to actuator magnet 24. A driver magnet 18 is positioned on device 10 radially outward from actuator magnet 24. A fluid cartridge 40 can be disposed within injection end 14 of hollow guide shell 12, cartridge 40 including a needle 46 and a plunger 44. Driver magnet 18 can selectively exert an injection force on actuator magnet 24 in a direction oriented towards injection end 14 of hollow guide shell 12 to engage injection pin 36 with cartridge 40. A fluid such as a liquid or gas can selectively be ejected from fluid cartridge 40 by device 10 to inject the fluid into a desired object.

Figure 6:
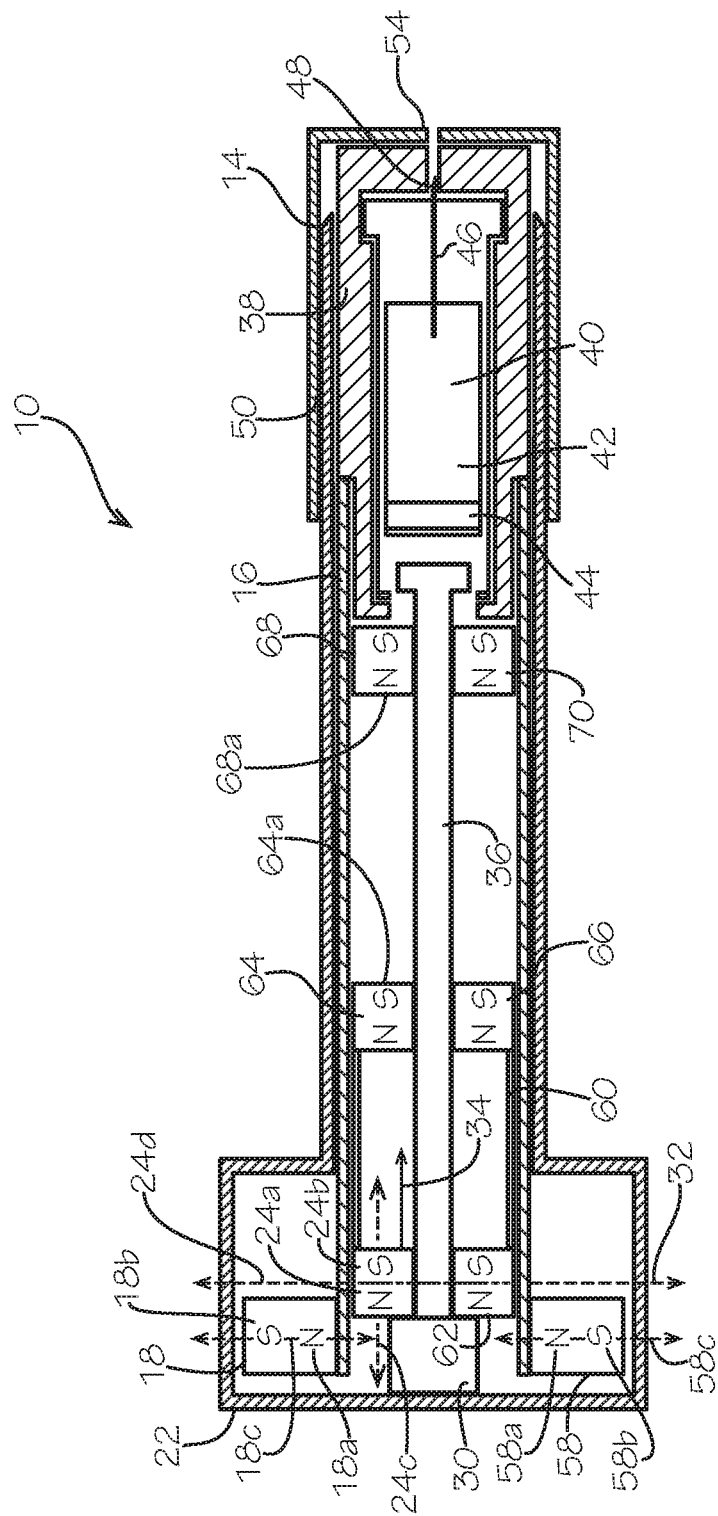
FIG. 6 is a side cross sectional view of the injection device of FIG. 1 showing the slider member in a second slider position.

In some embodiments, device 10 can include a slider member 16 movable relative to hollow guide shell 12 from a first slider position, shown in FIG. 2, to a second slider position, shown in FIG. 6. Slider member 16 can generally move in a direction away from injection end 14 of hollow guide shell 12 as slider member 16 moves from the first slider position to the second slider position. As such, slider member 16 can be positioned closer to injection end 14 of hollow guide shell 12 when slider member is in the first slider position than when slider member 16 is in the second slider position.

Figure 21:
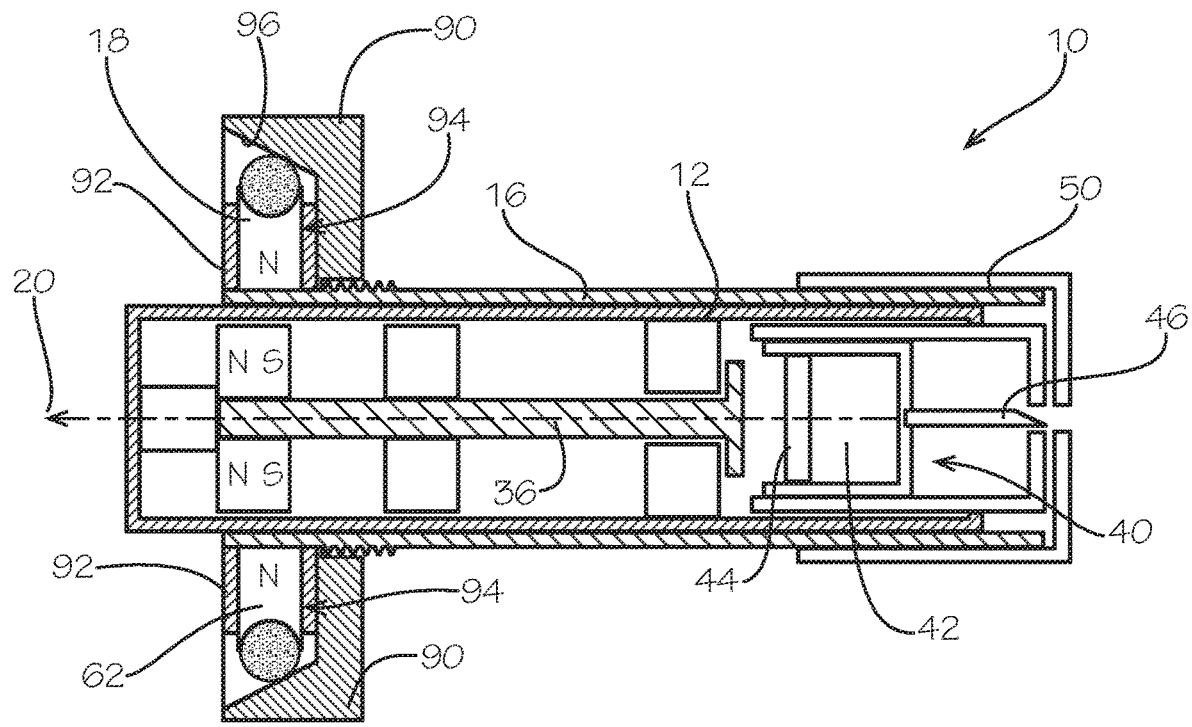
FIG. 21 is a side cross sectional view of another embodiment of an injection device having a calibration collar threadingly disposed on a slider member of the device.
Figure 22:
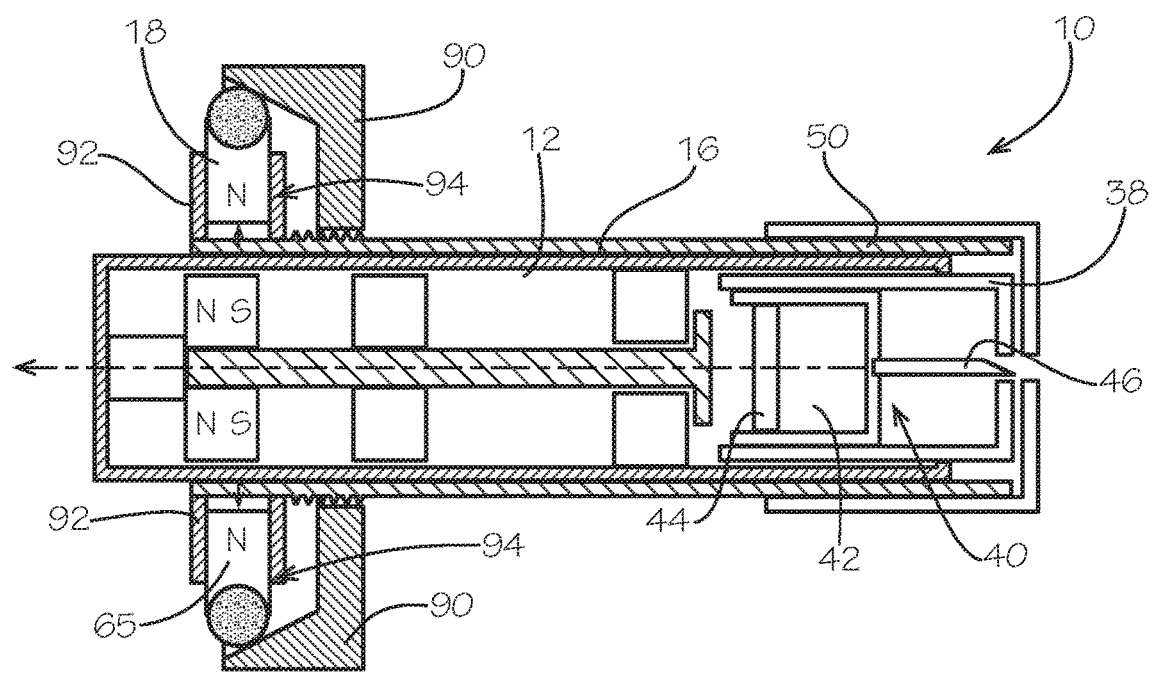
FIG. 22 is a side cross-sectional view of the injection device of FIG. 21 with the calibration collar in a more forward position and driver magnets moved to a radially or laterally outward position.

Slider member 16 is shown as being slidably disposed on hollow guide shell in FIG. 2, and specifically slidably disposed on an inner surface of hollow guide shell 12. In other embodiments, as shown in FIGS. 21-22, slider member 16 can be slidably disposed or movably positioned on an outer surface of hollow guide shell 12. Slider member 16 in either embodiment can be oriented to generally slide along longitudinal axis 20 of hollow guide shell 12 between the first and second slider positions.

Figure 23:
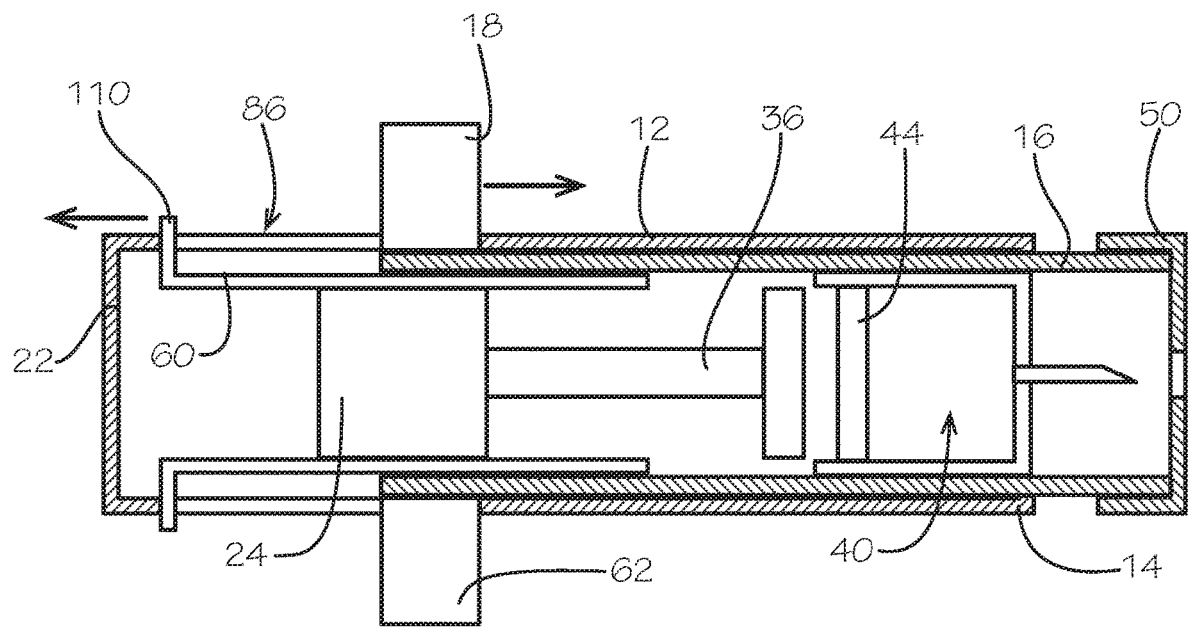
FIG. 23 is a side cross sectional view of another embodiment of an injection device of the present disclosure having a re-cocking or reloading feature.

Driver magnet 18 can be disposed on slider member 16. As slider member 16 moves from a first slider position to a second slider position, driver magnet 18 can move between corresponding first and second driver magnet positions, respectively. In some embodiments, as shown in FIG. 2, slider member 16 and driver magnet 18 are contained within hollow guide shell 12. In some embodiments, hollow guide shell 12 can include a driver magnet receptacle 52. Driver magnet 18 can be positioned within driver magnet receptacle 52 such that as slider member 16 moves from the first slider position to the second slider position, driver magnet 18 can move freely within hollow guide shell 12. In other embodiments, as shown in FIG. 23, hollow guide shell 12 can include a driver magnet aperture 86, driver magnet 18 extending through and movable within the driver magnet aperture 86 as slider member 16 moves from the first slider position to the second slider position. In still other embodiments, slider member 16 and driving magnet 18 are both positioned on an outer side of hollow guide shell 12.

Actuator magnet 24 can be positioned within hollow guide shell 12. Driver magnet 18 and actuator magnet 24 can interact with one another as slider member 16 moves from the first slider position to the second slider position to produce desired movement of various components contained within hollow guide shell 12. In the first slider position shown in FIG. 3, driver magnet 18 can be oriented to exert a retracting or stabilizing magnetic force 28 on actuator magnet 24, retracting force 28 oriented in a direction away from injection end 14 of hollow guide shell 12. As such, retracting magnetic force 28 can help keep actuator magnet 24 retained towards back end 22 of hollow guide shell 12, or in a retracted position within hollow guide shell 12. In some embodiments, injection device 10 can include a spacer 30 positioned on back end 22 of hollow guide shell 12. When slider member 16 is in the first slider position, driver magnet 18 and retracting magnetic force 28 can help keep actuator magnet 24 maintained in an engaged position against spacer 30.

When slider member 16 moves from the first slider position to the second slider position, as shown in FIG. 6, the magnetic force exerted on actuator magnet 24 by driver magnet 18 can change longitudinal direction, and switch from a retracting magnet force 28 to an injection force 34. Driver magnet 18 can thus exert injection force 34 on actuator magnet 24 once slider member 16 moves from the first slider position to the second slider position, injection force 34 oriented in a direction toward injection end 14 of hollow guide shell 12. Injection force 34 can cause actuator magnet 24, and any components of injecting device 10 attached or coupled thereto, to move toward injection end 14 of hollow guide shell 12 to actuate injection device 10.

Magnetic forces extending toward or away from injection end 14 of hollow guide shell 12 denotes that a longitudinal component, or a component of the magnetic force substantially parallel with the longitudinal axis 20 of hollow guide shell 12, is oriented either toward or away from injection end 14, though the net magnetic force may not be parallel with longitudinal axis 20. As such, retracting magnetic force 28 has a longitudinal component that is directed away from injection end 14, and injection force 34 has a longitudinal component which is directed toward injection end 12.

Injection pin 36 can be coupled to actuator magnet 24, such that once slider member 16 moves from the first slider position to the second slider position, injection pin 36 moves toward injection end 14 of hollow guide shell 12 as driver magnet 18 exerts injection force 34 on actuator magnet 24. In some embodiments, as shown in FIG. 3, injection device 10 can include a cartridge holder 38 positioned at least partially within hollow guide shell 12. Cartridge holder 38 can generally be positioned proximate injection end 14 of hollow guide shell 12. Fluid cartridge 40 can be contained within cartridge holder 38. In different embodiments, the fluid contained in cartridge 40 can be either liquid or gas, or any other suitable injectable substance, depending on the particular application. In some embodiments, the fluid in cartridge 40 can be a desired dosage of a particular medication being delivered or injected into a patient. Cartridge 40 can include a receptacle 42 wherein fluid can be stored, a plunger 44 positioned within receptacle 42, and a needle 46 fluidly communicated with receptacle 42. Needle 46 can be oriented towards injection end 14 of hollow guide shell 12 when cartridge 40 is positioned within cartridge holder 38, and plunger 44 can be oriented toward back end 22 of hollow guide shell 12 relative to the needle and toward injection pin 36.

As injection force 34 is exerted on actuator magnet 24 by driver magnet 18, and actuator magnet 24 moves toward injection end 14 of hollow guide shell 12 in response to injection force 34, injection pin 36 coupled to actuator magnet 24 can extend into cartridge holder 38 and engage cartridge 40, and particularly plunger 44 in some embodiments. In some embodiments, as shown in FIG. 2, cartridge 40 is positioned within cartridge holder 38 initially in a retracted position such that needle 46 of cartridge 40 is contained within cartridge holder 38. In some embodiments, cartridge 40 is retained in the retracted position by friction or interference forces applied by cartridge holder 38 as cartridge 40 is installed in cartridge holder 38. Such friction forces can be designed for and created during manufacturing of the cartridge holder 38 and cartridge 40 such that a friction fit is produced between the two components. In other embodiments, cartridge holder 38 can include cartridge holder injection opening 48 through which needle 46 can be forced. Cartridge holder injection opening 48 can be sized to produce an interference fit with needle 46 such that cartridge 40 is retained in a retracted positioned within cartridge holder 38 until the cartridge is engaged by injection pin 36 and needle 46 is forced through cartridge holder injection opening 48.

Figure 7:
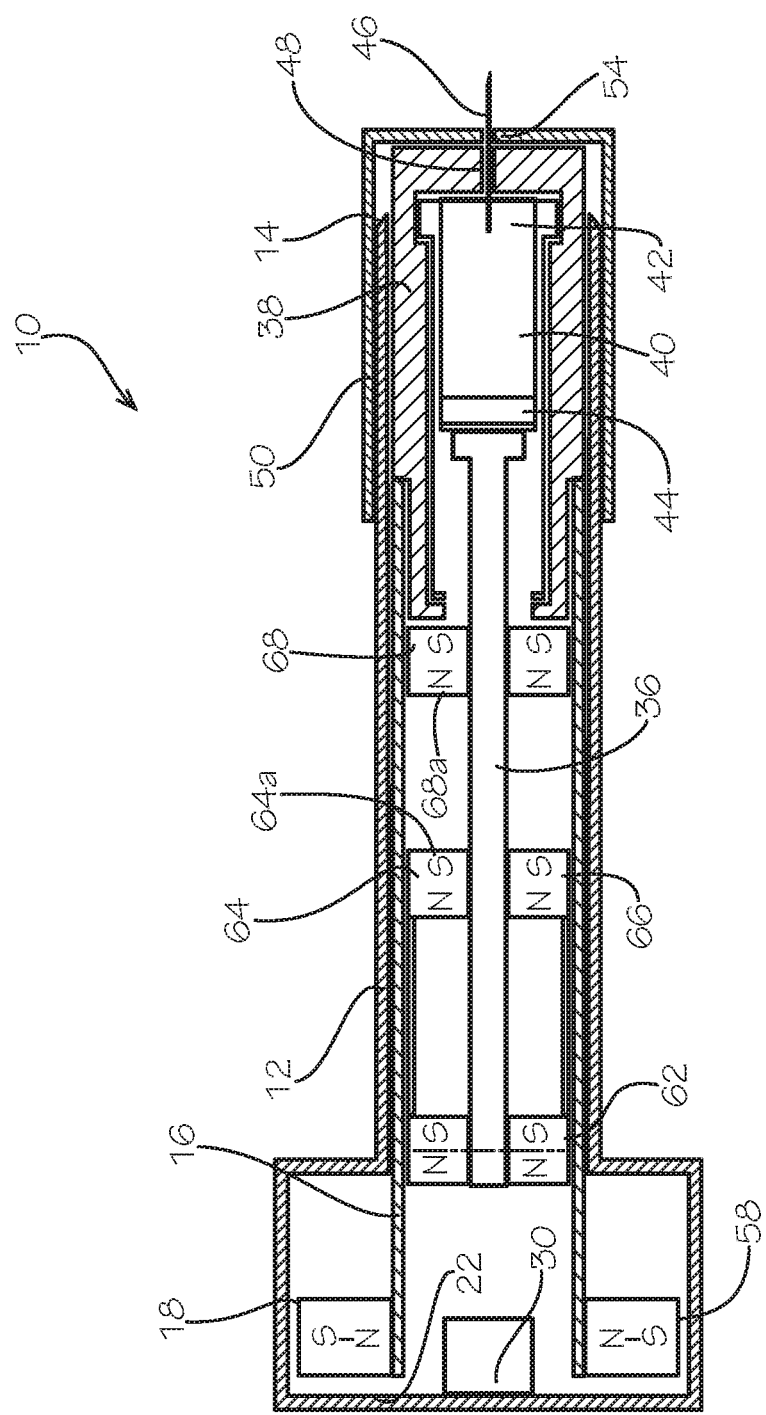
FIG. 7 is a side cross sectional view of the injection device of FIG. 1 showing an actuator magnet moving in a direction toward an injection end of a hollow guide shell in response to a magnetic force exerted by a driver magnet of the device, and an injection pin coupled to the actuator magnet extending into a cartridge holder of the device.
Figure 8:
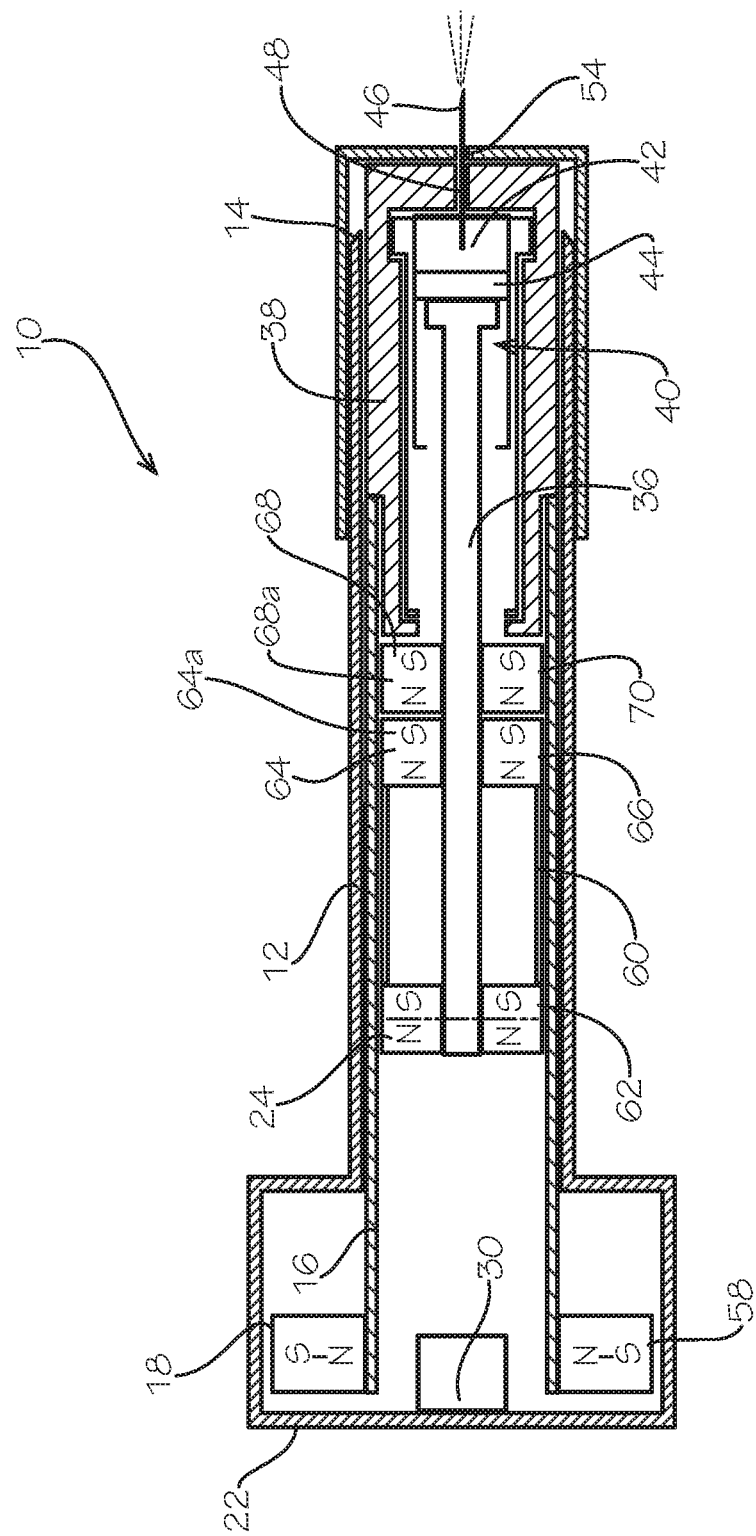
FIG. 8 is a side cross sectional view of the injection device of FIG. 7 showing the injection pin being fully inserted into a cartridge positioned in the cartridge holder to force the contents of the cartridge out of a needle of the cartridge and out of the injection device.

As shown in FIG. 7, as injection pin 36 extends into cartridge holder 38, injection pin 36 can force or push cartridge 40 to overcome the friction forces applied by cartridge holder 38 and on either cartridge 40 or needle 46 and move cartridge 40 within cartridge holder 38 toward injection end 14 such that needle 46 extends out of cartridge holder 38 and injection device 10, and particularly through cartridge holder injection opening 48. Once cartridge 40 reaches and abuts against the front of cartridge holder 38, as shown in FIG. 8, injection pin 36 can push or force plunger 44 further into receptacle 42, thereby forcing the fluid contained in receptacle 42 to be injected or dispensed through needle 46 and into a desired object. As such, slider member 16 moving to the second position and driver magnet 18 exerting injection force 34 on actuator magnet 24 can actuate the injection of fluid contained in cartridge 40 into a desired object.

Figure 10:
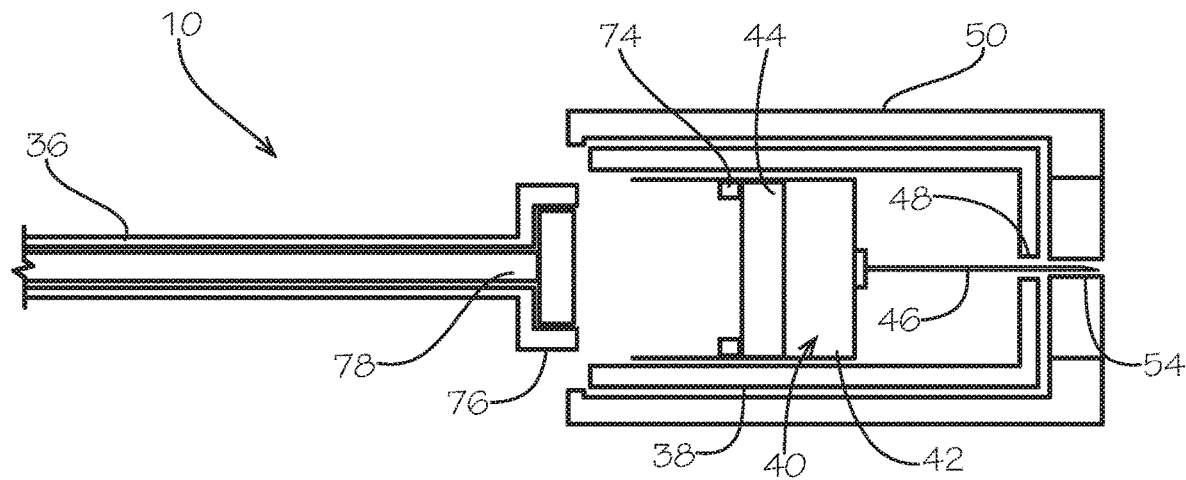
FIG. 10 is a side cross sectional view of another embodiment of an injection pin having an outer pin and an inner pin extendable into the cartridge holder and cartridge of FIG. 9.
Figure 10A:
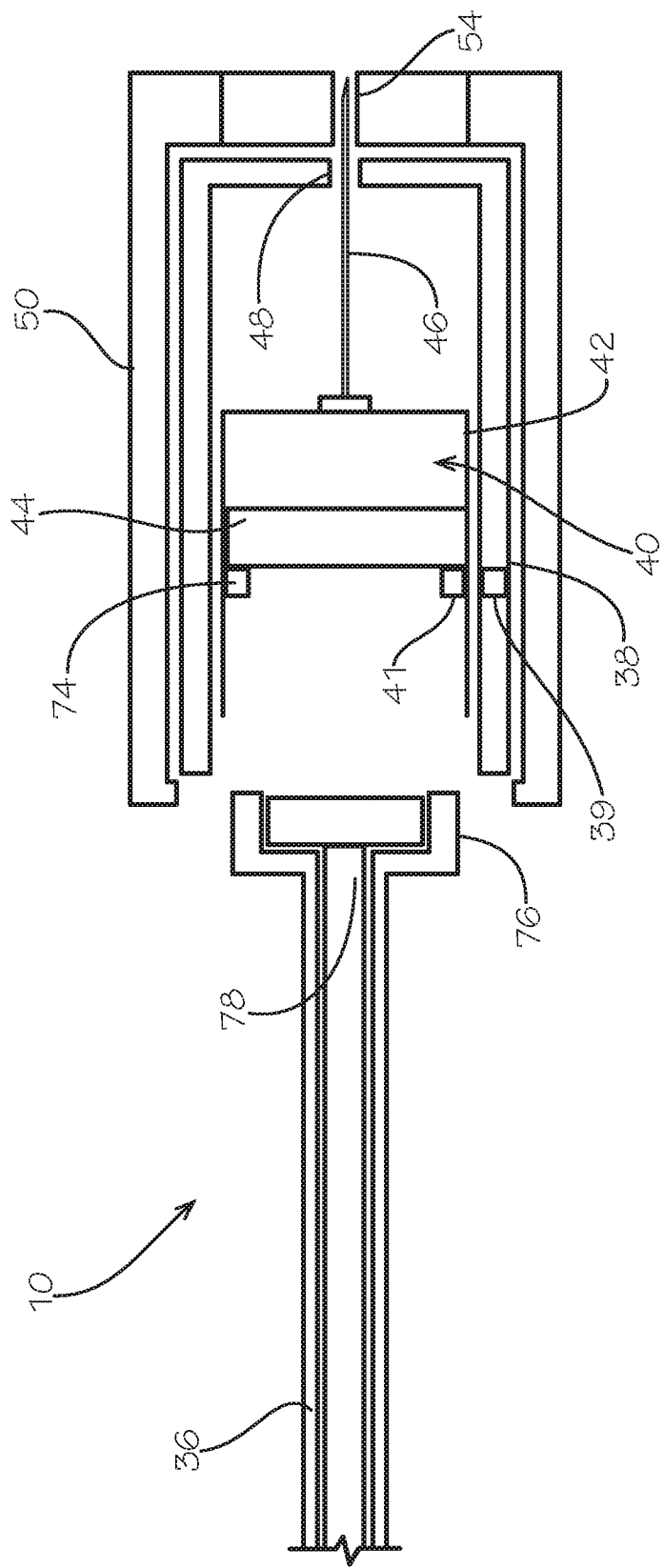
FIG. 10A, is a side cross sectional view of another embodiment of a cartridge of the present disclosure having magnets that correspond to magnets on a cartridge holder to retain the cartridge in a desired position within the cartridge holder prior to actuation of the injection device.

In other embodiments, as shown in FIG. 10a, cartridge holder 38 can include one or more retention magnets 39 and cartridge 40 can include one or more corresponding retention magnets 41. Retention magnets 39 and 41 can be oriented such that as cartridge 40 is inserted into cartridge holder 38, retention magnets 39 and 41 can be attracted to one another to retain cartridge 40 in a desired position within cartridge holder 38 prior to actuation of injection device 10. When injection device 10 is actuated and injection pin 36 extends into cartridge holder 38, injection pin 36 can force or push on cartridge 40 such that needle 46 of cartridge 40 extends out of cartridge holder 38 and injection device 10 and can be inserted into an object such as a patient prior to injection of a fluid from cartridge 40.

Referring again to FIG. 2, in some embodiments, injection device 10 can include an end cap 50. End cap 50 can be movably positioned or slidably disposed on injection end 14 of hollow guide shell 12. End cap 50 can be movable between an extended position, shown in FIG. 2, and a compressed position, shown in FIG. 6. End cap 50 can generally move with respect to hollow guide shell 12 along longitudinal axis 20. End cap 50 can be engaged with, abutting, or disposed against slider member 16, such that as end cap 50 moves on hollow guide shell 12, and particularly as end cap 50 moves from the extended position to the compressed position, end cap 50 can move slider member 16 from the first slider position to the second slider position to actuate injection device 10. End cap 50 can include an end cap aperture 54, end cap aperture 54 oriented to allow passage of needle 46 of cartridge 40 through end cap aperture 54 when injection device 10 is actuated, such that needle 46 can extend into a desired object.

In some embodiments, end cap 50 can be directly engaged with slider member 16. In other embodiments, as shown in FIG. 2, cartridge holder 38 can be positioned between end cap 50 and slider member 16. In such embodiments, end cap 50 can engage slider member 16 via cartridge holder 38 to move slider member 16 from the first slider position to the second slider position.

Figure 4:
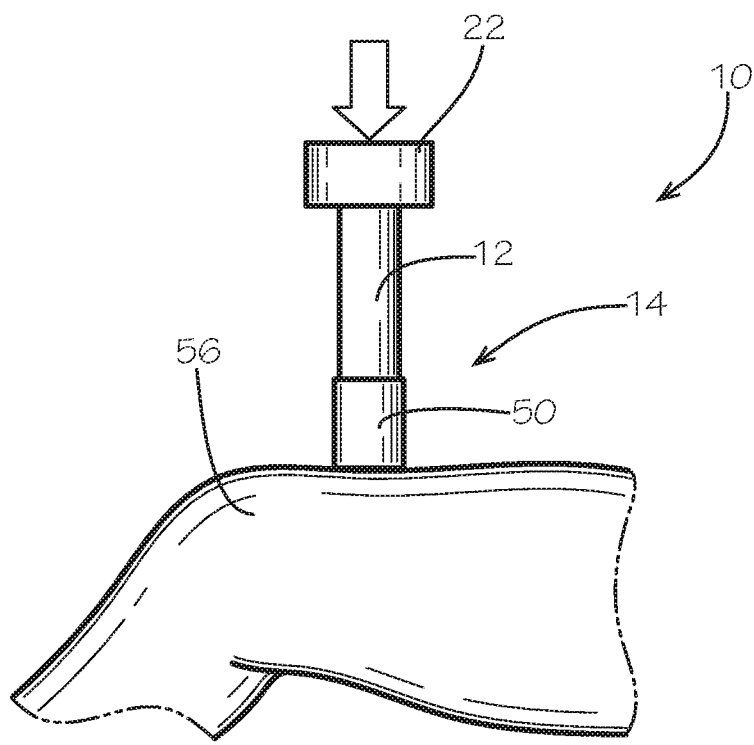
FIG. 4 is a perspective view of the injection device of FIG. 1 being positioned against and pressed toward a user's leg to inject a medication into the user's leg.
Figure 5:
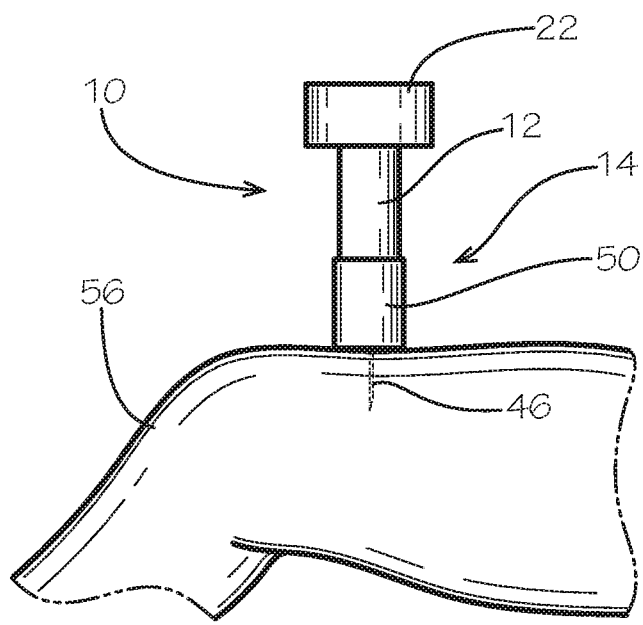
FIG. 5 is a perspective view of the injection device of FIG. 4 in an actuated configuration with a needle of the injection device inserted into the user's leg.

Actuation of injection device 10 by a user is shown in FIGS. 4-5. Injection device 10 and the components contained therein can initially be oriented as shown in FIG. 2, with slider member 16 in the first position and end cap 50 in an extended position. A user can press injection device 10 against a desired object, shown as a patient's leg 56 in FIG. 4, with end cap 50 pressed against the desired object. As injection device 10 is pressed against the desired object, end cap 50 can be moved or compressed to the compressed position, as shown in FIG. 5, end cap 50 moving slider member 16 to the second slider position, as shown in FIG. 6, thereby quickly and conveniently actuating injection device 10.

As such, injection device 10 can be actuated by a user by simply pressing injection device 10 against a desired object. Such an actuation mechanism can be beneficial when it is desirable for injection to occur quickly, or when it is desirable to reduce or minimize the time in which needle 46 is inserted into a desired object. One such instance can occur when medicine or drugs are being delivered to an uneasy patient, such as a child or a patient with a phobia of needles. Injection device 10 can be quickly pressed against the desired area of the patient's body, with actuation of injection device 10 occurring quickly before the patient can move or jerk in response to the injection, such movement potentially affecting the proper delivery of the medicine or drug to the patient. In contrast, the needle of conventional syringes must typically be inserted into an object, and the operator must then adjust the operator's grip on the syringe to manually administer the drug by pressing down on the syringe. A substantial amount of time can lapse between the initial insertion of the needle and the completion of the injection process.

Referring again to FIG. 2, driver magnet 18 can have a first driver magnet pole 18a, a second driver magnet pole 18b, and a driver magnetic axis 18c extending from first driver magnet pole 18a to second driver magnet pole 18b. Actuator magnet 24 can similarly have a first actuator magnet pole 24a, second actuator magnet pole 24b, and actuator magnetic axis 24c extending from first actuator magnetic pole 24a to second actuator magnet pole 24b. Actuator magnet 24 can also include an actuator magnet midline 24d extending between first actuator magnet pole 24a and second actuator magnet pole 24b. Driver magnetic axis 18c can be substantially perpendicular to actuator magnetic axis 24c in some embodiments. In some embodiments, driver magnetic axis 18c and actuator magnet midline 24d can be substantially perpendicular to longitudinal axis 20 of hollow guide shell 12, and actuator magnetic axis 24c can be substantially parallel to longitudinal axis 20 of hollow guide shell 12. Driver magnetic axis 18c and actuator magnetic axis 24c oriented perpendicular to one another can produce the changing or reversing of the direction of the magnetic force exerted on actuator magnet 24 by driver magnet 18 as driver magnet 18 moves from the first slider position to the second slider position, and particularly as first actuator magnet pole 24a crosses driver magnet axis 18c.

For instance, as shown in FIGS. 2 and 6, first driver magnet pole 18a can face or be oriented toward longitudinal axis 20, such that first driver magnet pole 18a produces a dominant magnetic force on actuator magnet 24, compared to second driver magnet pole 18b. As driver magnet 18 moves within hollow guide shell 12 as slider member 16 moves from the first slider position to the second slider position, the interaction of first driver magnet pole 18a with the first and second actuator magnet poles 24a and 24b can change to produce varying magnetic forces on actuator magnet 24.

In some embodiments, first actuator magnetic pole 24a, which corresponds to or is a like pole of first driver magnet pole 18a, can be oriented towards back end 22 of hollow guide shell 12, or in a direction away from injection end 14. When slider member 16 is in the first slider position, driver magnet 18 can be positioned within hollow guide shell 12 such that first driver magnet pole 18a and driver magnetic axis 18c are generally positioned longitudinally between first actuator magnet pole 24a and injection end 14, and more particularly between first and second actuator magnet poles 24a and 24b. As such, a repulsive magnetic force can be produced by first driver magnet pole 18a on corresponding first actuator magnet pole 24a in a direction towards back end 22 of hollow guide shell 12 and away from injection end 14. First driver magnetic pole 18a can additionally exert an attractive force on second actuator magnet pole 24b in a direction toward back end 22 and away from injection end 14. As such, the net retracting force 28 exerted on actuator magnet 24 by driver magnet 18 when slider member 16 is in the first slider position is oriented in a direction towards back end 22 and away from injection end 14.

When slider member 16 moves to the second slider position, driver magnet 18 can be positioned within hollow guide shell 12 such that first driver magnet pole 18a and driver magnetic axis 18c are generally located longitudinally between first actuator magnet pole 24a and back end 22, such that first actuator magnetic pole 24a is between first driver magnetic pole 18a and injection end 14. As such, a repulsive injection force can be produced by first driver magnet pole 18a on corresponding first actuator magnet pole 24a in a direction towards injection end 14 of hollow guide shell 12 that is greater than the attractive force exerted on second actuator magnet pole 24b by first driver magnet pole 18a in a direction away from injection end 14. As such, a net injection force 34 is produced that is directed or oriented towards injection end 14 and away from back end 22 when slider member 16 is moved to the second slider position.

Figure 15:
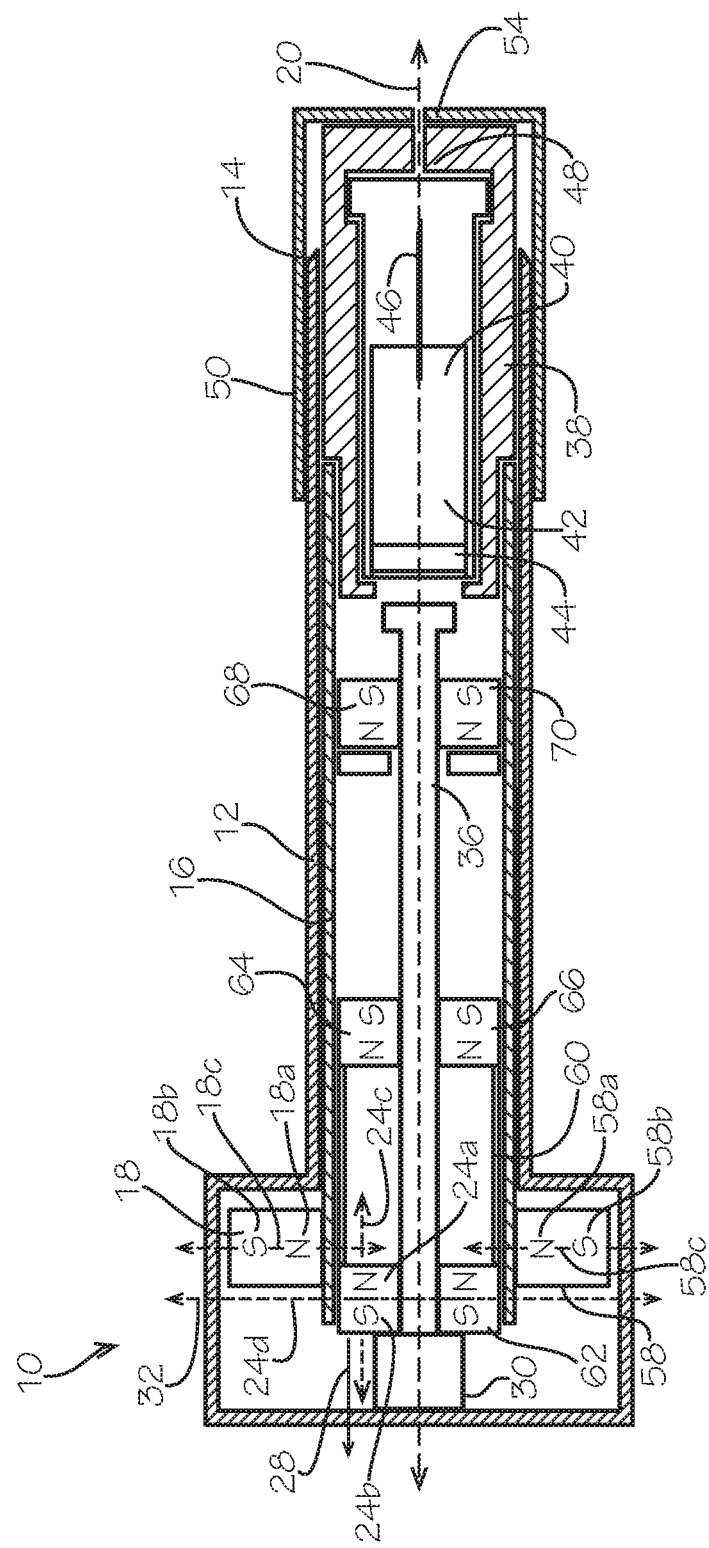
FIG. 15 is a side cross sectional view of the injection device of FIG. 2 wherein the orientation of first and second actuator magnet poles is reversed.

In another embodiment, shown in FIG. 15, first actuator magnet pole 24a corresponding to first driver magnet pole 18a can be oriented towards or facing injection end 14. When slider member 16 is in the first slider position, driver magnet 18 can be positioned such that first driver magnet pole 18a and driver magnetic axis 18c are generally positioned longitudinally between first actuator magnet pole 24a and injection end 14. As such, a repulsive magnetic force can be produced by first driver magnet pole 18a on corresponding first actuator magnet pole 24a in a direction towards back end 22 of hollow guide shell 12 and away from injection end 14 that is greater than the attractive force exerted on second actuator magnet pole 24b by first driver magnet pole 18a in a direction towards injection end 14. As such, a net retracting force 28 is produced that is directed or oriented towards back end 22 and away from injection end 14 when slider member 16 is in the first slider position.

Figure 16:
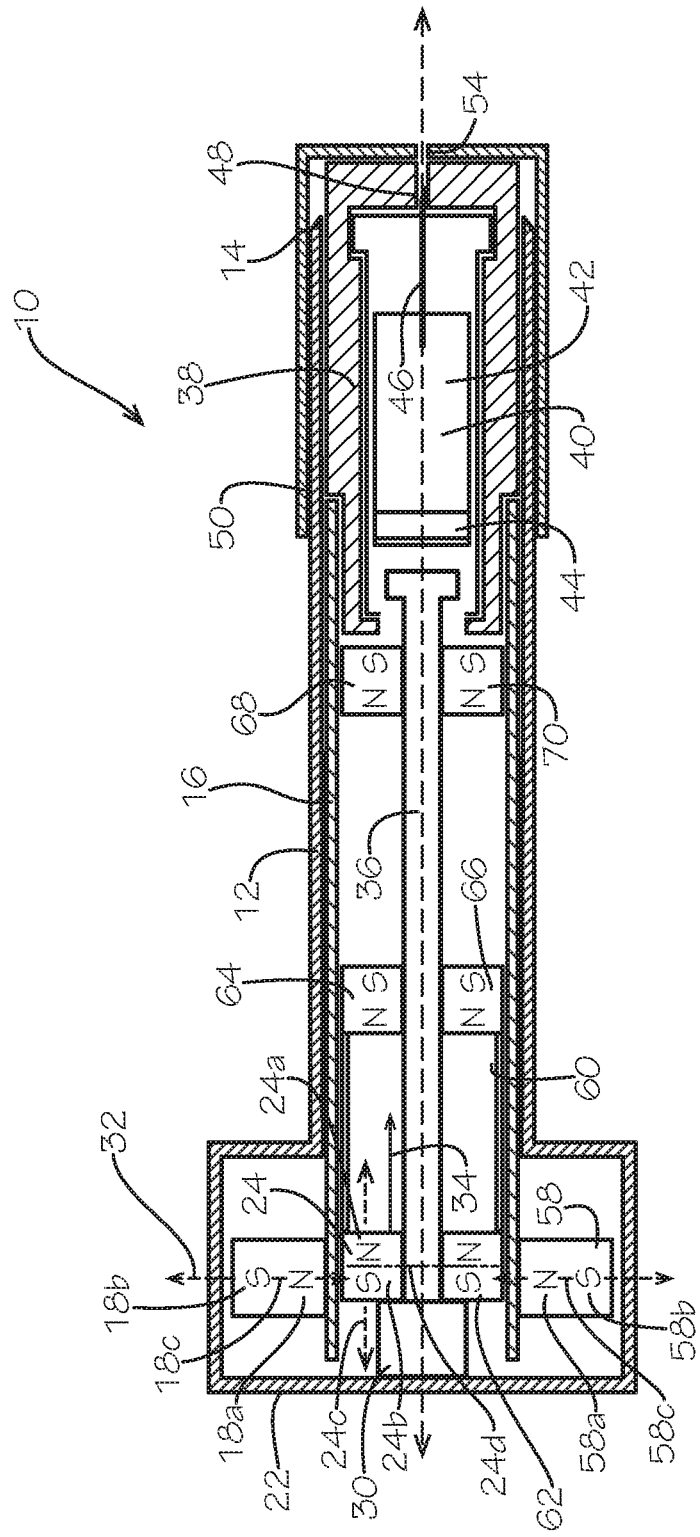
FIG. 16 is a side cross sectional view of the injection device of FIG. 15 with the slider member in the second slider position.

When slider member 16 moves to the second slider position, as shown in FIG. 16, driver magnet 18 can be positioned such that first actuator magnet pole 24a is positioned longitudinally between first driver magnet pole 18a and injection end 14. In some embodiments, first driver magnet pole 18a and driver magnetic axis 18c can be generally located between first and second actuator magnet poles 24a and 24b. As such, a repulsive magnetic force can be produced by first driver magnet pole 18a on corresponding first actuator magnet pole 24a in a direction towards injection end 14 of hollow guide shell 12. First driver magnetic pole 18a can additionally exert an attractive force on second actuator magnet pole 24b in a direction toward injection end 14 and away from back end 22. As such, the net injection force 34 exerted on actuator magnet 24 when slider member 16 is in the second slider position is oriented in a direction towards injection end 14 and away from back end 22.

In some embodiments, as shown in FIG. 2, when slider member 16 is in the first slider position, driver magnetic axis 18c can be positioned longitudinally between actuator magnet midline 24d and injection end 14. When slider member 16 is in the second slider position, as shown in FIG. 6, driver magnetic axis 18c can be positioned between back end 22 and actuator magnet midline 24d.

When slider member 16 moves from the first slider position to the second slider position, as shown in FIG. 6, at least a portion of driver magnet 18 can cross a magnetic shift line 32 as slider member 16 moves from the first slider position to the second slider position. The magnetic force exerted on actuator magnet 24 by driver magnet 18 can change longitudinal direction as a predetermined portion of driver magnet 18 crosses magnetic shift line 32. Magnetic shift line 32 can be determined based on the location of the poles of actuator magnet 24. Magnetic shift line 32 is shown at actuator magnet midline 24a in FIG. 6. In other embodiments, magnetic shift line 32 can be at first actuator magnet pole 24a, such that the magnetic force applied on actuator magnet 24 by driver magnet 18 changes direction after a predetermined portion of driver magnet 18 is positioned behind or rearward of first actuator magnet pole 24a. In some embodiments, the magnetic force exerted on actuator magnet 24 by driver magnet 18 can change or shift directions to actuate injection device 10 when driver magnetic axis 18*c* crosses magnetic shift line 32, or when approximately half of driver magnet 18 crosses magnetic shift line 32. In some embodiments the change in the direction of the magnetic force applied by driver magnet 18 can be described as occurring as driver magnet axis 18*c* is moved to a positioned behind the first actuator magnet pole 24*a*, or when first actuator magnet pole 24*a* crosses driver magnet axis 18*c*.

Magnetic shift line 32 can generally be described as a line oriented perpendicular to longitudinal axis 20 of hollow guide shell 12 where the magnetic force exerted on actuator magnet 24 by driver magnet 18 changes or reverses direction as a predetermined portion of driver magnet 18 crosses magnetic shift line 32. The position of magnetic shift line 32 and the predetermined portion of driver magnet 18 needed to cross magnetic shift line 32 before the magnetic force exerted on actuator magnet 24 by driver magnet 18 can vary in different embodiments depending on the dimensions, positions, and magnetic characteristics of driver magnet 18 and actuator magnet 24.

As shown in FIG. 2, driver magnet 18 can be offset from longitudinal axis 20 such that the magnetic forces applied by driver magnet 18 on actuator magnet 24 can have lateral components in addition to longitudinal components. In some embodiments, injection device 10 can include a second driver magnet 58 disposed on a side of slider member 16 opposite driver magnet 18. Second driver magnet 58 can include a first second driver magnet pole 58*a*, a second second driver magnet pole 58*b*, and a second driver magnetic axis 58*c* extending from the first second driver magnetic pole 58*a* to the second second driver magnet poles 58*b*. First driver magnet pole 18*a* and first second driver magnet pole 58*a* can be like or corresponding poles, and first and second driver magnets 18 and 58 can be positioned symmetrically about longitudinal axis 20 such that driver magnetic axis 18*c* and second driver magnetic axis 58*c* are collinear, with first driver magnet pole 18*a* and first second driver magnet pole 58*a* facing each other in a repulsive interaction. Actuator magnet 24 can be positioned on longitudinal axis 20, such that the lateral components of the magnetic forces exerted on actuator magnet 24 by first and second driver magnets 18 and 58 can substantially offset one another, resulting in a net magnetic force exerted on actuator magnet 24 by first and second driver magnets 18 and 58 that is parallel with longitudinal axis 20. Having first and second driver magnets 18 and 58 positioned symmetrically about longitudinal axis 20 can help suspend or maintain actuator magnet 24, and any components coupled or attached thereto, in a centralized position within hollow guide shell 12 generally along longitudinal axis 20. Having actuator magnet 24 suspended within hollow guide shell 12 by first and second driver magnets 18 and 58 can help reduce any interference or friction produced on actuator magnet 24 by hollow guide shell 12 and/or slider member 12 as actuator magnet 24 and any components attached thereto moves within hollow guide shell 12.

Having driver magnets 18 and 58 positioned symmetrically about hollow guide shell can also help control the actuation energy or trigger energy needed to actuate the device and move slider 16 from the first position to the second position. As driver magnets 18 and 52 are positioned closer and closer to magnetic shift line 32, the magnetic forces exerted on first and second driver magnets 18 and 58 from actuator magnet 24, which can resist motion of the driver magnets 18 and 58 and slider 16, can become more and more lateral in direction. Thus, these resistance forces can substantially offset one another as the driver magnets 18 and 58 approach the magnetic shift line such that the actuation energy needed to overcome these resistance forces can approach zero. The driver magnets 18 and 58 thus approach an equilibrium state as driver magnets 18 and 58 approach magnetic shift line 32, and the retracting magnetic force 28 decreases as driver magnets 18 and 58 move closer to magnetic shift line 32.

Therefore, in some embodiments, the positional relationship between driver magnet 18 and actuator magnet 24 when slider member 16 is in the first slider position can be designed and engineered such that the driver magnet 18 is relatively close to magnetic shift line 32. As such, retracting magnetic force 28 on actuator magnet 24 can be reduced or minimized such that an actuation or trigger force, or a force needed to overcome retracting magnetic force 28 to move driver magnet 18 past magnetic shift line 32 to actuate device 10, can be substantially reduced, especially compared to conventional auto injectors using springs where the triggering force needed to actuate the device is roughly equal to the potential energy stored in the actuation spring, which can be substantial.

For instance, in some embodiments, driver magnets 18 can be designed to store a relatively large potential energy when driver magnet 18 and slider member 16 are in the first slider position, the potential energy stored in driver magnet 18 producing a relatively large injection force 34 on actuator magnet 24 when injection device 10 is actuated and the potential energy is released. In some embodiments, the potential energy stored in driver magnet 18 when released can produce a resultant injection force on actuator magnet 24 of between about 500-2000 pounds. However, because driver magnet 18 can be positioned near magnetic shift line 32 and can be near an equilibrium point within hollow guide shell 12, the amount of actuating force needed to trigger injection device 10 can be greatly minimized, and can theoretically be reduced to a force just above zero pounds. In some embodiments, actuation force can be designed to be between about 0.0001 ounces and 10 pounds. In some embodiments, the actuation force required can be less than or equal to 5 pounds. Once the actuation force is applied however the potential energy of driver magnet 18 can be released to apply the larger injection magnetic force previously described.

In contrast, in conventional spring biased auto injection devices, and particularly Epipen® style auto injection devices currently on the market, the drive springs must be further compressed to actuate the devices and release the potential energy stored in the spring to drive the injection mechanism. As such, the user must overcome the stored potential energy of current devices in order to actuate the device, such that the actuation force is greater than or equal to the driving force produced by the spring once released. The magnetic driver configuration of the present disclosure can therefore help provide similar drive forces as auto injectors currently on the market while reducing the force necessary to actuate injection device 10 when compared to conventional auto injection devices. This can help make an injection process easier and more efficient as less actuation force is required.

Referring again to FIGS. 2 and 6, spacer 30 can help ensure that driver magnet 18 can move to a position as slider member 16 moves to the second slider position such that the magnetic force exerted on actuator magnet 24 by driver magnet 18 can reverse or change longitudinal directions to actuate injection device 10. When slider member 16 is in the first slider position, driver magnet 18 exerts a retracting magnetic force 28 on actuator magnet 24 which can force actuator magnet 24 against spacer 30. Spacer 30 can offset actuator magnet 24 from back end 22 of hollow guide shell 12 such that when end cap 50 is compressed and slider member 16 moves to the second position, the force applied to end cap 50 can overcome the repulsive magnetic forces between driver magnet 18 and actuator magnet 24 such that a predetermined portion of driver magnet 18 can cross magnetic shift line 32 and be positioned generally longitudinally between first actuator magnet pole 24a and back end 22 to produce injection force 34 in a direction towards injection end 14.

Figure 2A:
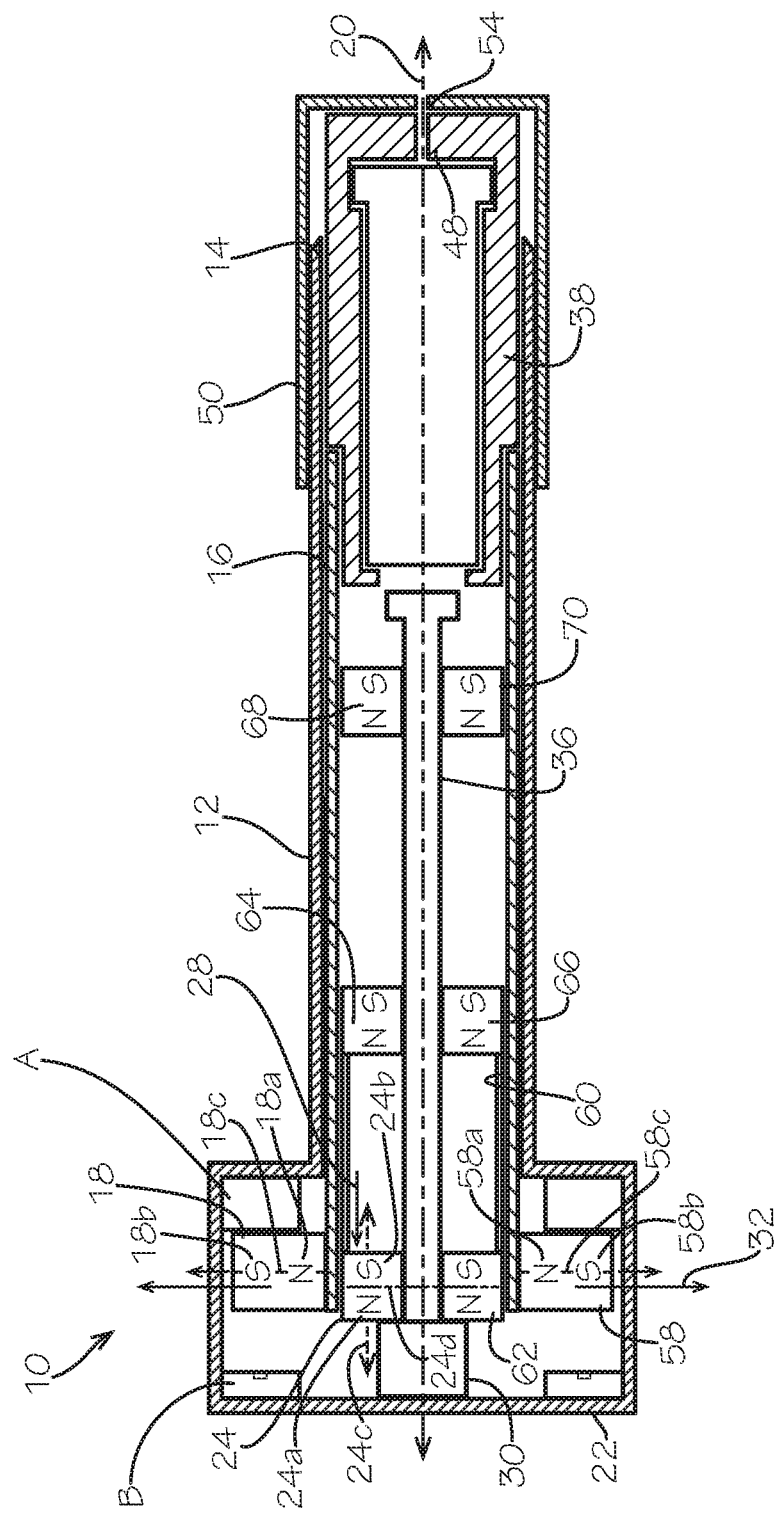
FIG. 2A shows a side cross sectional view of another embodiment of an injection device of the present disclosure having a plurality of driver magnet stops.
Figure 2B:
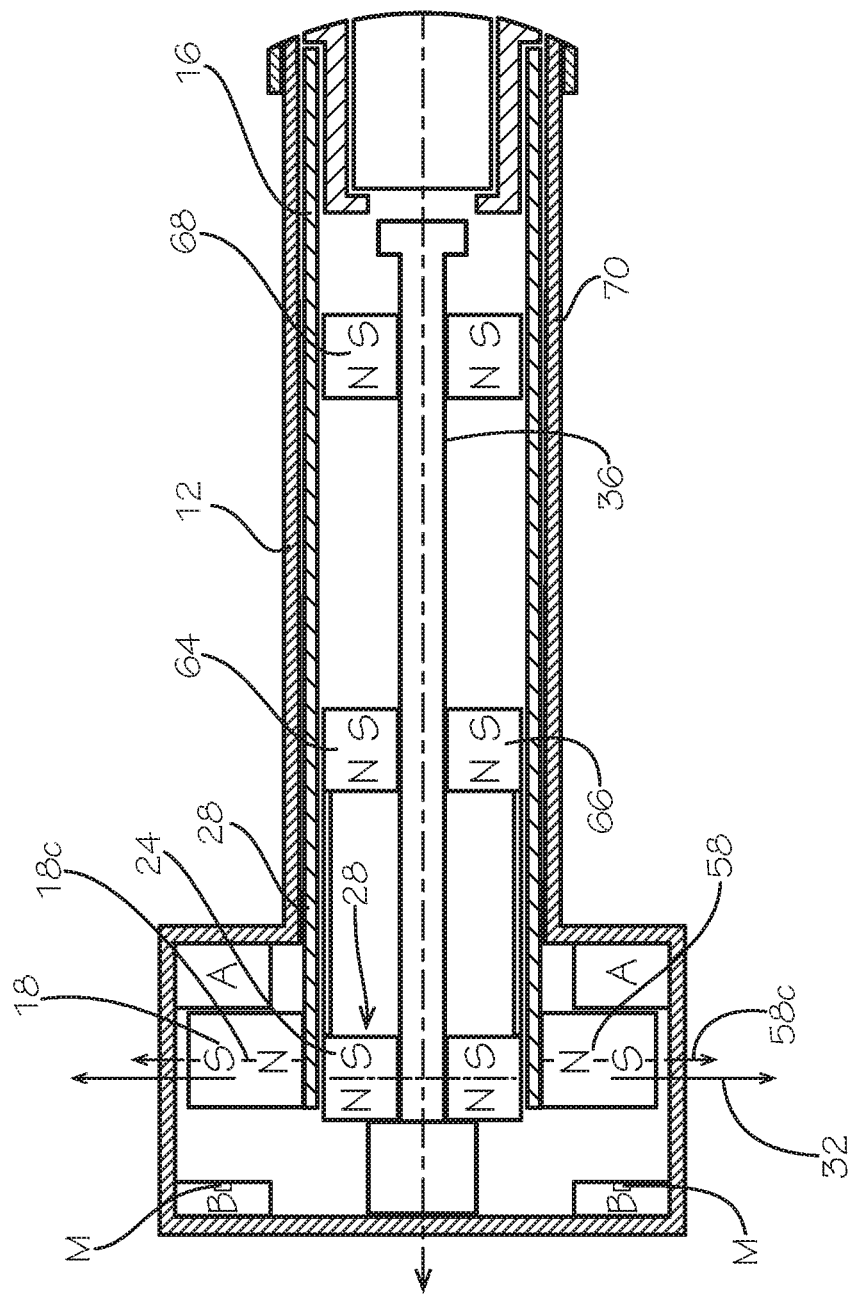
FIG. 2B is a detailed side cross sectional view of the embodiment of FIG. 2A.

In some embodiments, as shown in FIGS. 2A-2B, injection device 10 can include one or more driver magnet stops A and B which can limit the movement of driver magnet 18 before and after actuation. Stop A can limit the movement of driver magnet 18 in a direction toward injection end 14 when slider member 16 is in the first slider position. Driver magnet 18 can be stabilized against stop A by the repulsive field resulting between driver magnet 18 and actuator magnet 24 when driver magnet 18 is in the first slider position. When injection device 10 is actuated and slider member 16 moves to the second slider position, and driver magnet 18 exerts an actuating force on actuator magnet 24, driver magnet 18 can be stabilized against stop B, stop B limiting the movement of driver magnet 18 in a direction away from injection end 14. In some embodiments, driver magnet 18 can meet stop B at a position just rearward from the magnetic shift line 32. As such, driver magnet 18 can be allowed to cross magnetic shift line 32 to actuate device 10, while stop B can help prevent driver magnet 18 from moving further away from injection end 14 within hollow guide shell 12 to help maximize the injection force 34 exerted by driver magnet 18 on actuator magnet 24 during the injection. In some embodiments including multiple driver magnets, injection device 10 can include multiple pairs of stops A and B, and each pair of stops A and B can be associated with a corresponding driver magnet. In some embodiments, stops B can have metal inserts M which can stabilize driver magnets 18 and 24 against stops B in a post-activation state when slider member 16 is in the second slider position. Stops B can be generally made of a non-magnetic material, with metal inserts M being the only magnetic material within stops B.

Figure 14:
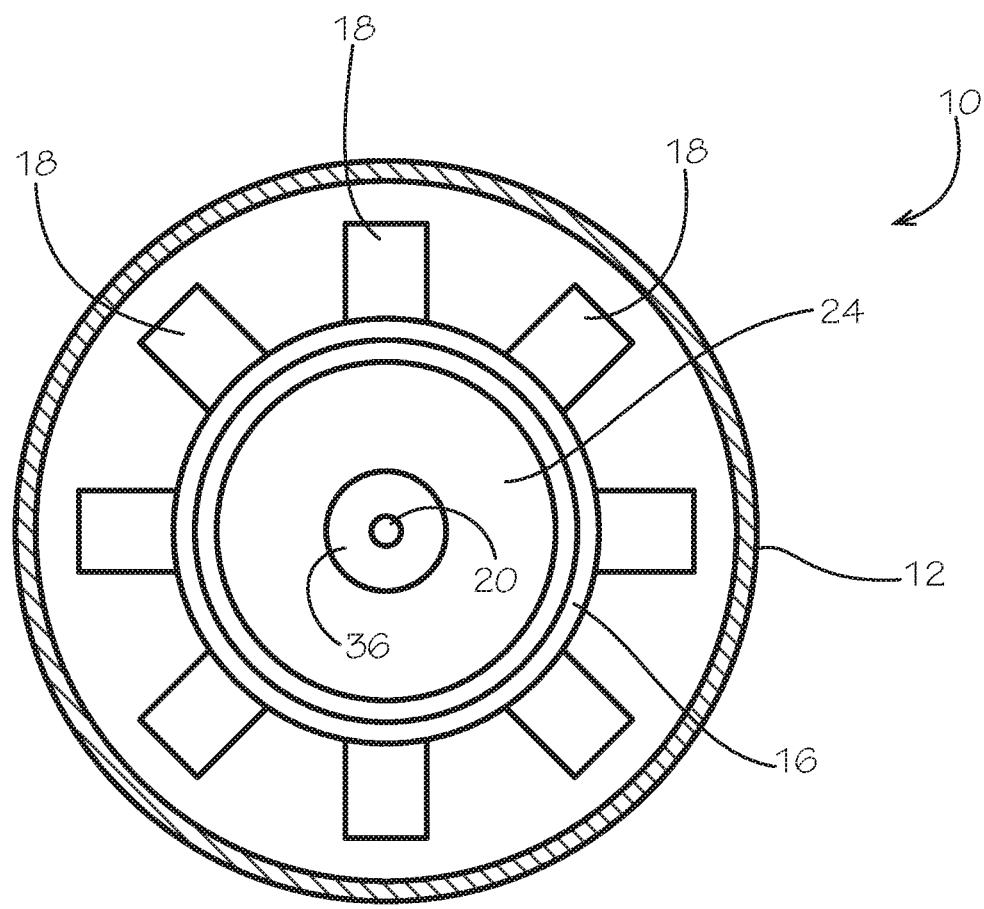
FIG. 14 is a back cross sectional view of another embodiment of an injection device including a plurality of driver magnets spaced radially on a slider member about a longitudinal axis of the injection device, and a plurality of actuator magnets space radially about an injection pin of the injection device.

In some embodiments, as shown in FIGS. 2 and 6-8, injection device 10 can include a carrier frame 60 positioned in hollow guide shell 12. Actuator magnet 24 can be positioned on or coupled to carrier frame 60. Injection pin 36 can be coupled to carrier frame 60 via actuator magnet 24. In some embodiments, injection device 10 can include a second actuator magnet 62 also coupled to carrier frame 60, first and second actuator magnets 24 and 62 having the same polar orientation and positioned symmetrically on opposing sides of injection pin 36, injection pin 36 coupled to carrier frame 60 via first and second actuator magnets 24 and 62. In some embodiments, carrier frame 60 can be sized to fit within opposing sides of slider member 16 such that carrier frame 60 can slide within hollow guide shell 12 and slider member 16 as driver magnets 18 and 58 exert forces on actuator magnets 24 and 62. Having injection pin 36 coupled between two actuator magnets 24 and 62 on a carrier frame 60 can help stabilize injection pin 36 and maintain injection pin 36 in an orientation parallel to longitudinal axis 20, injection pin 36 generally moving along longitudinal axis 20 as driver magnets 18 and 58 exert injection forces 34 on actuator magnets 24 and 62. In other embodiments, actuator magnet 24 can be a circular ring magnet, as shown in FIG. 14. Injection pin 36 can be inserted through a center of the circular ring actuator magnet 24. Having a circular ring actuator magnet 24 can also help balance magnetic forces exerted by first and second driver magnets 18 and 58 on actuator magnet 24.

In some embodiments, injection device 10 can further include one or more carrier magnets 64 and 66 coupled to carrier frame 60. In some embodiments, a first carrier magnet 64 can be positioned on carrier frame 60 between first actuator magnet 24 and injection end 14, and second carrier magnet 66 can be positioned between second actuator magnet 62 and injection end 14. Carrier magnets 64 and 66 can be additionally coupled to injection pin 36 such that carrier magnets 64 and 66 provide a second point of support along injection pin 36 to further stabilize injection pin 36 within hollow guide shell 12. In some embodiments, actuator magnet 24 and a carrier magnet 64 can both be circular ring magnets, injection pin 36 extending through and coupled to a central portion of both actuator magnet 24 and carrier magnet 64.

Figure 13:
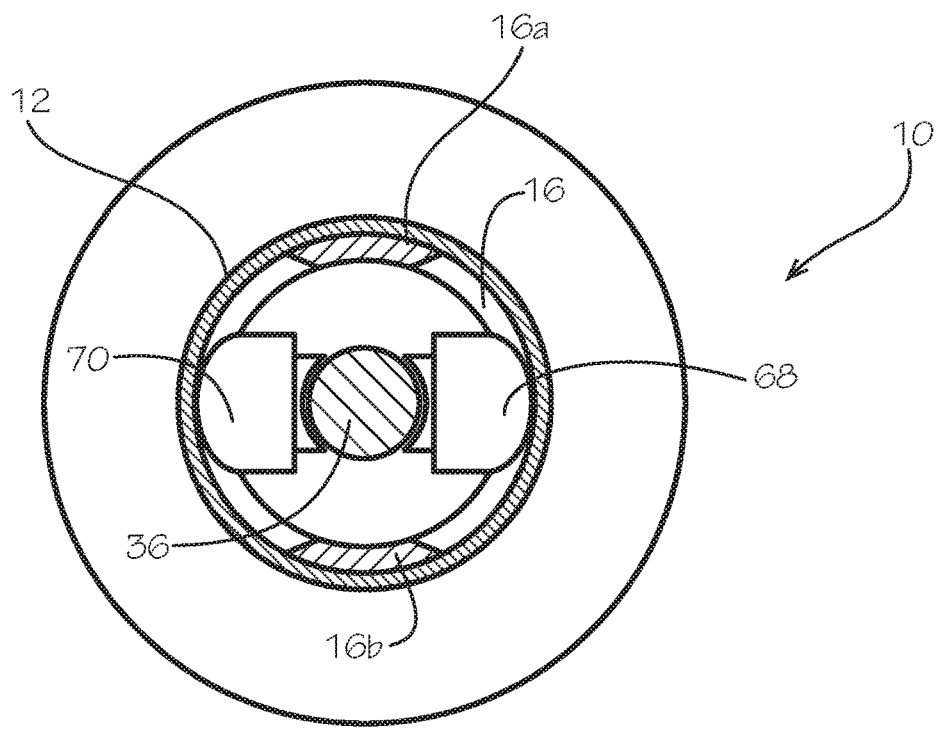
FIG. 13 is a front cross sectional view of another embodiment of an injection device showing one or more fingers of a slider member of the injection device extending around fixed magnets secured to a hollow guide shell of the injection device.
Figure 17:
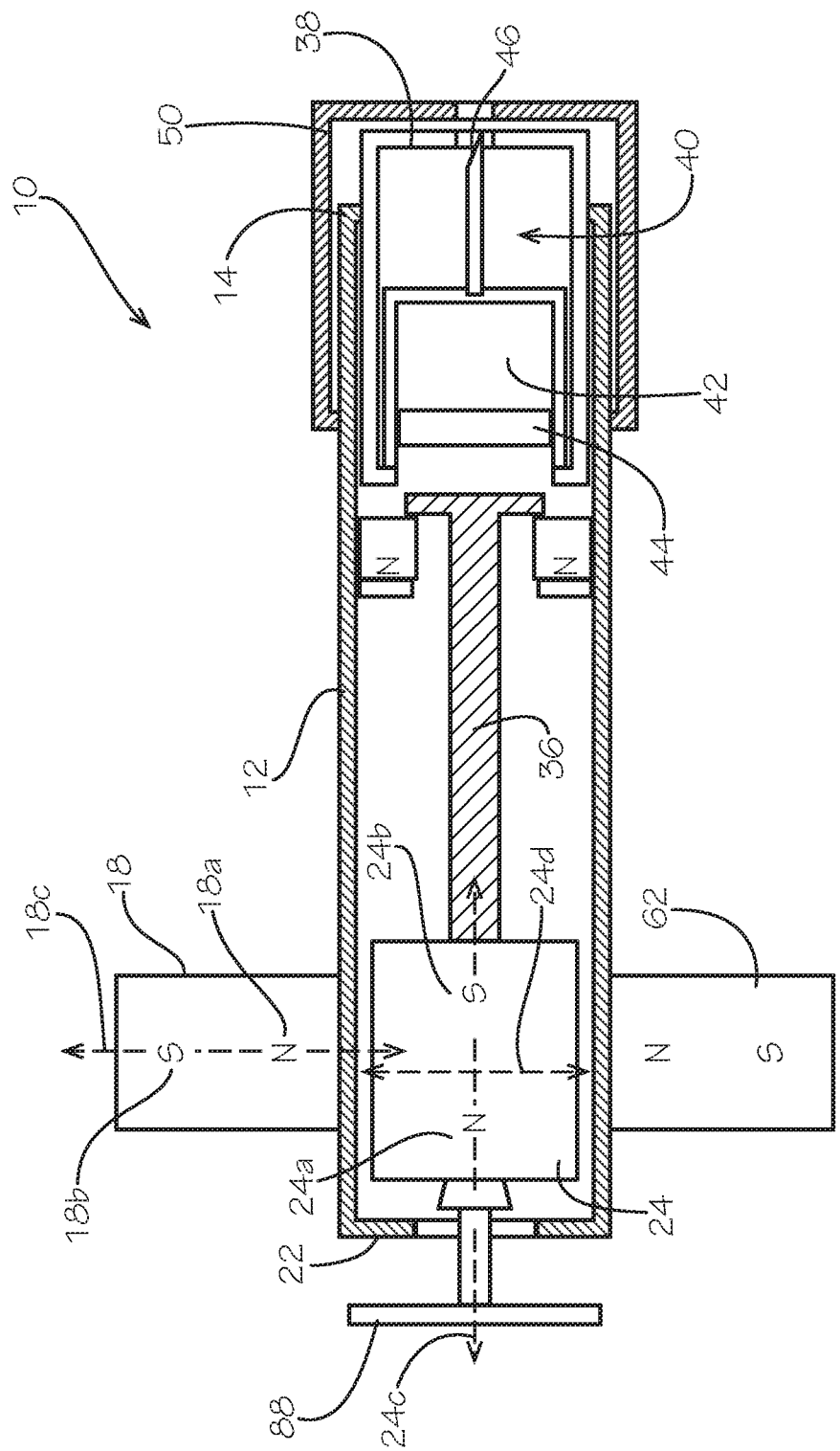
FIG. 17 is a side cross sectional view of another embodiment of an injection device of the present disclosure wherein the actuator magnet is moved to actuate the device.

In some embodiments, as shown in FIGS. 2, 13, and 17, injection device 10 can include one or more fixed magnets 68 and 70. In some embodiments, a first fixed magnet 68 can be positioned between first actuator magnet 24 or first carrier magnet 64 and injection end 14. Fixed magnet 68 can be oriented such that fixed magnet 68 exerts an attractive magnetic force on either first actuator magnet 24 or first carrier magnet 64 in a direction towards injection end 14. As shown in FIG. 4, actuator magnet 24 can have a second pole 24b and/or carrier magnet 64 can have a first carrier magnet pole 64a, and fixed magnet 68 can have first fixed magnet pole 68a. Second actuator magnet pole 24b and/or first carrier magnet pole 64a and first fixed magnet pole 68a can be oriented facing one another and can be unlike or opposite poles such that second actuator magnet pole 24b and/or first carrier magnet pole 64a are attracted to first fixed magnet pole 68a. As such, fixed magnet 68 provide a supplemental injection force in the direction of the injection end 14 as fixed magnet 68 can attract actuator magnet 24 or carrier magnet 64 to fixed magnet 68. Fixed magnet 68 can therefore be considered an auxiliary drive magnet.

In some embodiments, injection device 10 can further include second actuator magnet 62 and/or second carrier magnet 66 and second fixed magnet 70 having a similar orientation, second fixed magnet 70 exerting an attractive magnetic force on second actuator magnet 62 and/or second carrier magnet 66. As such, when slider member 16 moves to the second slider position and driver magnet 18 exerts an injection force 34 on actuator magnet 24, carrier frame 60 moves toward fixed magnets 68 and 70, such that fixed magnets 68 and 70 exert attractive magnetic forces on actuator magnets 24 and 62 and/or carrier magnets 64 and 66, respectively, in a direction toward injection end 14, to help ensure that injection pin 36 is fully inserted into cartridge holder 38 and that the fluid contained in cartridge 40 is properly and fully injected from needle 46 into a desired object. In some embodiments, actuator magnet 24, a carrier magnet 64, and a fixed magnet 68 can all be circular ring or cylinder shaped magnets that are oriented and interact with one another as described above.

As shown in FIG. 13, fixed magnets 68 and 70 can be secured to hollow guide shell 12 such that fixed magnets 68 and 70 do not move during actuation of injection device 10. In some embodiments, slider member 16 can have one or more fingers 16a and 16b which can extend between and around fixed magnets 68 and 70 such that fixed magnets 68 and 70 do not interfere with the movement of slider member 16 between the first slider position and the second slider position. The end cap can engage the fingers 16a and 16b to move slider member 16 between the first and second slider positions. Slider member 16 in some embodiments can also be described as having one or more fixed magnet channels defined in the slider member 16, the fixed magnet channels receiving fixed magnets 68 and 70 as slider member 16 moves relative to hollow guide shell 12.

In high energy applications, for instance for mechanical systems that require a large driving injection force, strong driver magnets 18 and 58 and/or strong fixed or auxiliary drive magnets 68 and 70 can be used to provide the necessary injection force needed. In such instances, the magnetic forces between driver magnets 18 and 58 and actuator magnets 24 and 62 and/or carrier magnets 64 and 66 can cause actuator magnets 24 and 62 and/or carrier magnets 64 and 66 to move toward fixed magnets 68 and 70 at a very fast speed and with a large amount of force. If actuator magnets 24 and 62 and/or carrier magnets 64 and 66 were to be driven directly into fixed magnets 68 and 70, the impact could cause significant damage to one or more of actuator magnets 24 and 62, carrier magnets 64 and 66, and fixed magnets 68 and 70.

To help prevent such damage to the magnets of the system, in some embodiments one or more impact cushions 71 can be positioned between fixed magnets 68 and 70 and back end 22, as shown in FIG. 3. Impact cushions 71 can be connected to the fixed magnets 68 and 70 themselves or to hollow guide shell 12 or slider member 16. After actuation of device 10, as injection force 34 is applied to actuator magnets 24 and 62 and actuator magnets 24 and 62 move toward injection end 14, either actuator magnets 24 and 62 or carrier magnets 64 and 66 can be driven into impact cushions 71. Impact cushions 71 can be made of foam, gel, or other cushioning material that can help disperse the impact force as actuator magnets 24 and 62 are driven toward injection end 14, which can help reduce damage to the magnets of the drive system.

Figure 34:
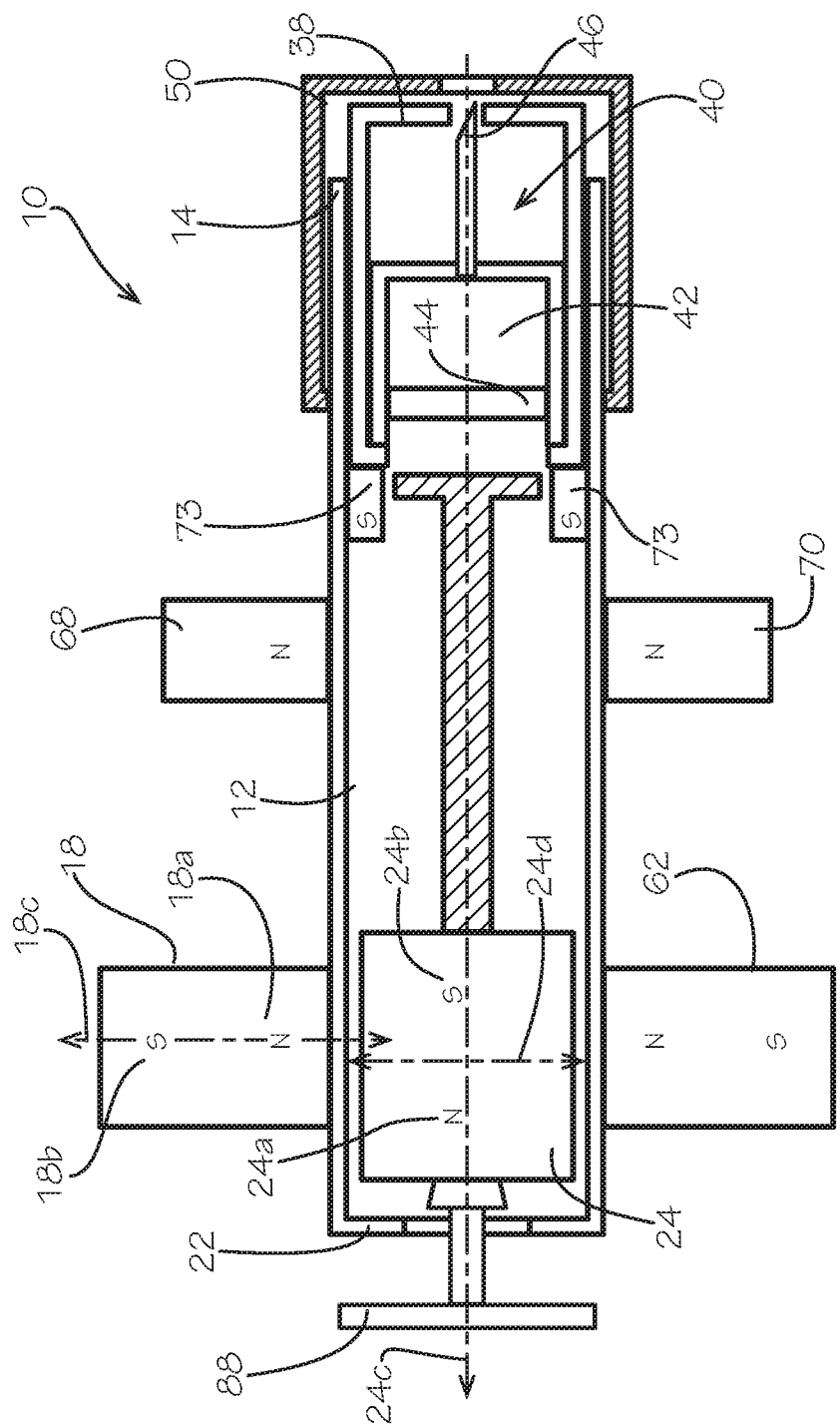
FIG. 34 is a cross sectional view of another embodiment of an injection device having auxiliary drive magnets and repulse stop magnets.

In some embodiments, auxiliary drive magnets 68 and 70 can be positioned within hollow guide shell 12. In other embodiments, as shown in FIG. 34, auxiliary drive magnets 68 and 70 can be positioned on an exterior surface of hollow guide shell 12. The auxiliary drive magnets 68 and 70 can be oriented to produce an attractive force on the auxiliary magnet 24 as the auxiliary magnet 24 approaches the auxiliary drive magnets 68 and 70. In FIG. 34, the north poles of the auxiliary drive magnets 68 and 70 are oriented toward hollow guide shell 12 to produce an attractive force on the forward south second actuator magnet pole 24b.

Having auxiliary drive magnets 68 and 70 positioned on an exterior of hollow guide shell 12 can help prevent actuator magnet 24 from colliding with auxiliary drive magnets 68 and 70, potentially damaging the magnets. An added benefit of having auxiliary drive magnets 68 and 70 on an exterior of hollow guide shell 12 is that the motion of actuator magnet 24 can be slowed or stopped at a desired position within hollow guide shell 12 by auxiliary drive magnets 68 and 70 without the magnets having to collide with one another. As actuator magnet 24 approaches auxiliary drive magnets 68 and 70, the attraction of the north poles of auxiliary drive magnets 68 and 70 with the south pole of actuator magnet 24 will tend to cause south pole of actuator magnet 24 to stop generally between auxiliary drive magnets 68 and 70. As such, the position of auxiliary drive magnets 68 and 70 can be designed for to produce a desired stop point for actuator magnet 24 and thus injection pin 36.

In some embodiments, Injection device 10 can also include one or more repulse stop magnets 73 positioned either within hollow guide shell, as shown in FIG. 34, or on an exterior surface of hollow guide shell 12. In FIG. 34, the south poles of repulse stop magnets 73 are oriented toward the back end 22 of hollow guide shell 12 such that repulse stop magnets 73 produce a repulsive stopping force on the south second actuator magnet pole 24b as actuator magnet 24 approaches repulse stop magnets 73. Repulse stop magnets 73 can help prevent actuator magnet 24 from colliding either with repulse stop magnets 73 or another component of injection device 10 within injection end 14 of device 10, thus helping prevent damage to the internal components of device 10. In some embodiments, device 10 can include both auxiliary drive magnets 68 and 70 as well as repulse stop magnets 73 to both provide an increased driving function as well as a sufficient repulsive stopping force on actuator magnet 24.

Figure 12:
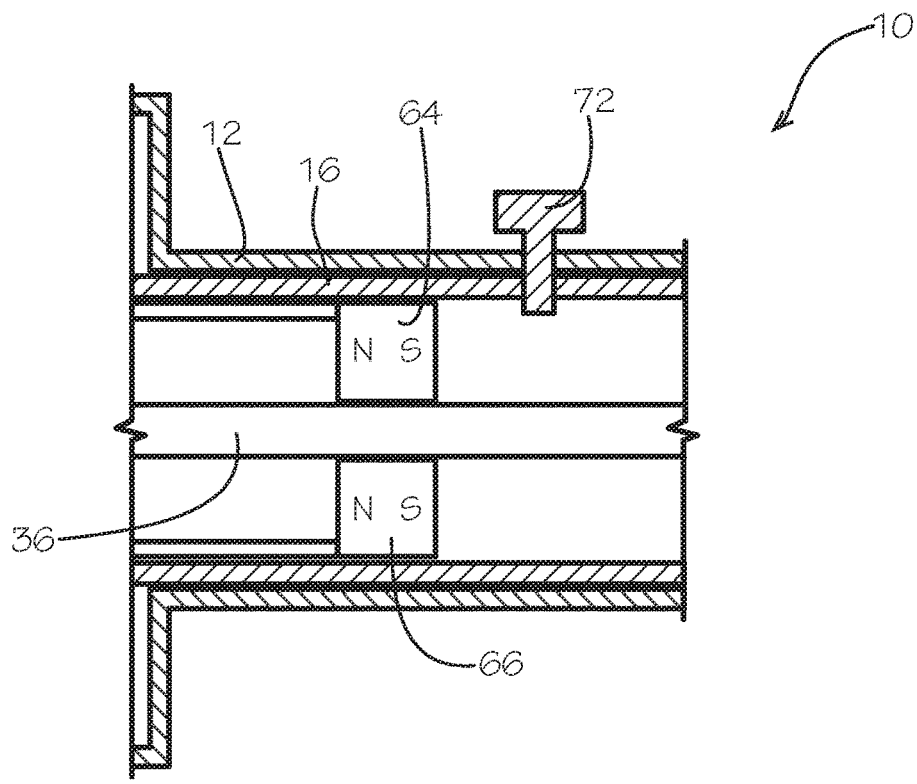
FIG. 12 is a partial side cross sectional view of another embodiment of an injection device including a retention member operable to retain a slider member of the device in a first slider position.

In some embodiments, injection device 10 can further include a retention member 72 operable to retain slider member 16 in the first slider position, as shown in FIG. 12. In some embodiments, hollow guide shell 12 and slider member 16 can include corresponding retention holes which can align with one another when slider member 16 is in the first slider position. Retention member 72 can be a bolt, screw, peg, insert, etc. which can be inserted through the corresponding retention holes in hollow guide shell 12 and slider member 16 to retain slider member 16 in the first slider position. In some embodiments, the retention holes and the retention member 72 can have corresponding threads which can engage one another as retention member 72 is inserted into the retention holes. In other embodiments, retention member 72 can produce a friction fit with the retention holes in slider member 16 and hollow guide shell 12 when retention member 72 is inserted into the retention holes to secure slider member 16 in the first slider position.

Securing or locking slider member 16 in the first slider position can help prevent premature or unwanted actuation of injection device 10. Premature or unwanted actuation can produce an unnecessary and inadvertent needle stick into a user or into another item, and can discharge and waste the contents of injection device 10. For instance, if injection device 10 is placed in a user's pocket, purse, luggage, backpack, etc., unintended forces can be applied to injection device 10, and particularly to the end cap, as injection device 10 is carried around. Such forces can unintentionally actuate injection device 10 if slider member 16 is not locked or retained in the first slider position. Retention member 72 can stop the undesirable external forces from unintentionally actuating injection device 10. Retention member 72 can be removed when injection device 10 is ready to be used. It will be understood by those in the art that various other retention or locking mechanisms can be employed between hollow guide shell 12 and slider member 16 to secure slider member 16 in a first slider position to prevent unwanted actuator of injection device 10.

Figure 9:
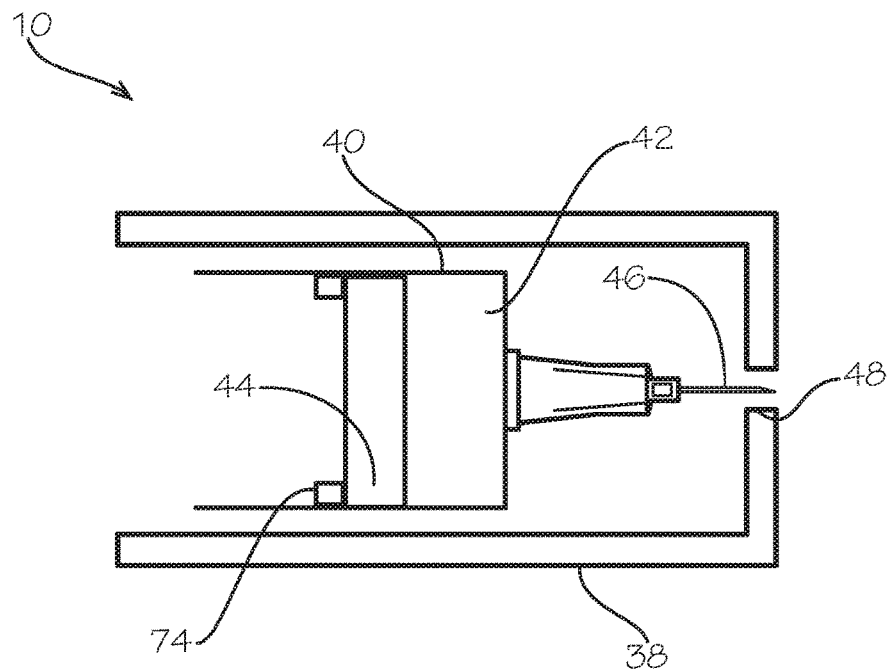
FIG. 9 is a side cross sectional view of another embodiment of a cartridge holder and a cartridge positioned within the cartridge holder, the cartridge having one or more injection needle stops positioned within a receptacle of the cartridge.
Figure 11:
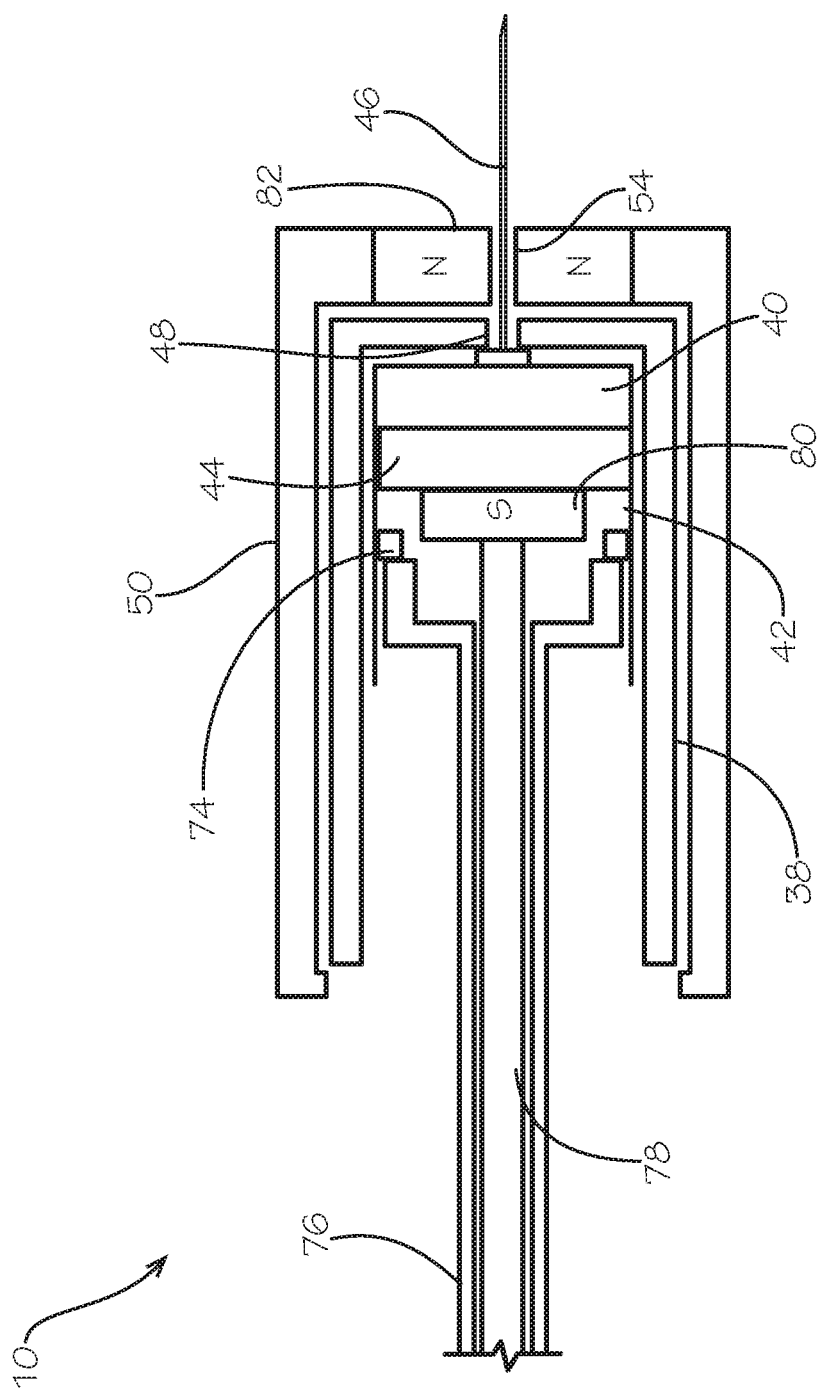
FIG. 11 is a side cross sectional view of the outer pin of the injection pin of FIG. 10 engaging the injection needle stops of the cartridge, and the inner pin of the injection pin engaging a plunger positioned in the receptacle of the cartridge.

In some embodiments, as shown in FIGS. 9-11, cartridge 40 can include one or more injection pin stops 74 positioned in receptacle 42. Plunger 44 can be positioned between injection pin stops 74 and needle 46. Injection pin 36 in some embodiments can include an outer pin 76 and an inner pin 78. As injection pin 36 extends into cartridge holder 38 when injection device 10 is actuated, outer pin 76 can engage injection pin stops 74 to push cartridge 40 such that needle 46 fully extends out of cartridge holder 38 and end cap 50. Once cartridge 40 abuts cartridge holder 38, inner pin 78 can force plunger 44 towards needle 46 to inject fluid contained in receptacle 42 through needle 46 and into the desired object. In some embodiments, inner pin 78 can have an inner pin magnet 80 located on a distal end of inner pin 78, and end cap 50 can have an end cap magnet 82. Inner pin magnet 80 and end cap magnet 82 can be oriented to attract to one another as inner pin 78 approaches end cap 50. Inner pin magnet 80 and end cap magnet 82 can help ensure that inner pin 78 fully deploys into cartridge 40 once cartridge 40 abuts cartridge holder 38 and the longitudinal movement of outer pin 76 is stopped.

Figure 11A:
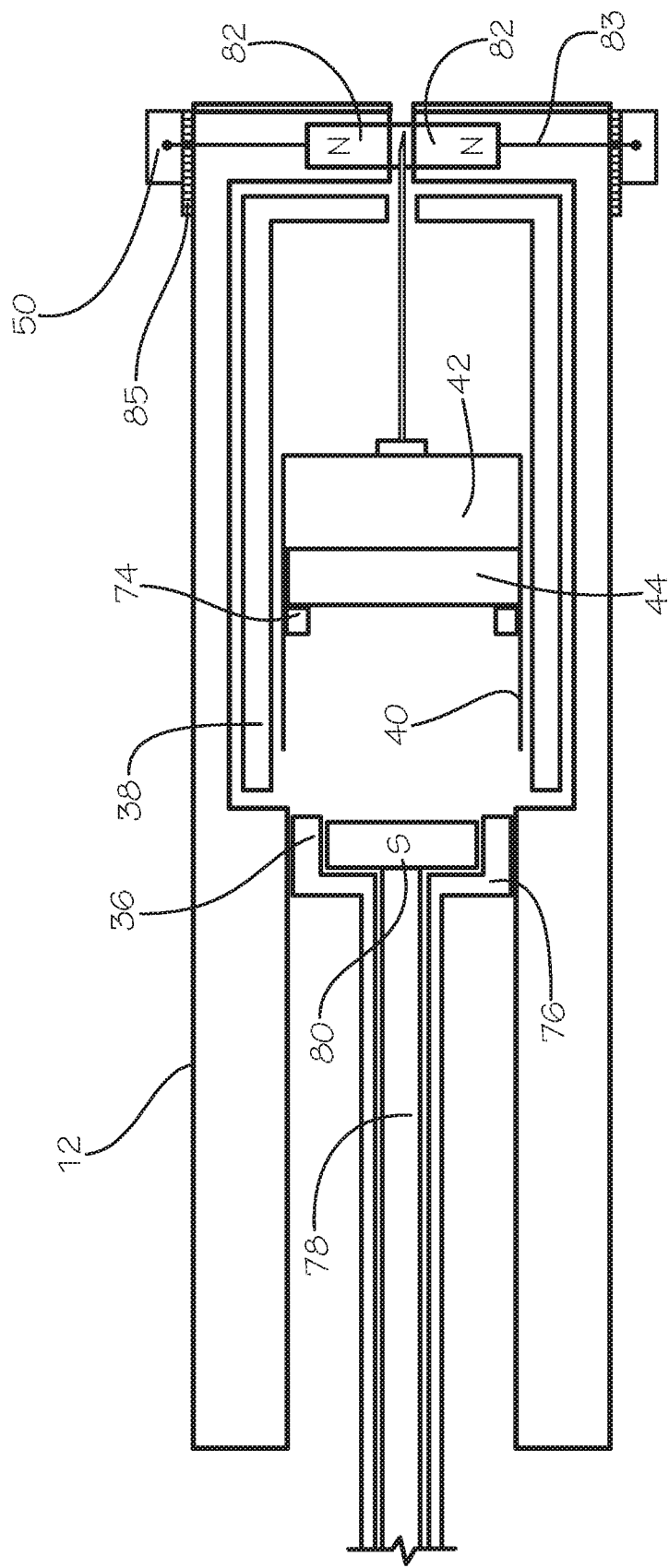
FIG. 11A is a side cross sectional view of the embodiment of FIG. 11 wherein the position of the end cap magnets are adjustable with respect to the hollow guide shell.

In some embodiments, as shown in FIG. 11a, the position of end cap 50 and end cap magnet 82 with respect to hollow guide shell 12 can be movable or adjustable. End cap magnet 82 can be suspended from end cap 50 via wires 83 and end cap 50 can be adjustable on hollow guide shell 12 via threads 85. Adjusting the position of end cap magnet 82 can increase or decrease the magnetic force applied on inner pin magnet 80 by end cap magnet 82 as inner pin moves toward end cap 50. Adjusting the force applied by end cap magnet 82 on inner pin magnet 80 can allow a user to modify or adjust the injection rate of fluid or contents of cartridge 40 into a desired object. Moving end cap magnet 82 toward injection pin 36 can produce a stronger magnet force on injection pin magnet 80. A stronger magnetic force applied by end cap magnet 82 on injection pin magnet 80 can produce a faster injection or infusion rate.

In some embodiments, as shown in FIG. 14, injection device 10 can include a plurality of driver magnets 18 spaced radially on slider member 16 in a symmetrical pattern or orientation generally about injection pin 36. In other embodiments, the plurality of driver magnets 18 can be positioned within and symmetrically spaced radially about a circular ring shaped casing such that the plurality of driver magnets 18 are formed as a single unit. The plurality of radially spaced driver magnets 18 can help balance and counteract the non-longitudinal magnetic forces exerted on the actuator magnet 24 by the plurality of driver magnets 18 such that actuator magnet 24 and injection pin 36 can generally be suspended within hollow guide shell 12 by the plurality of driver magnets 18.

Figure 18:
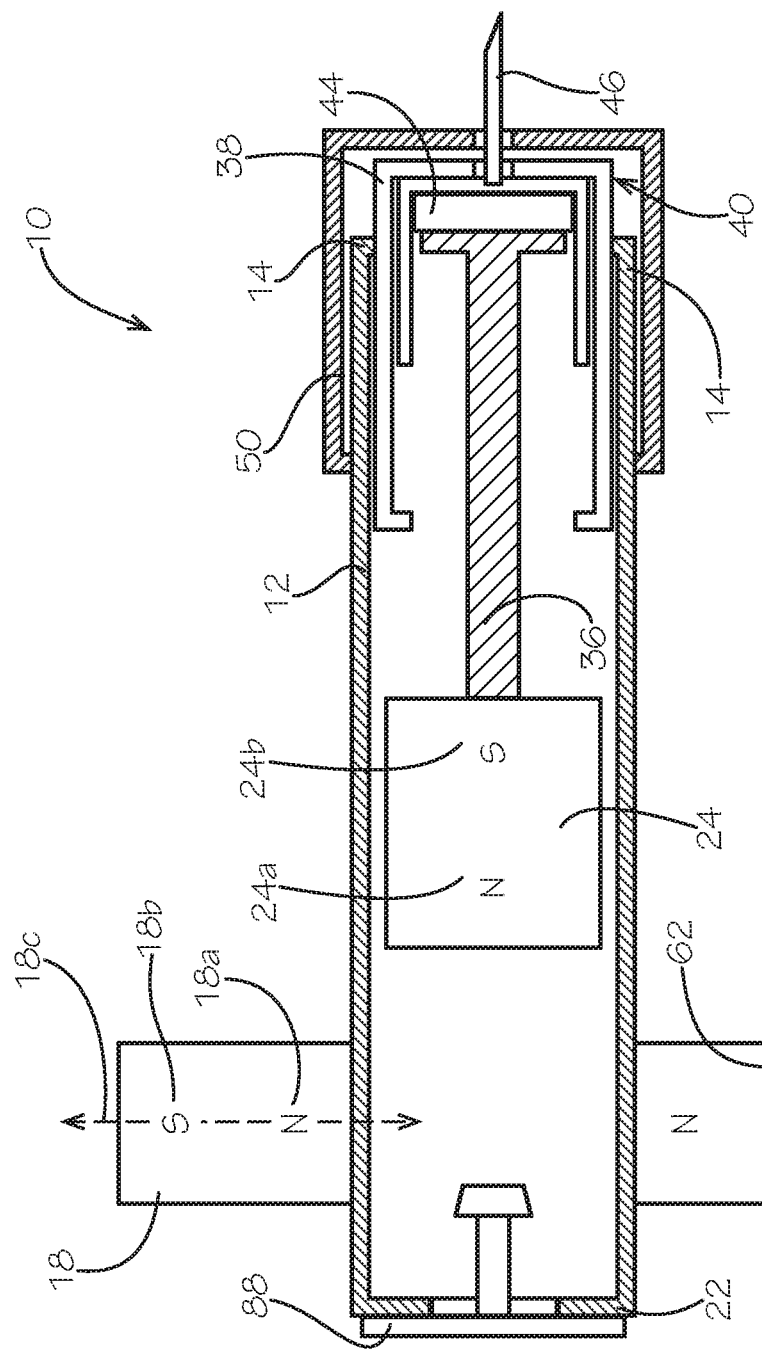
FIG. 18 is side a cross sectional view of the injection device of FIG. 17 in an actuated orientation.

Another embodiment of an injection device 10 of the present disclosure is shown in FIGS. 17-18. Driver magnet 18 in FIGS. 17-18 can be fixed to hollow guide shell 12. Actuator magnet 24 is positioned in hollow guide shell 12 and an actuation button 88 can extend into hollow guide shell 12 and engage actuator magnet 24. Driver magnet 18 can have a first driver magnetic pole 18a, a second driver magnet pole 18b, and a driver magnetic axis 18c. Actuator magnet 24 can have a first actuator magnet pole 24a, a second actuator magnet pole 24b, an actuator magnetic axis 24c, and an actuator midline 24d. Prior to actuation of device 10, first actuator magnet pole 24a can be positioned between back end 22 of hollow guide shell 12 and first driver magnet pole 18a of driver magnet 18, such that driver magnet 18 exerts a retracting magnetic force 28 on actuator magnet 24 in a direction away from injection end 14. Actuation button 88 can extend through back end 22 of hollow guide shell 12 to engage actuator magnet 24. Retracting magnetic force 28 exerted on actuator magnet 24 can help retain actuation button 88 in an outward position on hollow guide shell 12.

Actuation button 88 can be selectively depressed to push actuator magnet 24 toward injection end 14, as shown in FIG. 18. Actuator magnet 24 can cross the magnetic shift line 32, wherein when first actuator magnet pole 24a crosses the magnetic shift line 32, driver magnet 18 exerts an injection force 34 on actuator magnet 24 in a direction towards injection end 14. In some embodiments, magnetic shift line 32 can be driver magnetic axis 18c of driver magnet 18, and injection force 34 is exerted on actuator magnet 24 by driver magnet 18b when first actuator magnet pole 24a crosses driver magnetic axis 18c, such that at least half of driver magnet 18 is positioned behind first actuator magnet pole 24a. Injection force 34 can cause injection pin 36 coupled to actuator magnet 24 to engage cartridge 40 positioned in cartridge holder 38 to push plunger 44 of cartridge forward to inject fluid contained in cartridge 40 into a desired object.

Figure 32:
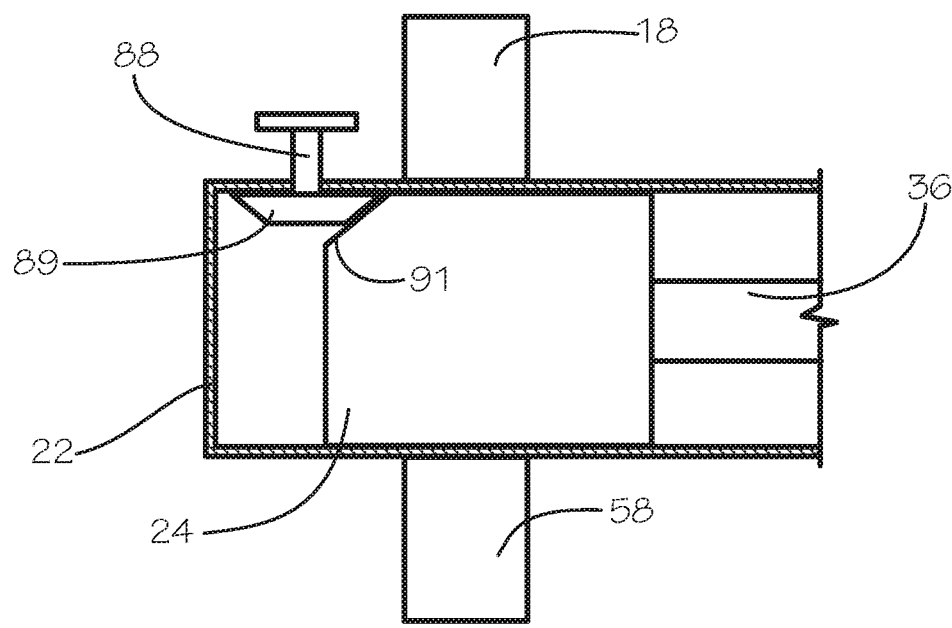
FIG. 32 is a cross sectional view of an injection device having an actuation button that extends into a hollow guide shell radially from a side of hollow guide shell.
Figure 33:
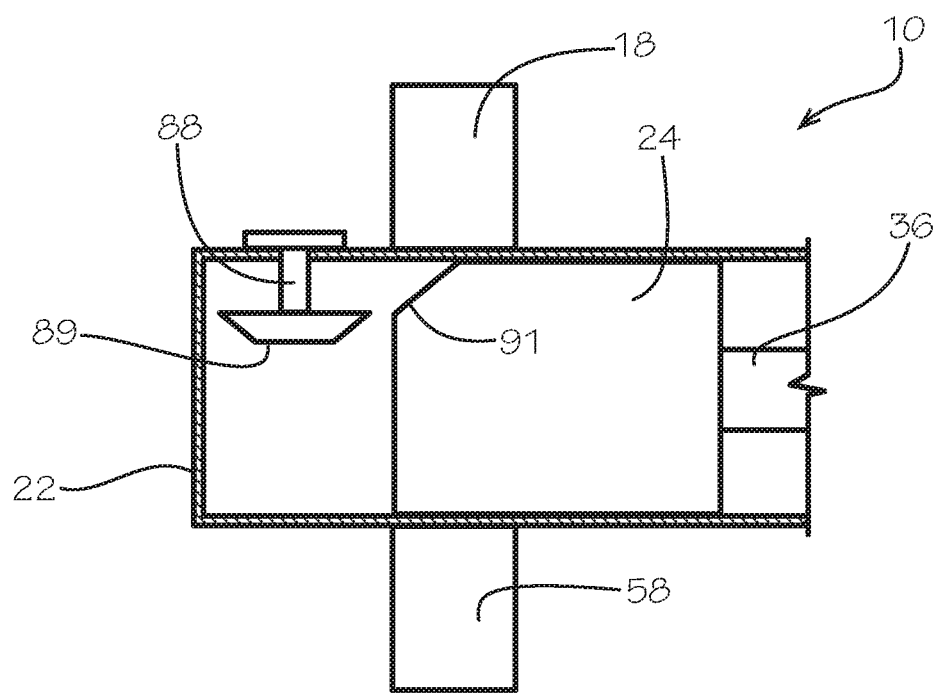
FIG. 33 is a cross sectional view of the injection device of FIG. 32 with the actuation button depressed.

In some embodiments, actuation button 88 can be aligned with longitudinal axis 20. In other embodiments, as shown in FIGS. 32-33, actuation button 88 can extend into hollow guide shell 12 from a side of hollow guide shell 12 such that actuation button extends radially into hollow guide shell 12. A distal end 89 of actuation button 88 can have an injection side facing the injection end that engages either actuator magnet 24 or a frame or other component that is coupled to actuator magnet 24. As radially extending actuation button 88 is depressed, the angled side of the distal end 89 of the actuation button forces actuator magnet 24 away from back end 22 to actuate injection device 10. In some embodiments, actuator magnet 24 or another structure coupled to actuator magnet 24 that is engageable by actuation button 88 can have an angled surface 91 that can engage angled distal end 89 of actuation button 88 to force actuator magnet 24 in a direction away from back end 22 as actuation button 88 is depressed. In some embodiments, distal end 89 of actuation button 88 can have a conical or frustoconical shape. Having an actuation button disposed on a side of hollow guide shell 12 can allow a user to easily depress actuator button 88 while the user has a conventional grip on hollow guide shell 12. The user can depress actuation button 88 with the user's thumb or other finger while hollow guide shell 12 is grasped in the palm of the user's hand, as opposed to the user having to move the user's thumb to back end 22 of hollow guide shell 12 to depress an actuation button.

Figure 19:
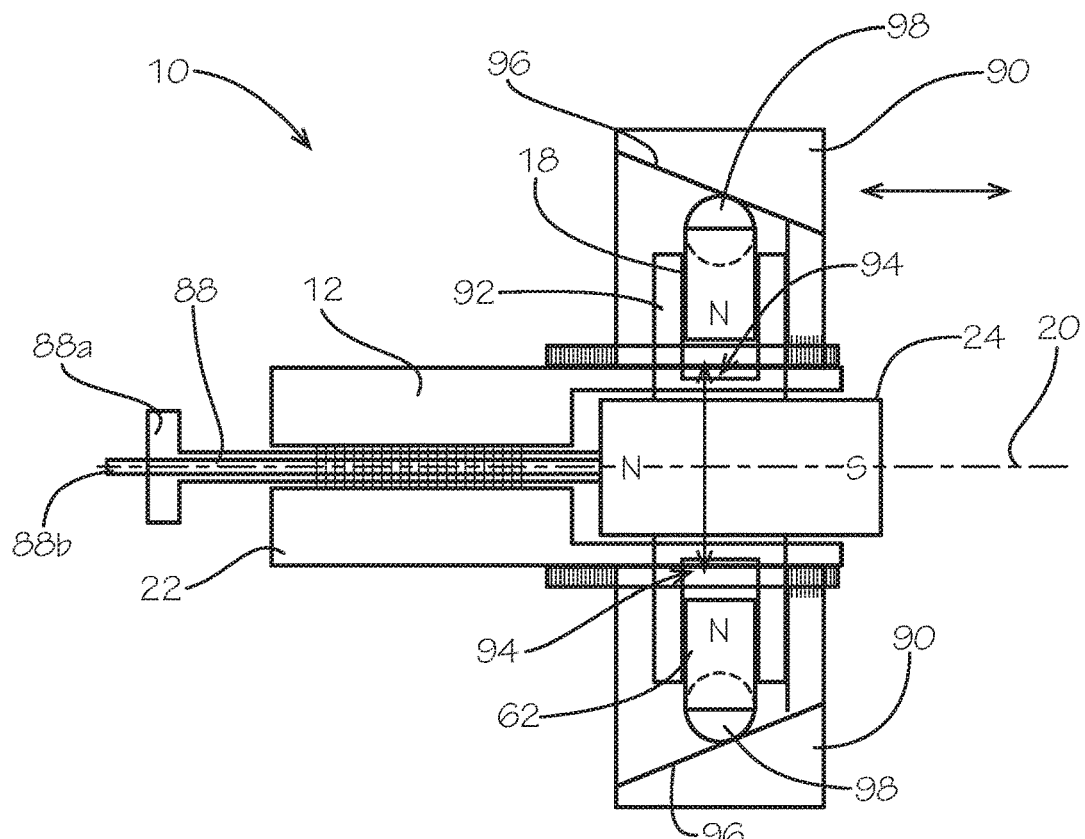
FIG. 19 is a side cross sectional view of another embodiment of an injection device of the present disclosure having a calibration collar engaged with a driver magnet of the device to adjust the position of the driver magnet relative to the actuator magnet.

In some embodiments, as shown in FIG. 19, actuation button 88 can have an outer member 88a and an inner member 88b. Inner member 88b can be slidably received in outer member 88a. Outer member 88a can be threadably engaged with hollow guide shell 12 such that the distance in which outer member 12 extends into hollow guide shell 12 can be adjusted. Outer member 88a can act as a stop which resists motion of actuator member 24 in a direction toward back end 22 of hollow guide shell 12. As such, when driver magnet 18 is fixed to hollow guide shell 12, outer member 88a can be used to determine the relative positions of driver magnet 18 and actuator magnet 24 when driver magnet 28 exerts a retracting force on actuator magnet 24 prior to actuation. The relative positions of driver magnet 18 and actuator magnet 22 can determine the sensitivity of actuation of injector device 10 as described above with respect to the proximity of driver magnet 18 and/or actuator magnet 24 to the magnetic shift line. Inner member 88b can be pressed such that inner member 88b slides within outer member 88a to push actuator magnet 24 past magnetic shift line and actuate injection device 10.

Figure 40:
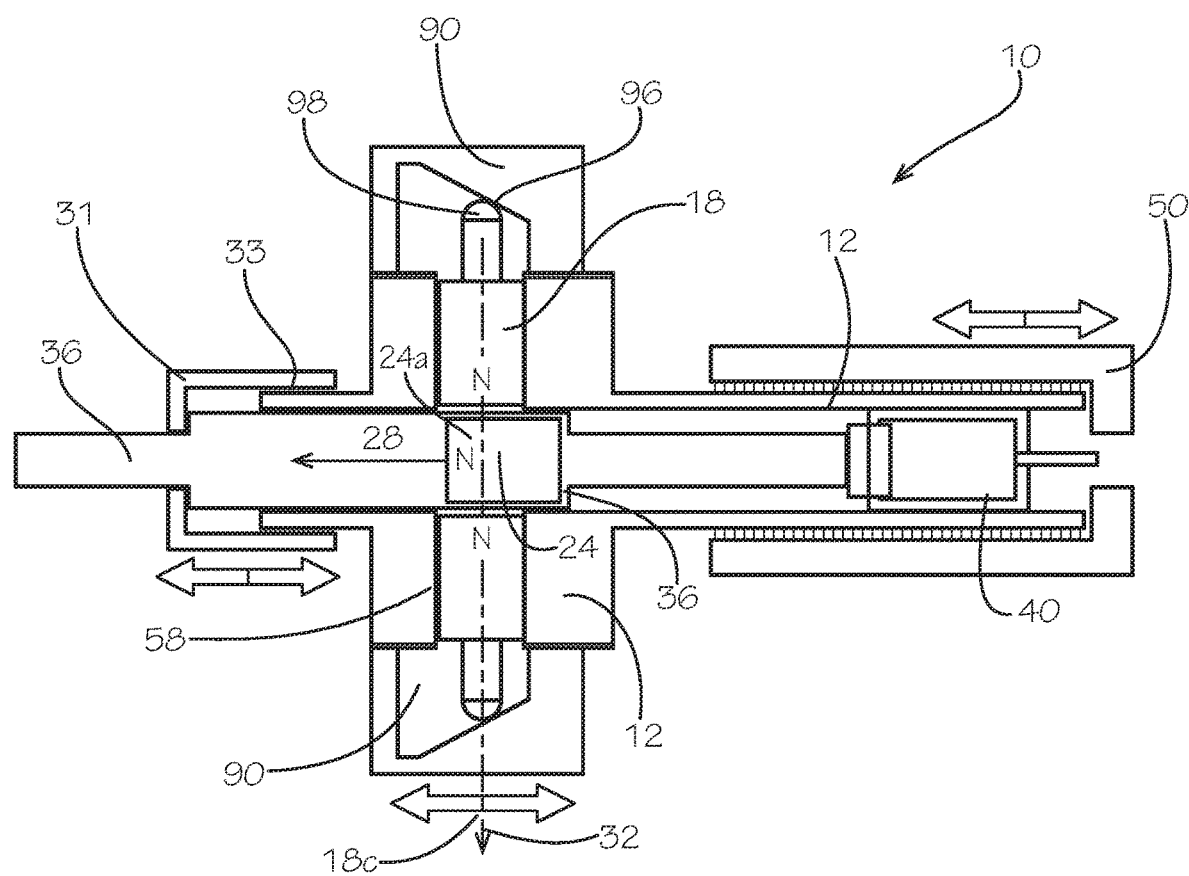
FIG. 40 is a cross sectional view of another embodiment of an injection device including an adjustable rear stop for an actuator magnet.

In some embodiments, as shown in FIG. 40, injection device 10 can include a rear stop 31 on back end 22 of hollow guide shell 12, wherein when first actuator magnet pole is positioned between the back end and the driver magnet axis, the retracting force 28 biases actuator magnet 24 or a carrier frame 60 for actuator magnet 24 against rear stop 31. In some embodiments, rear stop 31 can be fixed to hollow guide shell and designed to maintain actuator magnet 24 in a position such that the force required to move the first actuator magnet pole 24*a* across driver magnet axis 18*c* and magnetic shift line 32 is less than 5 pounds. In some embodiments, rear stop 31 can be adjustable on back end 22 of hollow guide shell 12 to adjust the position of first actuator magnet pole 24*a* relative to driver magnet axis 18*c* when actuator magnet 24 is positioned between driver magnet axis 18*c* and back end 22. Rear stop can be threadingly engaged with hollow guide shell 12 via rear stop threads 33 such that rear stop 31 can move longitudinally on hollow guide shell 12 to adjust the relative positions of first actuator magnet pole 24*a* and driver magnet axis 18*c* to adjust the actuation energy needed to actuate injection device 10. While the actuation energy could be minimized and you approach zero if desired, in some embodiments, a small but significant actuation force can be designed for such that injection device 10 does not accidentally actuate, for instance if the device is moved or jerked quickly and the inertia of actuator magnet 24 and injection rod 36 accidentally force first actuator magnet pole 24*a* past magnetic shift line 32.

As such, in some embodiments, as shown in FIGS. 2-3, driver magnet 18 can be movable via a slider member 16 which can be actuated near injection end 14 of hollow guide shell to move driver magnet 18 in a direction towards back end 22 to actuate the drive mechanism of injection device 10. In other embodiments, as shown in FIGS. 17-18, driver magnets 18 can be fixed to hollow guide shell 12 and actuator magnet 24 can be moved in a direction toward injection end 14 via an actuation button 88 to actuate device 10.

Several embodiments of injection devices 10 having adjustable driver magnets are shown in FIGS. 19-22. Injection device 10 can include a hollow guide shell 12 having an injection end 14 and a longitudinal axis 20. An actuator magnet 24 can be disposed in hollow guide shell 12. A driver magnet 18 can be positioned on device 10 radially outward from actuator magnet 24. Driver magnet 18 can be selectively movable in a direction perpendicular to longitudinal axis 20 of hollow guide shell 12 to adjust injection force 34 applied to actuator magnet 24 when device 10 is actuated. A calibration collar 90 can be movable on device 10 relative to driver magnet 18 in a direction parallel to longitudinal axis 20. Calibration collar 90 can be engageable with driver magnet 18. Driver magnet 18 can move in a direction substantially perpendicular to longitudinal axis 20 as calibration collar 90 moves longitudinally relative to driver magnet 18.

In FIG. 19, driver magnet 18 is disposed on hollow guide shell 12 and movable on hollow guide shell 12 in a direction perpendicular to longitudinal axis 20. Calibration collar 90 can be threadingly engaged with hollow guide shell 12 such that calibration collar 90 can be rotated on hollow guide shell 12 to adjust the position of calibration collar 90 on hollow guide shell 12. Hollow guide shell 12 can have a driver magnet holder portion 92 including a driver magnet receptacle 94 shaped to receive driver magnet 18. Driver magnet 18 can be slidably received in driver magnet receptacle 94.

In other embodiments including a slider member 16, as shown in FIGS. 21-22, driver magnet 18 can be disposed on slider member 16 and movable on slider member 16 in a direction substantially perpendicular to longitudinal axis 20 of hollow guide shell 12. Calibration collar 90 can be threadingly engaged with slider member 16 such that calibration collar 90 can be movable relative to driver magnet 18. Having calibration collar 90 threadingly disposed on slider member 16, however, can help maintain the position of calibration collar 90 with respect to driver magnet 18 as slider member 16 moves from the first slider position to the second slider position. The relative positions of driver magnet 18 and calibration collar 90 are only adjusted if calibration collar 90 moves on slider member 16. Slider member 16 in the embodiment of FIGS. 21 and 22 can have a driver magnet holder portion 92 including a driver magnet receptacle 94 shaped to receive driver magnet 18, driver magnet 18 being slidably received into driver magnet receptacle 94.

Calibration collar 90 is shown as being threadingly engaged with either hollow guide shell 12 or slider member 16. In other embodiments, hollow guide shell 12 or slider member 12 can include a plurality of holes, notches, recesses, etc. A pin on calibration collar 90 can selectively engage or be inserted into one of the holes, notches, recesses, etc. such that calibration collar 90 can selectively move to a discrete location on hollow guide shell 12 or slider member 16 and be retained in said position by one of the holes notches, recesses, etc. in which the pin on calibration collar 90 can be inserted or engaged.

In either arrangement, calibration collar 90 can include an inclined surface 96 oriented at an acute angle with longitudinal axis 20. Inclined surface 96 can engage driver magnet 18 such that as calibration collar 90 is rotated and/or moved along hollow guide shell 12, inclined surface 96 can either push driver magnet 18 further into driver magnet receptacle 94, or allow driver magnet 18 to extend further outward from driver magnet receptacle 94. In some embodiments, as shown in FIGS. 19 and 21, injection device 10 can include a second driver magnet 62 positioned on device 10 radially outward from actuator magnet 24 on an opposing side of longitudinal axis 20 from driver magnet 18. Driver magnet 18 and second driver magnet 62 can be oriented in a repulsive interaction with one another, with like poles of first and second driver magnets 18 and 62 facing one another. Calibration collar 90, and particularly inclined surface 96 of calibration collar 90, can be engaged with both the first and second driver magnets 18 and 62, and the repulsive interaction between first and second driver magnets 18 and 62 can maintain or bias first and second driver magnets 18 and 62 in an engaged position with calibration collar 90. As calibration collar 90 moves on hollow guide shell 12, first and second driver magnets 18 and 62 move simultaneously in a direction perpendicular to longitudinal axis 20.

In some embodiments, injection device 10 can include a roller bearing 98 positioned between driver magnet 18 and inclined surface 96 of calibration collar 90, driver magnet 18 engaged with inclined surface 96 via roller bearing 98. Roller bearing can allow driver magnet 18 to roll along inclined surface 96 of calibration collar 90 as calibration collar 90 is moved in a direction parallel to longitudinal axis 20 and driver magnet 18 moves in a direction perpendicular to longitudinal axis 20.

Figure 20:
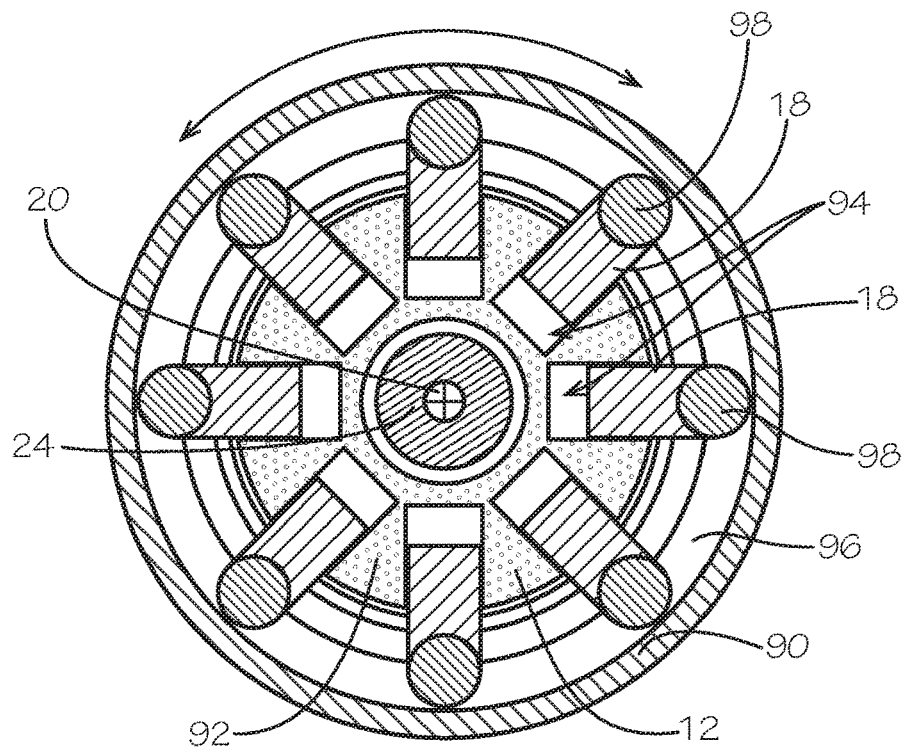
FIG. 20 is a rear cross sectional view of the injection device of FIG. 19.

In some embodiments, as shown in FIG. 20, injection device 10 can include a plurality of driver magnets 18 positioned radially about actuator magnet 24 in a repulsive interaction with one another. In some embodiments, device 10 can include at least four driver magnets. Driver magnets 18 can be positioned on and moveable with respect to either hollow guide shell 12 or slider member 16. A roller bearing 98 can be positioned between each of driver magnets 18 and inclined surface 96 of calibration collar 90. As calibration collar 90 is moved in a longitudinal direction relative to driver magnets 18, driver magnets 18 can simultaneously move in a direction perpendicular to longitudinal axis 20 to adjust the relative positions of driver magnets 18 with respect to actuator magnet 24.

As such, calibration collar 90 can be used to adjust or alter the position of driver magnets 18 with respect to actuator magnet 24 positioned within hollow guide shell 12. The closer driver magnets 18 are to actuator magnet 24, the stronger the injection force applied to actuator magnet 24 is when injection device 10 is actuated. A stronger actuating driver magnet force can increase the injection or infusion rate of fluid being injected by injection device 10. As such, calibration collar 90 can be utilized to adjust the injection force, and thus the injection rate, when injection device 10 is used for different medications.

Figure 29:
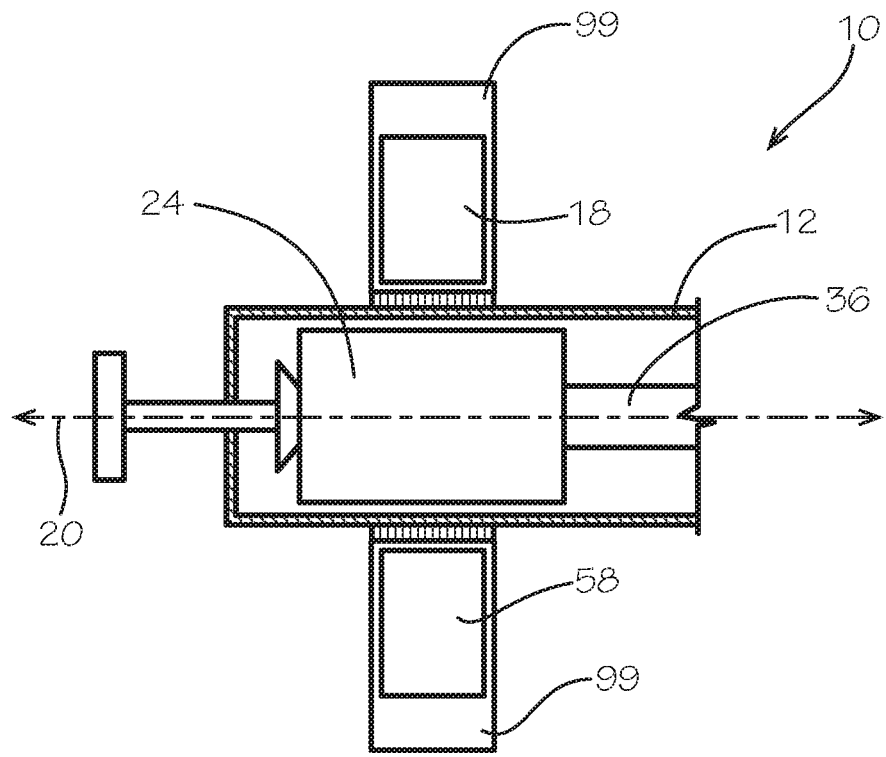
FIG. 29 is a partial cross sectional view of an embodiment of an injection device including a removable calibration collar with a first driver magnet orientation.
Figure 30:
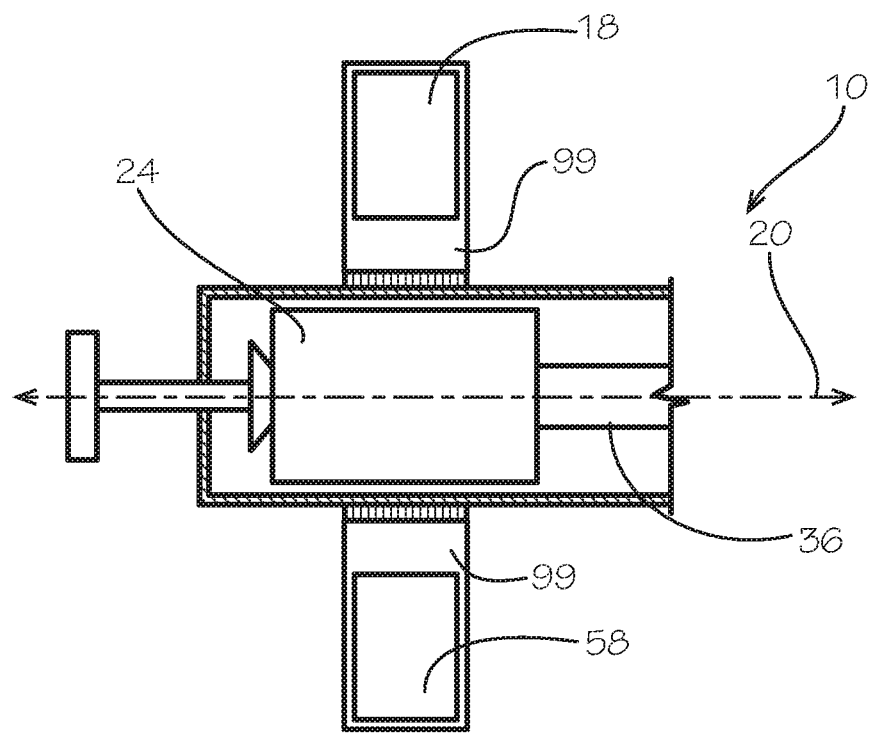
FIG. 30 is a partial cross sectional view of the injection device of FIG. 30 with another calibration collar attached to the hollow guide shell having a second driver magnet orientation.

In other embodiments, as shown in FIGS. 29 and 30, device 10 can include a removable driver magnet holder 99. Driver magnets 18 can be positioned within the driver magnet holder 99 at discrete distances from longitudinal axis 20 of hollow guide shell 12. Driver magnet holder 99 can be removable from hollow guide shell 12 by way of threads, snap fits, or other fastener structures. If a different injection force or infusion rate is desired, driver magnet holder 99 can simply be removed and replaced with a different driver magnet holder 99 where the distance between the driver magnets and longitudinal axis 20 is either increased or decreased as desired.

Figure 31:
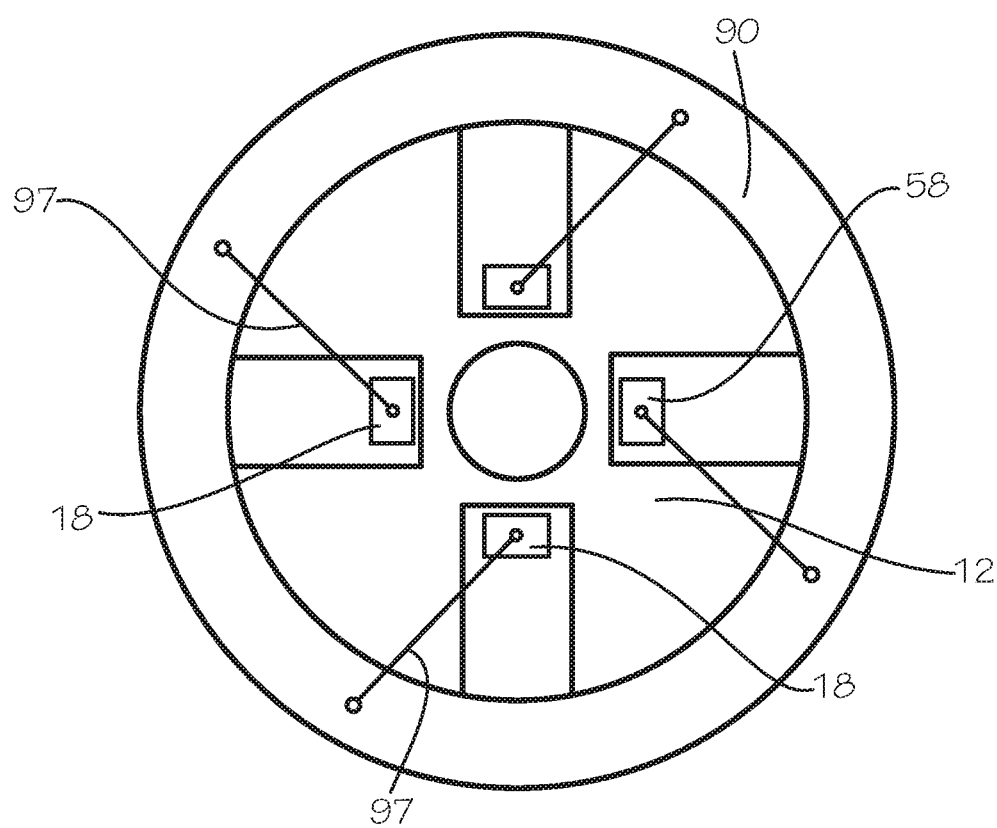
FIG. 31 is cross sectional view of another embodiment of an injection device having a calibration collar connected to movable driver magnets by tension linkages.

In still other embodiments, as shown in FIG. 31, a linkage member 97 can be connected between a calibration collar 90 and a corresponding driver magnet 18 positioned within slots in either the hollow guide shell 12 or slider member. As calibration collar 90 is rotated, the linkage members 97 either pull the driver magnets away from longitudinal axis 20 or push driver magnets toward longitudinal axis 20, depending on the direction of rotation of the calibration collar 90.

The ability to control the driving force of injection device 10, as described for FIGS. 19-22 and 29-31, from driver magnet 18, and the ability to control the force applied to cartridge 40 by injection pin 36, as described for FIGS. 9-11, can allow injection device 10 to be adjustable and customized for various medications and drug delivery protocols. In some embodiments including a calibration collar 90 with an inclined surface 96 that is translatable along hollow guide shell 12, as shown in FIGS. 19-22, markings or guide marks can be positioned along the longitudinal path of calibration collar 90. Each guide mark can correspond to a particular medicine or group of medicines, or a particular injection rate, the guide mark indicating that when calibration collar 90 is at the particular guide mark, the injection rate of injection device 10 is suitable for the medicine or group of medicines corresponding to the guide mark. A similar guide system can be used for embodiments having adjustable end cap magnets 82 on an end cap 50 of device 10, as shown in FIG. 11a.

In other embodiments where injection pin 36 includes an injection pin magnet 80 as shown in FIG. 11, cartridge holder 38 can include one or more magnets that can interact with an injection pin magnet 80 as injection pin 36 approaches cartridge holder 38. A magnet on cartridge holder 38 can be designed, by varying the size and strength of the magnet on the cartridge holder 38, such that a desired injection or infusion rate is produced from cartridge 40 when injection device 10 is actuated, the infusion rate being suitable for a particular fluid or medicine contained in cartridge 40. As such, cassettes 100 including cartridges 40 and cartridge holders 38 can be designed for corresponding medications such that the same injector device 10 can be used to inject different types of medications, at a desired dose and injection rate for the fluid or medicine contained in a particular cartridge 40 when injection device 10 is actuated.

In some embodiments, injection device 10 can be designed such that injection device 10 is a single use device. Hollow guide shell 12 can be a continuous structure surrounding the internal components of device 10, which are assembled during manufacture of device 10. When injection device 10 is actuated by a user such that fluids in injection device 10 are administered or injected by device 10, the entire device 10 can be discarded. In such embodiments, the drive mechanism and/or a cassette including cartridge holder 38 and cartridge 40 can be designed for a particular type of fluid or medication to deliver a suitable amount or dosage of fluid at a suitable injection rate, such that injection device 10 as a whole is designed for a particular fluid or medication.

Figure 24:
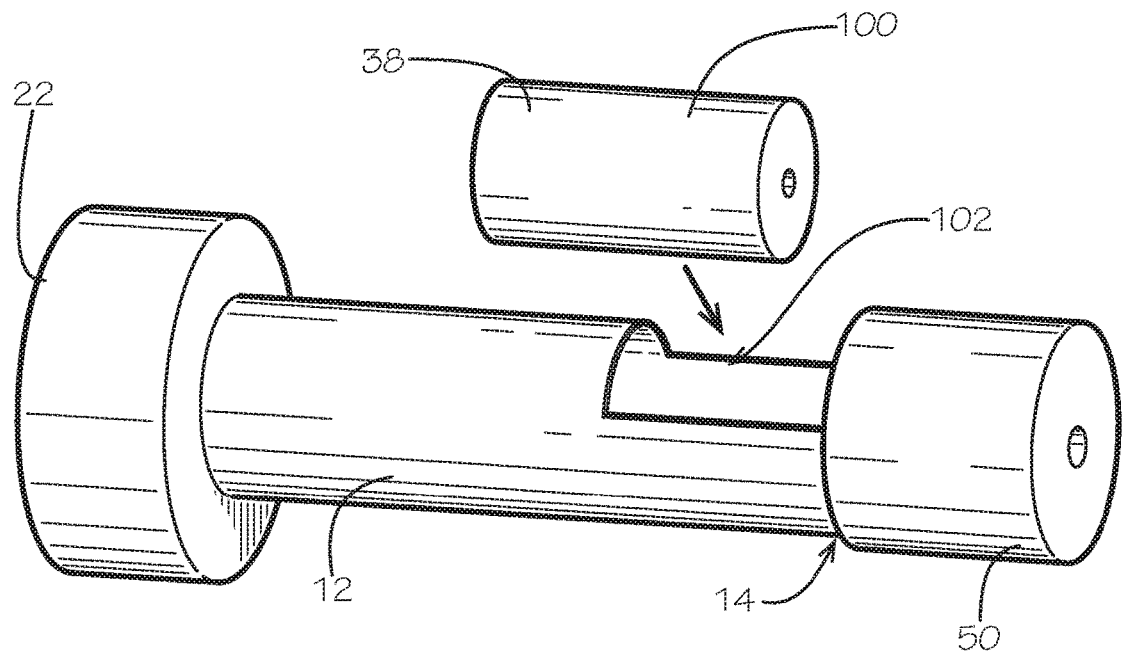
FIG. 24 is a side perspective view of another embodiment of an injection device of the present disclosure having a hollow guide shell with a cassette aperture for interchanging or removing a cassette including a cartridge holder and cartridge used in the injection device.
Figure 25:
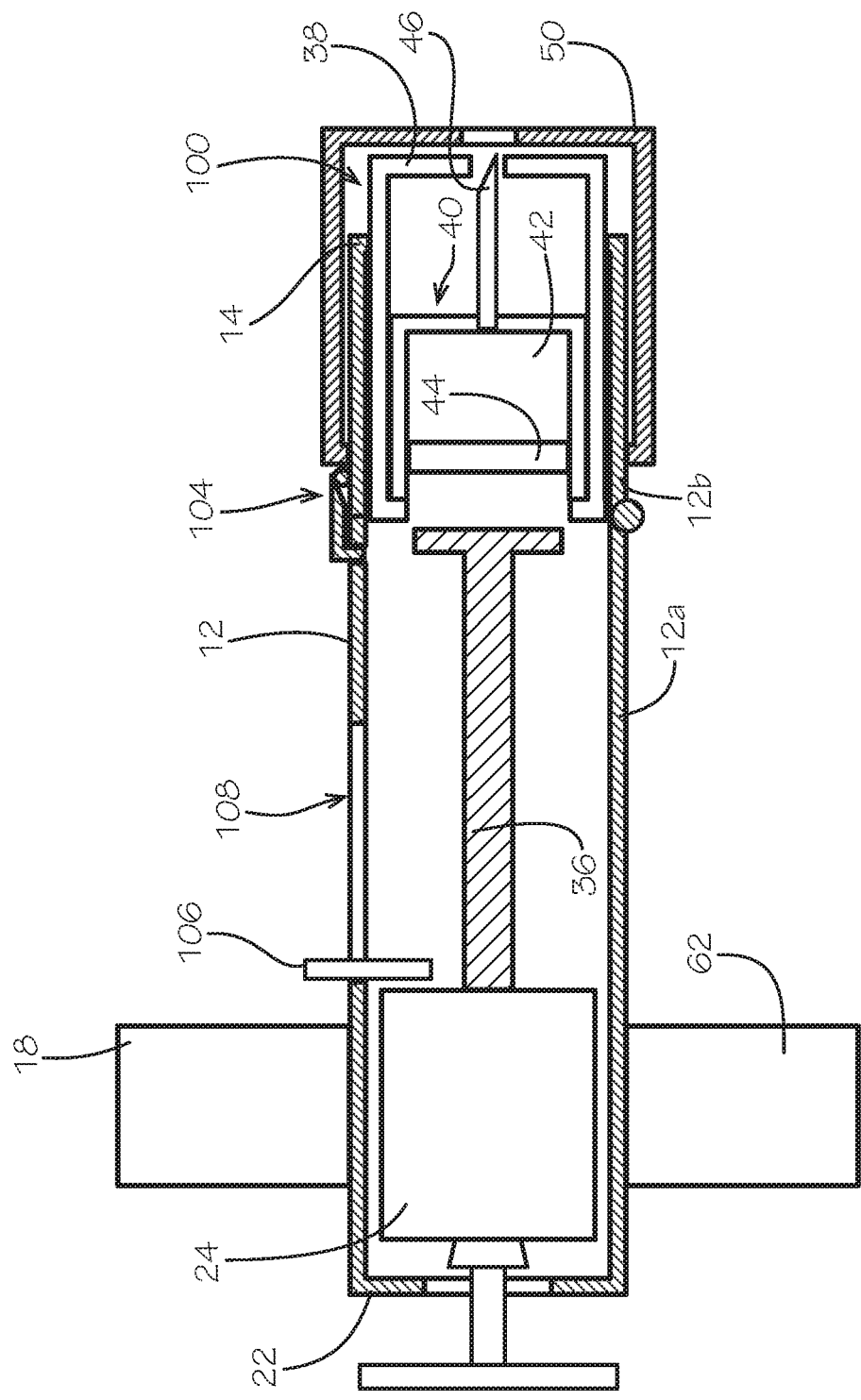
FIG. 25 is a side cross sectional view of another embodiment of an injection device of the present disclosure having a two piece hollow guide shell that is collapsible to expose and reload a cassette in the injection device.
Figure 26:
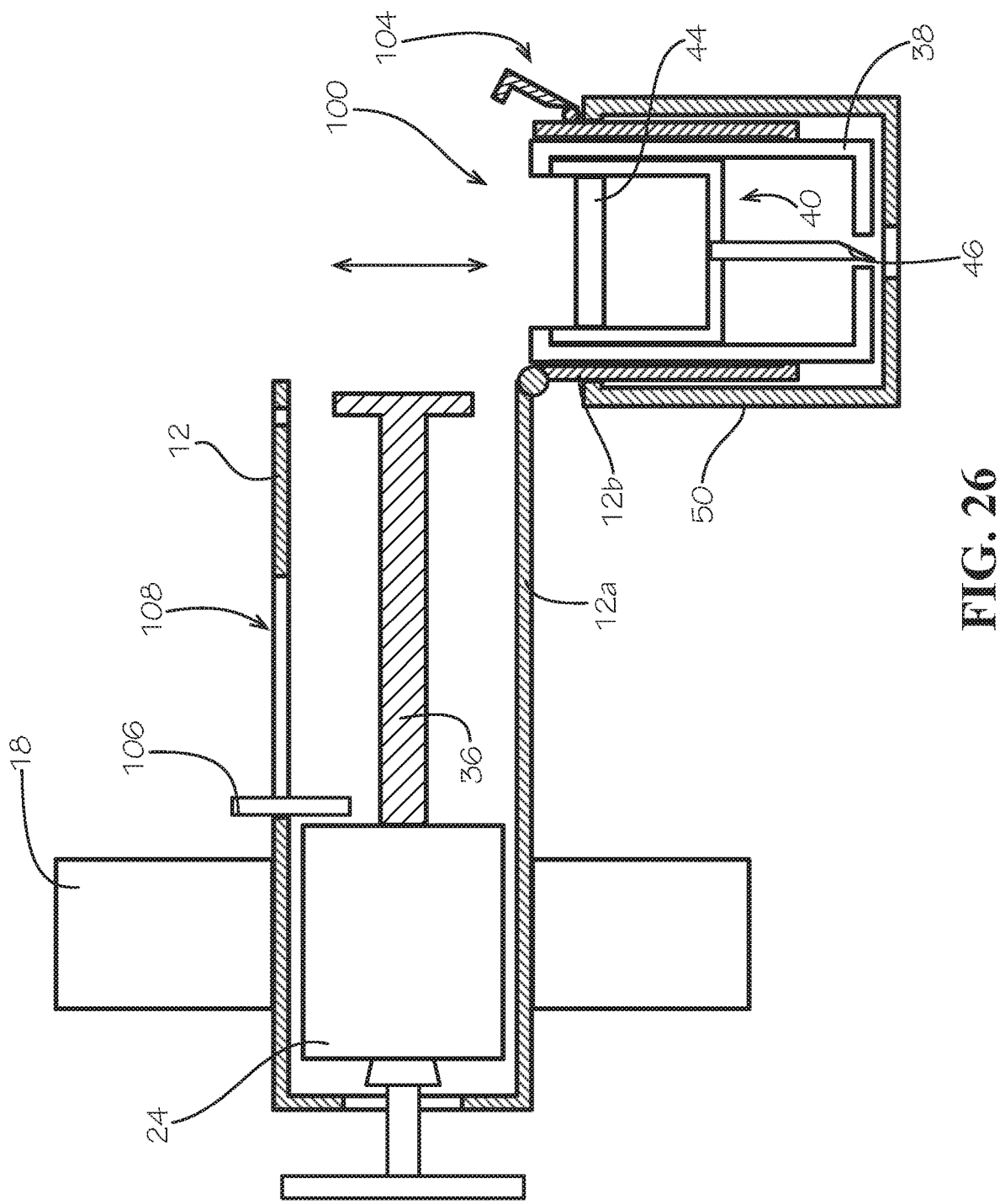
FIG. 26 is a side cross sectional view of the injection device of FIG. 25 in an open orientation.

In other embodiments, as shown in FIGS. 24-26, injection device 10 can be designed such that prior to actuation, cassette 100 can be removable or interchangeable in injection device 10. In some embodiments, hollow guide shell 12 can include a cassette aperture 102 defined in hollow guide shell 12 toward an injection end 14 of hollow guide shell 12. Cassette aperture 102 can be sized and positioned on hollow guide shell 12 such that a cassette 100 can be loaded into hollow guide shell 12 and subsequently removed or changed for another cassette 100 as needed.

In other embodiments, as shown in FIG. 25, hollow guide shell 12 can include multiple pieces which can be removably connected together. The various pieces of hollow guide shell 12 can be separated to expose a cassette 100 within hollow guide shell 12, such that the cassette 100 can be removed from injection device 10 and/or replaced with a new cassette 100. In FIG. 25, a first portion 12a of hollow guide shell 12 can be pivotally connected to a second portion 12b of hollow guide shell 12a such that the portions 12a and 12b of hollow guide shell 12 can be opened or separated with respect to one another to expose cartridge 100 inside hollow guide shell 12. In some embodiments, hollow guide shell 12 can include a safety latch 104 or other locking mechanism which can secure the two portions 12a and 12b of hollow guide shell 12 together to secure a cassette 100 within injector device 10. In other embodiments, first portion 12a and second portion 12b of hollow guide shell 12 can be threadingly secured to one another. Second portion 12b of hollow guide shell 12b can be removed from first portion 12a of hollow guide shell 12 to expose a cassette 100 within hollow guide shell 12 in order to remove or replace cassette 100. The two portions 12a and 12b of hollow guide shell 12 can be screwed back onto one another once an appropriate cassette 100 is loaded into hollow guide shell 12 to secure cassette 100 within injection device 10. The features discussed above for allowing cassettes 100 to be interchangeable within injection device 10 can also be utilized in those embodiments having a slider member that moves rearward or away from an injection end of a hollow guide shell to actuate injector device 10.

In other embodiments, the cassettes can have one or more notches which can be engaged by a release mechanism built into the hollow guide shell to releasably secure a cassette within the hollow guide shell. For instance in some embodiments, a spring biased latch can selectively engage a notch in the side of a cassette as the cassette is loaded into the hollow guide shell. The latch can be biased to extend into the hollow guide shell and engage the cassette to retain the cassette within the hollow guide shell. A release button or lever can be operable to engage the latch and move the latch to a disengaged position to selectively release the cassette from the hollow guide shell.

In some embodiments, a pivoting L shaped latch member can be biased by way of a torsion spring such that a portion of the L-shaped latch member extends into the hollow guide shell. A release button can be positioned on the hollow guide shell that can selectively rotate the L-shaped latch member such that the latch moves out of the interior passage of the hollow guide shell so that a cassette can move freely in and out of the hollow guide shell. When the release button is depressed, the latch member can rotate to engage the cassette. In some embodiments, a distal or engaging end of the latch can include a surface angled toward the injection end of the hollow guide shell such that as a cassette is loaded into the hollow guide shell, the cassette itself can force the latch out of the interior of the hollow guide shell, the latch reengaging a notch in the cassette once the notch is aligned with the latch.

In some embodiments where cassettes of medication or fluid are removable from injector device 10, injector device 10 can include one or more retention magnets positioned within hollow guide shell 12 or end cap 50 which can engage a corresponding retention magnet on a cassette 100 such that when cassette 100 is loaded into injector device 10 cassette 100 can be maintained in a desired position within injection device 10 by the corresponding retention magnets. In some embodiments, the magnet on cartridge holder 38 that can determine the injection rate at which fluid or medication is injected from the cartridge when injection device 10 is actuated can also interact with one or more retention magnets positioned in injector device 10 as cassette 100 is being loaded into injector device 10 to retain cassette 100 in a desired position within injector device 10.

Having an injection device 10 where a cassette 100 of fluid or medicine can be removed from or interchanged with another cassette 100 can be of great benefit particularly for medications that expire over time or that may become spoiled because of certain sensitivities the fluids have to external conditions. For instance, epinephrine expires after a year and is sensitive to extreme temperatures. As such, if an injector is used to administer epinephrine, and the injection is not needed for over a year such that the medication in an initial cassette 100 were to spoil, or if the medication were exposed to extreme temperatures compromising the medication, the old cassette 100 could simply be removed from injection device 10 and replaced with a new cassette without the consumer having to entirely replace the injection device 10. Such an ability to simply switch bad or expired cassettes for new ones can save consumers substantial cost in maintaining an effective supply of medicines and injector devices 10.

Additionally, cassettes 100 can be provided or sold separately from injector devices 10, such that cassettes 100 can be interchangeably loaded into a universal injector device 10 suitable for use with all cassettes 100. Cassettes 100 can be standalone, self-contained, highly compact sealed sterile cassette 100, such that the medication and needle contained within cassettes 100 are sterilized prior to use. Adapting a particular cassette 100 for a particular fluid or medication can allow cartridges of varying dosages and needles of varying sizes, to be used with the same injector device 10.

Such an injector device 10 can be beneficial, for instance, in a hospital setting, where the hospital can keep a supply of unloaded injectors 10 on hand as well as a supply of cassettes 100 containing various types of fluids or medications. When the need for an injection arises, a medical professional can simply grab an injection device 10 and choose an appropriate cassette 100 corresponding to the medication needed for the particular patient, load cassette 100 into injection device 10, and administer the fluid or medication to a patient. In some embodiments, once an injection device 10 has been actuated, the injection device 10 can be discarded along with the spent cassette. When another injection need arises a fresh auto injector 10 and cassette 100 can be used. Having the cassettes 100 separable from the injector devices 10 can allow the hospital to have a supply of injector devices 10 on hand that can be used interchangeably with various cassettes for different medications, without having to have an injector device for each and every cassette on hand, which is the case for current auto injectors where cassettes are an integral, non-removable part of the injector device. When the supply of injector devices 10 runs low, a hospital can simply purchase more generic or universal injector devices, without having to have specific injector devices 10 associated with specific medications. Such a system can make keeping an adequate supply of injector devices 10 and cassettes 100 for different medications on hand easier and more efficient.

In some embodiments, as shown in FIGS. 25-26, injector devices 10 can be designed such that the injector device 10 is reloadable and re-cockable. For such devices 10, cassettes 100 can be interchangeable or removable from injector device 10, and the driving mechanism including actuator magnet 24 and/or driver magnet 18 can be re-cockable or returnable to a retracted state where driver magnet 18 applies a retracting force on actuator magnet 24, such that injection device 10 can be reused for another injection. In the embodiment shown in FIG. 25, injector device 10 can include a re-cocking element 106 disposed on hollow guide shell 12. Re-cocking element 106 is shown as a rod that extends into hollow guide shell 12 and is slidable in a re-cocking element channel 108 defined in hollow guide shell 12. Re-cocking element 106 can move toward injection end 14 of hollow guide shell 12 when injector device 10 is actuated. After actuation, re-cocking element 106 can be pulled toward back end 22 of hollow guide shell 12 to return actuator magnet 24 to a position within hollow guide shell 12 where driver magnet 18 exerts a retracting force on actuator magnet 24 in a direction toward back end 22 of hollow guide shell to effectively re-cock the driving mechanism for the next injection. The spent cassette 100 can be removed from injector device 10 and discarded as described above and a new cassette can be loaded into injector device 10 for the next injection.

Another embodiment of a cocking mechanism for injection device 10 is shown in FIGS. 35-39. Injection device 10 can include a cocking sleeve 130 that can be slidable on back end 22 of hollow guide shell 12. Back end 22 of hollow guide shell 12 can include two back end arms with slots defined there between. Cocking sleeve 130 can include angled protrusion members 132 oriented to extend into the slots defined in back end 22 of hollow guide shell 12. Injection pin 36 and or carrier frame 60 can include a rear angled portion 134 with a shape that corresponds to angled protrusion members 132.

As cocking sleeve 130 slides on back end 22, angled protrusion members 132 on cocking sleeve 130 can engage angle rear portion 134 such that as cocking sleeve 130 is pulled away from injection end 14, as shown in FIGS. 36 and 37, injection pin 36 and actuator magnet 24 can be withdrawn to a retracted position wherein driver magnets 18 produces a retracting force on actuator magnet 24 that biases and retains actuator magnet towards back end 22 prior to actuation.

In some embodiments, back end 22 can include a first cocking magnet or magnetic piece 136 and cocking sleeve 130 can include a second cocking magnet or magnetic piece 138. The two cocking magnetic pieces 136 and 138 can be positioned in an attractive orientation such that as cocking sleeve 130 is fully pulled back and injection device 10 is re-cocked, cocking sleeve 130 can be released and the cocking magnets 136 and 138 can return cocking sleeve 130 to the position shown in FIG. 38. In some embodiments, when injection pin 36 is the retracted position, a portion of injection pin 36 can extend through holes in back end 22 and cocking sleeve 130. The portion of injection pin 36 extending out from cocking sleeve 130 can provide visual indication that the injection device 10 has been re-cocked or loaded and is ready for actuation. The portion of injection pin 36 extending out of cocking sleeve 130 can also double as an actuation button that can be pressed to actuate the device, as shown in FIG. 39.

Figure 35:
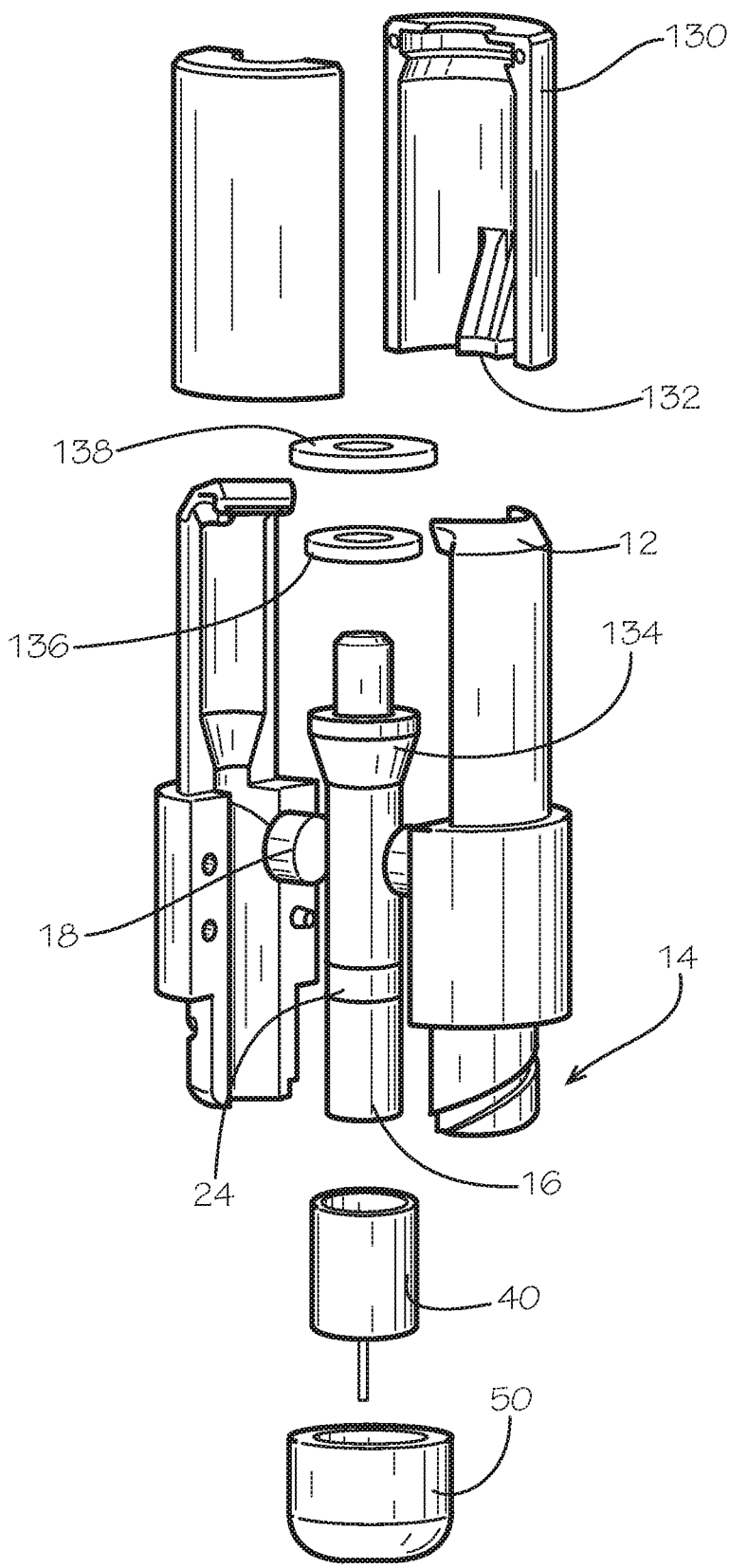
FIG. 35 is an exploded view of another embodiment of an injection device having a cocking sleeve for re-cocking the device between uses.

In some embodiments, as shown in FIG. 35, end cap 50 can be a twist off cap that can be selectively removed between uses to allow a spent fluid cartridge to be removed and a new cartridge to be placed within hollow guide shell once injection pin 36 and device 10 have been re-cocked.

Having an injector device 10 that is reloadable and re-cockable can help reduce the number of times the drive mechanism and main components of injector device 10 must be replaced. A spent cassette can simply be discarded, the injector device 10 and drive mechanism can be re-cocked and sterilized if necessary for the next injection, and a new cassette can be loaded into the injector device 10. Such a design can greatly reduce the cost of certain injections which currently require the entire injection device 10 to be replaced after every use. For instance, such a design could enable a hospital to utilize an auto-injector to inject medications that currently can only be cost effectively injected using manual syringes. The more extensive use of auto-injectors in lieu of manual syringes can help enable hospitals to more quickly and efficiently administer injections, reduce the risk of accidental needle sticks, reduce the risk of administering incorrect medications (e.g., due to the use of color code cartridges), and provide patients with more consistent, less painful and quicker injections even when administered by a person with relatively limited skill or dexterity.

For devices 10 including a slider member 16, as shown in FIG. 23, hollow guide shell 12 can include a driver magnet aperture 86. Driver magnet 18 can extend through driver magnet aperture 86. Additionally, a carrier frame 60 coupled to actuator magnet 24 can include a carrier flange 110 which can extend out of driver magnet aperture 86 such that a user can engage carrier flange 110 via driver magnet aperture 86. After actuation of injection device 10, driver magnet 18 can be pulled toward injection end 14 of hollow guide shell 12, and carrier flange 110 can be pulled toward back end 22 of hollow guide shell 12 such that driver magnet 18 and actuator magnet 24 can be returned to a position such that driver magnet 18 exerts a retracting force on actuator magnet 24 towards back end 22 of hollow guide shell 12. As such, carrier flange 110 can allow an injection device 10 including a driver magnet 18 movable on a slider member 16 to be re-cocked for the next injection. A spent cartridge or cassette can be replaced with a fresh cartridge or cassette, and the next injection can be performed.

Figure 27:
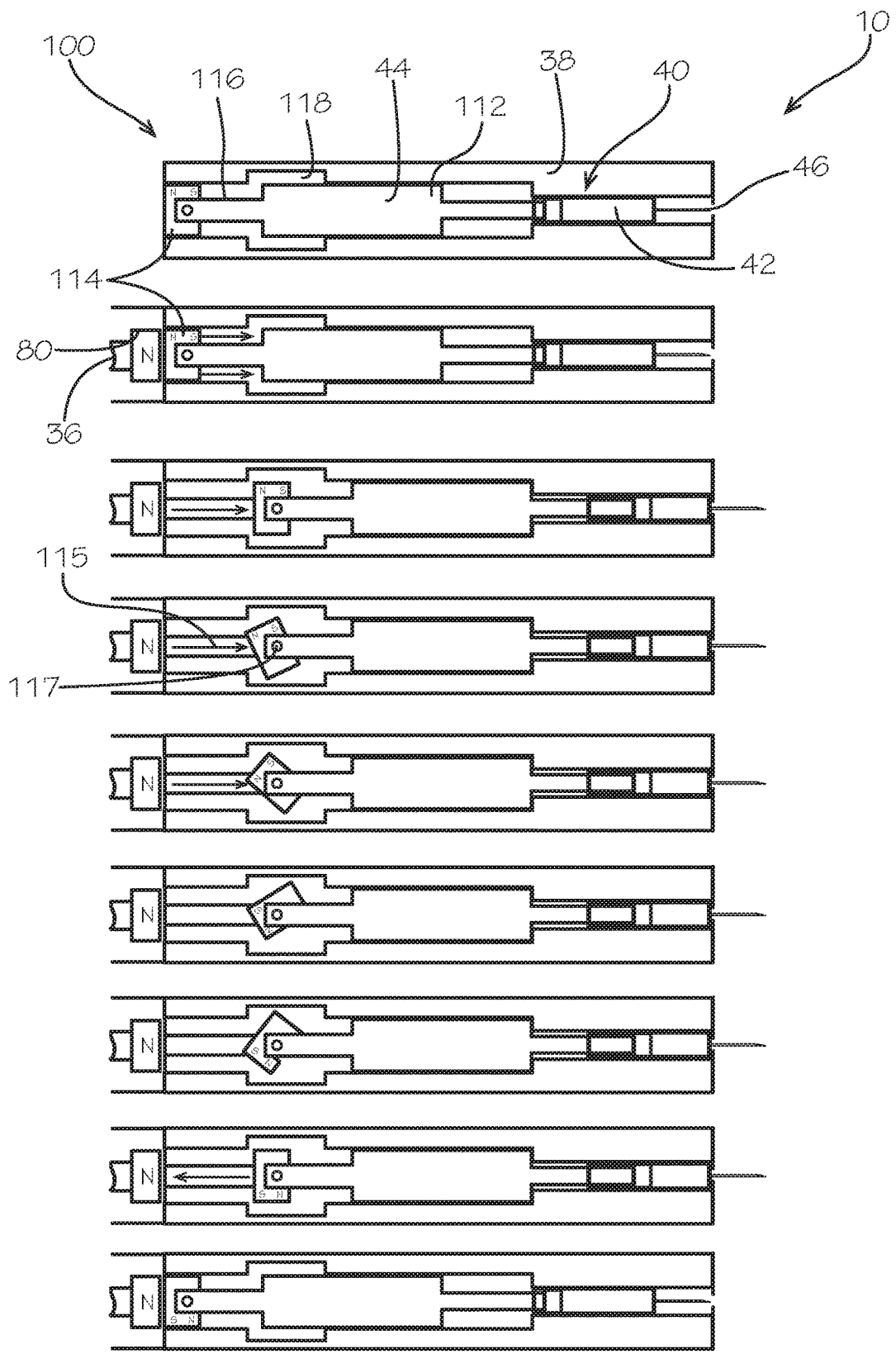
FIG. 27 is a side cross sectional view of another embodiment of a cartridge having a pivoting magnet container therein.

Another embodiment of a cassette 100 having a retractable feature is shown in FIG. 27. Plunger 44 of cartridge 40 can have a plunger frame 112 and a plunger magnet 114 pivotally connected to an end of plunger frame 112 oriented away from needle 46. Injection pin 36 can include an injection pin magnet 80 which can interact with plunger magnet 114 as injection device 10 is actuated and injection pin 36 moves toward cassette 100.

Cartridge holder 38 can include a plunger magnet guide channel 116, plunger magnet 114 initially received in plunger magnet guide channel 116, plunger magnet guide channel 116 sized such that plunger magnet 114 cannot pivot or rotate within plunger magnet guide channel 116. Plunger magnet guide channel 116 can include a guide track 115 which can receive a connection pin 117 connecting plunger magnet 114 to plunger frame 112. Guide track 115 can help keep plunger frame 112 properly aligned within cartridge holder 38. Plunger magnet 114 and injection pin magnet 80 can initially be oriented in a repulsive interaction with like poles facing one another as shown in FIG. 27. As such, as injection pin 36 approaches cassette 100, injection pin magnet 80 can exert a magnetic force on plunger magnet 114 that forces plunger magnet away from injection pin 36, plunger 44 thereby pushing a receptacle 42 and needle 46 of cartridge 40 such that needle 46 can extend out of cassette 100 and be inserted into a desired object. As plunger 44 continues to move toward needle 46 due to the repulsive forces applied to plunger magnet 114 by injection pin magnet 80, medication or fluid within receptacle 42 can be forced by plunger 44 out of needle 46.

Cartridge holder 38 can also include a release chamber 118 positioned at the end of plunger magnet guide channel 116. Release chamber 118 can be wider than plunger magnet guide channel 116 such that plunger magnet 114 can be free to rotate or spin within release chamber 118. As plunger magnet 114 moves into release chamber 118, the repulsive forces exerted by injection pin magnet 80 on plunger magnet 114 can cause plunger magnet 114 to rotate within release chamber 118 such that plunger magnet 114 aligns itself in an attractive interaction with injection pin magnet 80, such that opposite poles of plunger magnet 114 and injector pin magnet 80 face one another. Injection pin magnet 80 can then exert an attractive force on plunger magnet 44 which can draw plunger magnet 114 back into plunger magnet guide channel 116 and toward injection pin 36 such that plunger frame 112 withdraws receptacle 42 and needle 46 into cassette 100. As such, once the injection is performed and a desired amount of medicine or fluid is injected into a desired object, needle 46 can be withdrawn into cassette 100 which can help prevent any inadvertent needle sticks after injection.

While plunger magnet 114 is shown as being pivotally connected to plunger frame 112 in FIG. 27 such that plunger magnet 114 can rotate to reverse the magnetic force applied on plunger magnet 114 by injection pin magnet 80 to retract needle 46 after injection, in other embodiments, injection pin magnet 80 can be pivotally connected to injection pin 36 such that injection pin magnet 80 can rotate to reverse the magnetic force applied on plunger magnet 44 by injection pin magnet 80. In such embodiments, hollow guide shell can include an injection pin magnet guide channel that can prevent rotation of injector pin magnet 80, and an injector pin magnet release chamber which can allow rotation of injector pin magnet 80 after a desired amount of fluid or medicine has been injected from cartridge 40. Needle 46 can be withdrawn as injector pin magnet 80 rotates to orient itself in an attractive interaction with plunger magnet 114 and plunger magnet 114 and plunger frame 112 move toward injection pin magnet 80.

One benefit of the design of FIG. 27 is that injection pin 36 never penetrates cassette 100. Rather the magnetic interaction of injection pin magnet 80 and plunger magnet 114 drive the movement of plunger 44 without having to make physical contact. As such, cassette 100 can be more easily sealed and sterilized on the plunger side of cassette 100, as cartridge holder 38 can completely enclose plunger 44 providing for fewer potential leak points. A needle side of cassette 100 can be covered by a piercable membrane which can seal and keep the needle and medication within cassette 100 sterilized until actuation, where needle 46 can be forced through the membrane.

In still other embodiments, plunger 44 can include a fixed plunger magnet and injection pin 36 can include a fixed injection pin magnet 80 to produce a non-retractable injection, but such an injection can have the same benefit of the injection pin 36 not needing to be inserted into cassette 100 with the injection pin magnet and plunger magnet producing the desired magnetic force on the plunger magnet to inject a desired amount of fluid or medicine from cassette 100.

In other embodiments, injector device can include an expandable sheath similar to those commonly known in the art. The expandable sheath can be released once injector device is actuated. As injector device is removed from an object after injection, expandable sheath can extend out from injector device to effectively cover a needle extending from an injection end of the device to help protect against inadvertent needle sticks after injection.

Figure 28A:
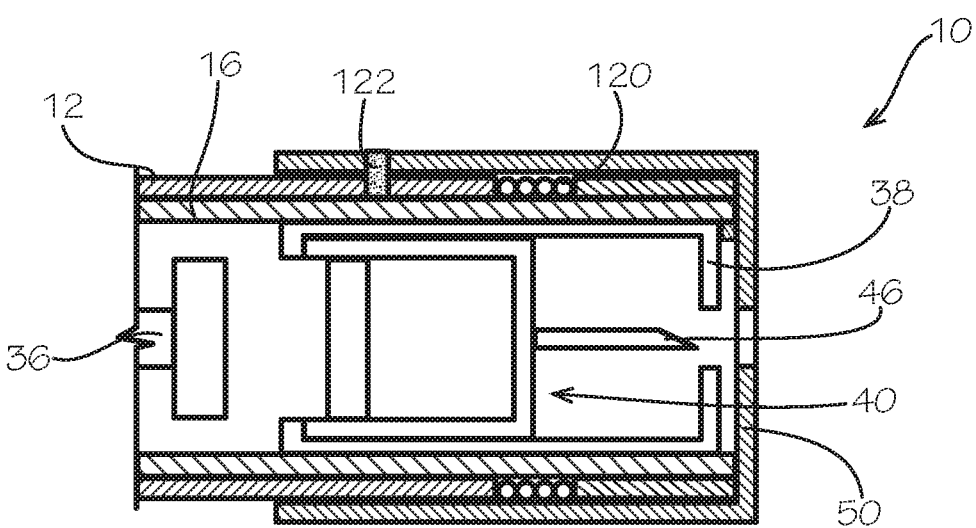
FIG. 28A is a detailed cross sectional view of an embodiment of an expandable sheath of the present disclosure prior to compression of the sheath against the desired object.
Figure 28B:
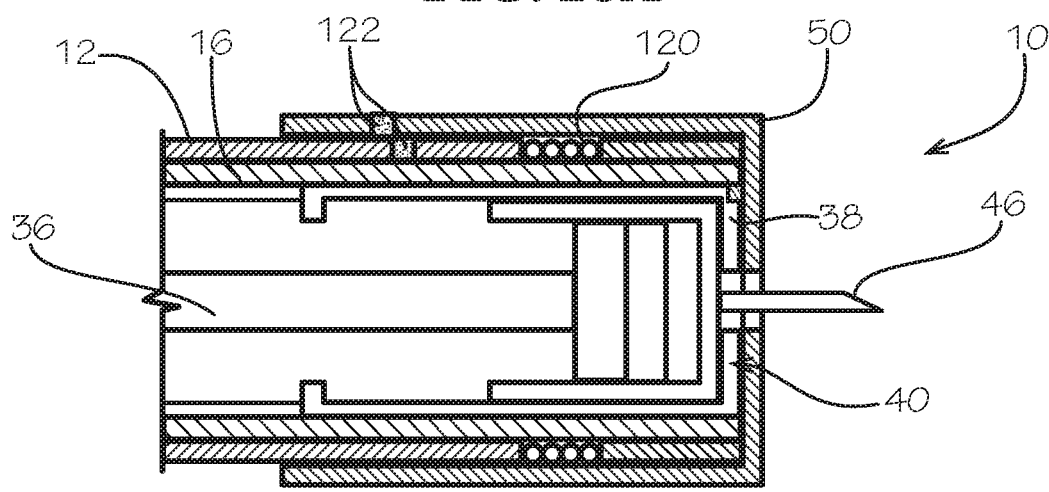
FIG. 28B is a detailed cross sectional view of the expandable sheath of FIG. 28A once compressed after actuation of the injection device.
Figure 28C:
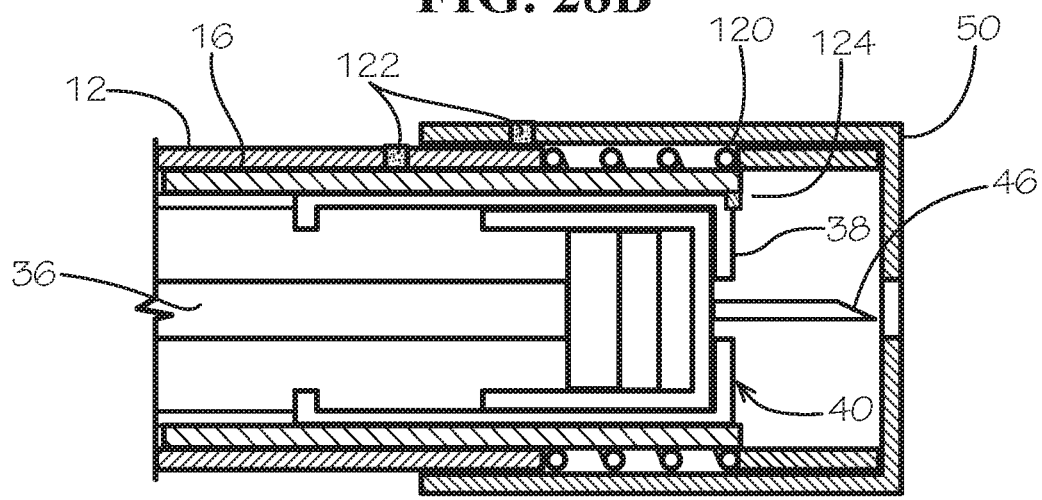
FIG. 28C is a detailed cross sectional view of the expandable sheath of FIG. 28B once the injection device is removed from an object and the expandable sheath is expanded to cover a needle of the device.

For instance as shown in FIGS. 28A-28C, in some embodiments, end cap 50 can act as an expandable sheath. Injection device 10 can include a cap spring 120 positioned between end cap 50 and hollow guide shell 12. End cap 50 and cap spring 120 can initially be in a compressed state, end cap 50 being retained in such a compressed state by a frangible cap retention member 122. When end cap 50 is pushed against an intended object, as shown in FIG. 28B, end cap 50 can be further compressed to break frangible cap retention member 122 and move the driver magnet to the second slider position to actuate injection device 10. Needle 46 of cartridge 40 can subsequently be pushed through cartridge holder 38, out of injection device 10 and into the desired object. Fluid in cartridge 40 can be injected from cartridge 40 and into the desired object. When the injection is complete and injection device 10 is pulled away from the desired object, end cap 50 is free to expand outward from injection device 10 with end cap retention member 122 broken such that end cap 50 can cover or protect needle 46 extending from cartridge 40, as shown in FIG. 28C. As such, end cap 50 can be released upon actuation of injection device 10 such that end cap 50 is expandable to cover needle 46 once injection device 10 is removed from a desired object. Such a configuration can help reduce the occurrence of unwanted needle sticks. In some embodiments, slider member 16 can include a cartridge holder stop 124 which can retain cartridge holder 38 and cartridge 40 in a desired position after the injection is complete such that as end cap 50 expands, cartridge holder 38 and cartridge 40 do not move, allowing end cap 50 to extend over and cover needle 46 of cartridge 40.

In other embodiments, hollow guide shell 12 can include a generally L-shaped groove having a longitudinal portion and a lateral portion, the lateral portion extending from the longitudinal portion toward injection end 14 of hollow guide shell 12 at an acute angle with the longitudinal portion. End cap 50 can include a protrusion that is received in the L-Shaped groove when end cap 50 is positioned on injection end 14 of hollow guide shell 12. The protrusion can generally be positioned in the lateral portion of the L-shaped groove prior to actuation. End cap 50 can be biased toward injection end, for instance via a spring. As end cap 50 is pressed against an object the force on the end cap 50 can cause the protrusion to travel up the lateral portion of the L-shaped groove until the protrusion is positioned in the longitudinal portion of the L-shaped groove. When the pressure on the end cap is releases, the protrusion is allowed to slide in the longitudinal channel to an extended position thereby covering needle 46 as needle 46 is removed from the object. After used, the end cap 50 can be once again compressed and twisted to place the protrusion within the lateral portion of the L-shaped groove to bias the end cap in a retracted position.

In some embodiments, the protrusion can be located on hollow guide shell 12 and the generally L-shaped groove can be defined in end cap 50. In some embodiments, end cap 50 can be made of a slick or low friction material to help prevent any friction against the object as end cap 50 rotates on hollow guide shell 12 during actuation.

In still other embodiments, the expandable sheath can include a mechanism similar to that of a retractable click style pen. An expandable sheath assembly can include a cam body rotatably disposed on hollow guide shell 12, the cam body being spring biased toward injection end 14. An expandable sheath can be slidably disposed on hollow guide shell 12 and can engage the cam body such that the cam body moves in a longitudinal direction corresponding to the movement of the sheath. The sheath can move longitudinally on hollow guide shell 12 but does not rotate. One or more sheath stop members can be fixedly connected to hollow guide shell 12. The cam body can include at least one angled protrusion. The sheath can have a sheath back end that includes a sheath angled protrusion that engages the angled protrusion on the cam body as the sheath moves in a rearward direction. The angled protrusion of the cam body can initially be maintained in a retracted position between the sheath angled protrusion and a sheath stop member. When the sheath of the device is pressed against an object, the sheath moves the cam body longitudinally in a rearward direction until the angled protrusion of the cam body clears the sheath stop member. The angled engagement between the cam body and sheath angled protrusions can rotate the cam body as the cam body clears the sheath stop member. As the expandable sheath is depressed as the device 10 is removed from the object after injection, the angled protrusion on the cam body can slide on an opposite side of the sheath stop member, thus allowing the cam body and the sheath to move to an extended position on the hollow guide shell wherein the sheath can cover or extend beyond a needle of a deployed cartridge.

In some embodiments, the sheath and cam body can be configured with multiple sheath corresponding angled protrusions that can engage one another and the sheath stop member to repetitively rotate the cam body between a retracted and an extended oriented as the sheath is repetitively pressed and depressed between uses such that the expandable sheath concept can be reloaded or re-primed.

Thus, although there have been described particular embodiments of the present invention of a new and useful A Magnetic Driver Device Used To Power An Auto Injector, it is not intended that such references to any particular embodiments be construed as limitations upon the scope of this invention.

What is claimed is:

1. An injection device comprising:
a hollow guide shell including an injection end, a back end, and a longitudinal axis;
an actuator magnet positioned in the hollow guide shell, the actuator magnet having a first actuator magnet pole oriented toward the back end of the hollow guide shell and a second actuator magnet pole oriented toward the injection end of the hollow guide shell;
a driver magnet positioned radially outward from the hollow guide shell, the driver magnet having a first driver magnet pole oriented toward the longitudinal axis of the hollow guide shell and a second driver magnet pole oriented away from the longitudinal axis of the hollow guide shell, the first actuator pole and the first driver magnet pole being like poles, and a driver magnet axis extending from the first driver magnet pole to the second driver magnet pole;
a rear stop on the back end of the hollow guide shell;
wherein when the first actuator magnet pole is positioned between the back end of the hollow guide shell and the driver magnet axis, the driver magnet exerts a retracting force on the actuator magnet that biases the actuator magnet against the rear stop and an actuation energy is required to move the first actuator magnet pole across the driver magnet axis.

2. The device of claim 1, wherein the rear stop is adjustable and can adjust the position of the first actuator magnet pole relative to the driver magnet axis when the first actuator magnet pole is positioned between the driver magnet axis and the back end of the hollow guide tube.

3. The device of claim 1, wherein the rear stop can move longitudinally on the hollow guide shell to adjust the actuation energy needed to actuate the injection device.

4. The device of claim 1, wherein the actuation energy is sufficient such that the injection device does not accidentally actuate.

5. The device of claim 1, wherein the force applied to activate the injection device is less than 5 pounds.

6. The device of claim 1, wherein the actuation energy is minimized.

7. The device of claim 1, wherein the actuation energy approaches zero.

8. The device of claim 1, wherein the rear stop is fixed to the hollow guide shell.

9. The device of claim 1, wherein the rear stop is threadingly engaged with the hollow guide shell.

10. The device of claim 1, wherein the actuation energy is applied by pushing on the back end of the hollow guide shell.

11. The device of claim 1, further comprising an actuator button at the back end of the hollow guide shell that is operably connected to the activator magnet and capable of moving the first actuator magnet pole from the back end of the hollow guide shell across the driver magnet axis.

12. The device of claim 11, wherein the force applied to the actuator button to move the first actuator magnet pole from the back end of the hollow guide shell across the driver magnet axis is less than 5 pounds.

13. The device of claim 11, wherein the force applied to the actuator button to move the first actuator magnet pole from the back end of the hollow guide shell across the driver magnet axis is sufficient such that the injection device does not accidentally actuate.

14. An injection device comprising:
a hollow guide shell including an injection end, a back end, and a longitudinal axis;
an actuator magnet positioned in the hollow guide shell, the actuator magnet having a first actuator magnet pole oriented toward the back end of the hollow guide shell and a second actuator magnet pole oriented toward the injection end of the hollow guide shell;
a driver magnet positioned radially outward about the hollow guide shell, the driver magnet having a first driver magnet pole oriented toward the longitudinal axis of the hollow guide shell and a second driver magnet pole oriented away from the longitudinal axis of the hollow guide shell, the first actuator pole and the first driver magnet pole being like poles, and a driver magnet axis extending from the first driver magnet pole to the second driver magnet pole;
an adjustable rear stop on the back end of the hollow guide shell,
wherein when the first actuator magnet pole is positioned between the back end of the hollow guide shell and the driver magnet axis, the driver magnet exerts a retracting force on the actuator magnet that biases the actuator magnet against the rear stop and an actuation energy is required to move the first actuator magnet pole across the driver magnet axis and the adjustable rear stop can move longitudinally on the hollow guide shell to adjust the actuation energy needed to actuate the injection device.

15. The device of claim 14, wherein the actuation energy is sufficient such that the injection device does not accidentally actuate.

16. The device of claim 14, wherein the force applied to activate the injection device is less than 5 pounds.

17. A device comprising:
a hollow guide shell including a longitudinal axis having a back end and an end at the opposite end of the hollow guide shell;
an actuator magnet positioned in the hollow guide shell, the actuator magnet having a first actuator magnet pole oriented toward the back end of the hollow guide shell and a second actuator magnet pole oriented toward the opposite end of the hollow guide shell;
a driver magnet positioned radially outward about the hollow guide shell, the driver magnet having a first driver magnet pole oriented toward the longitudinal axis of the hollow guide shell and a second driver magnet pole oriented away from the longitudinal axis of the hollow guide shell, the first actuator pole and the first driver magnet pole being like poles, and a driver magnet axis extending from the first driver magnet pole to the second driver magnet pole;
a rear stop on the back end of the hollow guide shell,
wherein when the first actuator magnet pole is positioned between the back end of the hollow guide shell and the driver magnet axis, the driver magnet exerts a retracting force on the actuator magnet that biases the actuator magnet against the rear stop and an actuation energy is required to move the first actuator magnet pole across the driver magnet axis.

18. The device of claim 17, wherein the rear stop is adjustable and can adjust the position of the first actuator magnet pole relative to the driver magnet axis when the actuator magnet is positioned between the driver magnet axis and the back end of the hollow guide tube.

19. The device of claim 17, wherein the rear stop can move longitudinally on the hollow guide shell to adjust the actuation energy needed to actuate the injection device.

20. The device of claim 17, wherein the force applied to activate the injection device is less than 5 pounds.

* * * * *